(12) United States Patent
Ohkawa et al.

(10) Patent No.: US 8,435,530 B2
(45) Date of Patent: *May 7, 2013

(54) METHODS FOR SUPPRESSING ACTIVITY OF ACTIVATED INTERFERON-PRODUCING CELLS

(75) Inventors: Jun Ohkawa, Saitama (JP); Yumiko Kamogawa, Tokyo (JP)

(73) Assignee: SBI Biotech Co., Ltd., Tokyo (JP)

( * ) Notice: Subject to any disclaimer, the term of this patent is extended or adjusted under 35 U.S.C. 154(b) by 1135 days.

This patent is subject to a terminal disclaimer.

(21) Appl. No.: 11/629,045

(22) PCT Filed: Jun. 9, 2005

(86) PCT No.: PCT/JP2005/010561
§ 371 (c)(1),
(2), (4) Date: Aug. 21, 2007

(87) PCT Pub. No.: WO2006/008886
PCT Pub. Date: Jan. 26, 2006

(65) Prior Publication Data
US 2008/0305121 A1 Dec. 11, 2008

(30) Foreign Application Priority Data
Jun. 11, 2004 (JP) ................. 2004-173767

(51) Int. Cl.
*A61K 39/00* (2006.01)
*A61K 39/395* (2006.01)
*C12N 5/077* (2010.01)

(52) U.S. Cl.
USPC ............... 424/184.1; 424/185.1; 424/141.1; 424/142.1; 435/7.1; 435/326

(58) Field of Classification Search .................. None
See application file for complete search history.

(56) References Cited

U.S. PATENT DOCUMENTS

| 7,592,005 B2 | 9/2009 | Tahara |
| 2004/0136982 A1 | 7/2004 | Tahara |

FOREIGN PATENT DOCUMENTS

| EP | 1 059 533 A1 | 12/2000 |
| EP | 1 354 896 A1 | 10/2003 |
| WO | WO 95/10536 A1 | 4/1995 |
| WO | WO 99/43703 | 9/1999 |
| WO | WO 99/43803 A1 | 9/1999 |
| WO | WO 03/024404 A2 | 3/2003 |
| WO | WO 2004/013325 A1 | 2/2004 |
| WO | WO-02/057316 A1 | 7/2007 |

OTHER PUBLICATIONS

Ngo et al., 1994, The Protein Folding Problem and Tertiary Structure Prediction, pp. 492-495.*
Wells, Aditivity of Mutational Effects in Proteins, 1990, Biochemistry, vol. 26, No. 37, pp. 8509-8517.*
Asselin-Paturel et al., "Mouse Strain Differences in Plasmacytoid Dendritic Cell Frequency and Function Revealed by a Novel Monoclonal Antibody," *The Journal of Immunology*, 2003, 171(12): 6466-77.
Blanco et al., "Induction of Dendritic Cell Differentiation by IFN-α in Systemic Lupus Erythematosus," *Science*, 2001, 294(5546):1540-3.
Blasius et al., "A cell-surface molecule selectively expressed on murine natural interferon-producing cells that blocks secretion of interferon-alpha," *Blood*, 2004, 103(11):4201-6.
Dzionek et al., "BDCA-2, BDCA-3, and BDCA-4: Three Markers for Distinct Subsets of Dendritic Cells in Human Peripheral Blood," *J. Immunol.*, 2000, 165(11):6037-46.
Hopkins & Meager, "Cytokines in synovial fluid: II. The presence of tumour necrosis factor and interferon," *Clin. Exp. Immunol.*, 1988, 73(1):88-92.
Ishikawa et al., "Molecular Cloning and Chromosomal Mapping of a Bone Marrow Stromal Cell Surface Gene, BST2, That May Be Involved in Pre-B-Cell Growth," *Genomics*, 1995, 26(3):527-34.
Pérez et al., "Myasthenia Gravis Induced by Alpha-Interferon Therapy," *Am. J. Hematol.*, 1995, 49(4):365-6.
Shiozawa et al., "Interferon-Alpha in Lupus Psychosis," *Arthritis Rheum.*, 1992, 35(4):417-22.
Wada et al., "Antithyroid Peroxidase Antibody and Development of Silent Thyroiditis during Interferon-α2a Treatment of Chronic Hepatitis C," *Am. J. Gastroenterol.*, 1995, 90(8):1366-7.
EP Search Report for 05748946.0-2402, Nov. 6, 2007, Ginkgo Biomedical Research Institute Co., Ltd.
Ozaki, S. et al. (1997) "Immunotherapy of Multiple Myeloma With a Monoclonal Antibody Directed Against a Plasma Cell-Specific Antigen, HM1.24," Blood 90(8): 3179-3186.
Ozaki, S. et al. (1998) "Radioimmunodetection of Human Myeloma Xenografts with a Monoclonal Antibody Directed against a Plasma Cell Specific Antigen, HM1.24," Cancer 82(11):2184-2190.

* cited by examiner

*Primary Examiner* — Christine J Saoud
*Assistant Examiner* — Jegatheesan Seharaseyon
(74) *Attorney, Agent, or Firm* — Foley & Lardner LLP; Antoinette F. Konski; Alex Y. Nie

(57) ABSTRACT

The present invention provides agents for regulating the activity of interferon-producing cells (IPCs), which comprise as active ingredients antibodies that bind to BST2 and/or to its homologues, and methods for regulating IPC activity that use these antibodies. According to the present invention, the ability of IPCs to produce interferons (IFNs) and the number of cells can be directly regulated. The present invention also provides uses of BST2 and/or its homologues as markers for IPC activation. Compounds that regulate IPC activation can be screened using the markers for IPC activation.

15 Claims, 18 Drawing Sheets

FIG. 2
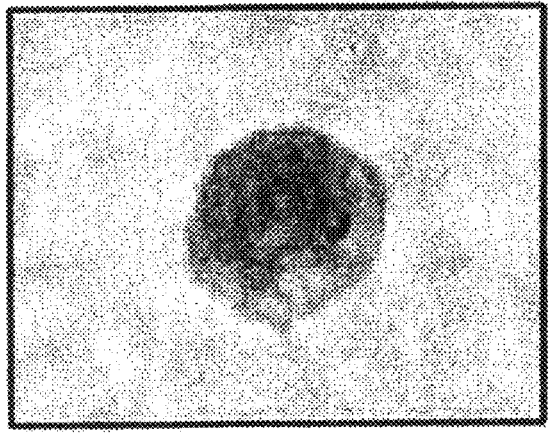 (a) CELL BEFORE INFECTION
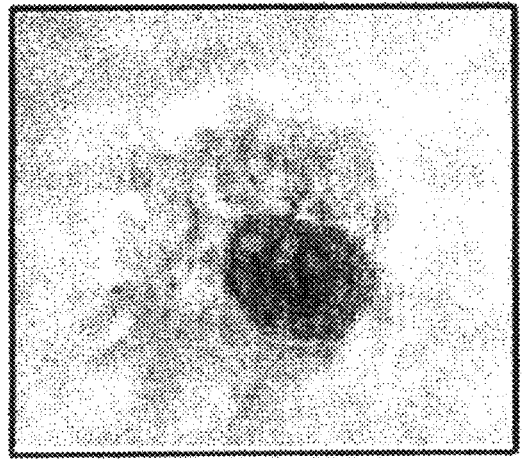 (b) PR8-INFECTED CELL

```
                                    TRANSMEMBRANE REGION
mBST2D    1:MAPSFYHYLPVPMDEMGGKQGWGSHRQWLGAAILVVLFGVTLVILTIYFAVTANSVACRD  60
(SEQ ID NO:10)
mBST2H    1:MAPSFYHYLPVPMDEMGGKQGWGSHRQWLGAAILVVLFGVTLVILTIYFAVTANSVACRD  60
(SEQ ID NO:8)
mBST2HS   1:MAPSFYHYLPVPMDEMGGKQGWGSHRQWLGAAILVVLFGVTLVILTIYFAVTANSVACRD  60
(SEQ ID NO:23)
            ************************************************************ mBST2D   61:GLRAQAECRNTTHLLQRQLTRTQDSLLQAETQANSCNLTVVTLQESLEKKVSQALEQQAR 120 mBST2H   61:GLRAQAECRNTTHLLQRQLTRTQDSLLQAETQANSCNLTVVTLQESLEKKVSQALEQQAR 120 mBST2HS  61:GLRAQAECRNTTHLLQRQLTRTQDSLLQAETQANSCNLTVMKSRS                105
            *****************************************.....

mBST2D  121:IKELENEVTKLNQELENLRIQKETSSTVQVNSGSSMVVSSLLVLKVSLFLLF         172 mBST2H  121:IKELENEVTKLNQELENLRLETALPAHRHPLPSRLHFLQNLGSTWLTQSTAQDPKGDF   178
            ..................
```

(b)

MOUSE BST2 (mBST2) GENE

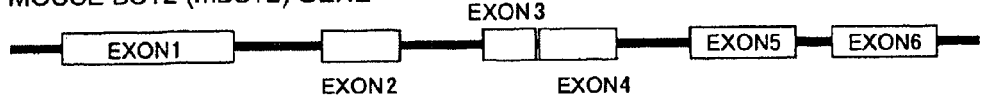

mBST2D

mBST2H

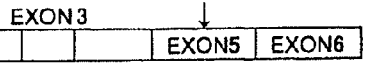

mBST2HS

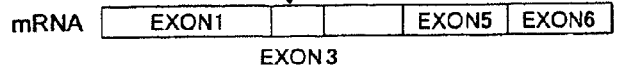

FIG. 9 hBST-2D

hBST-2H and HS

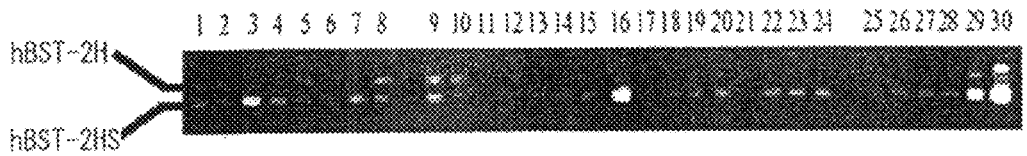

1: HEART
2: BRAIN
3: PLACENTA
4: LUNG
5: LIVER
6: SKELETAL MUSCLE
7: KIDNEY
8: PANCREAS
9: SPLEEN
10: THYMUS
11: PERIPHERAL LEUKOCYTE
12: LYMPH NODE
13: TONSIL
14: FETAL HEPATOCYTE
15: BONE MARROW
16: RESTING CD14 CELL
17: MONONUCLEAR CELL
18: RESTING CD8 CELL
19: RESTING CD4 CELL
20: RESTING CD19 CELL
21: ACTIVATED CD19 CELL
22: ACTIVATED MONONUCLEAR CELL
23: ACTIVATED CD4 CELL
24: ACTIVATED CD8 CELL
25: CD14 CELL
26: CD19 CELL
27: CD3 CELL
28: CD56 CELL
29: IPC
30: IPC (HSV-INFECTED)

FIG. 10
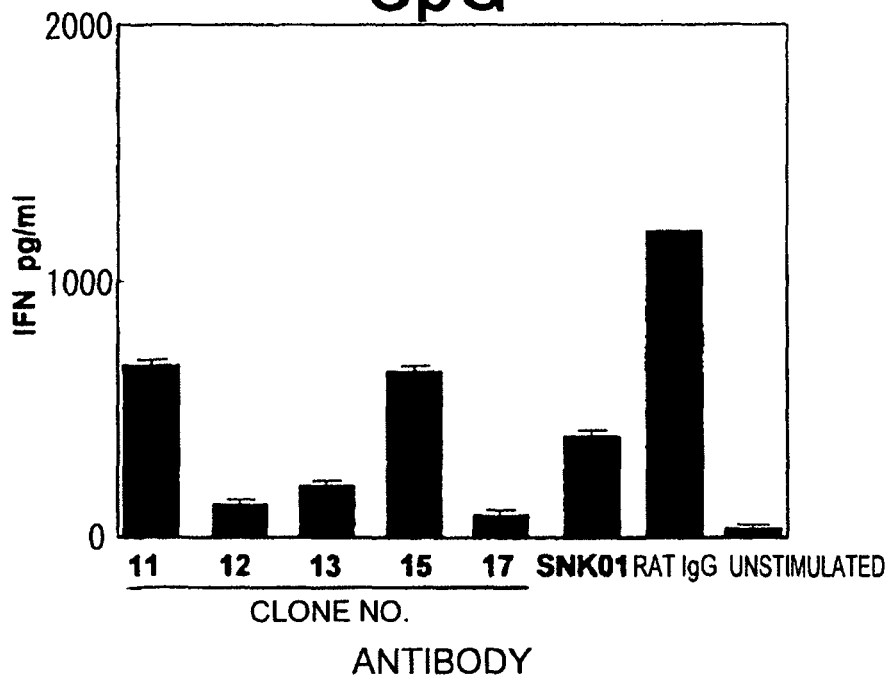
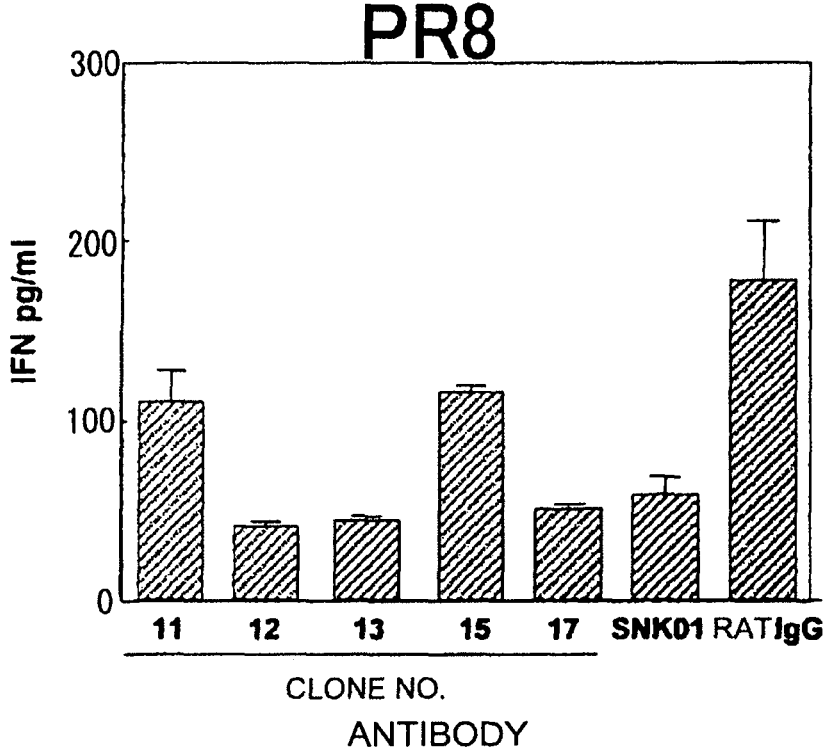

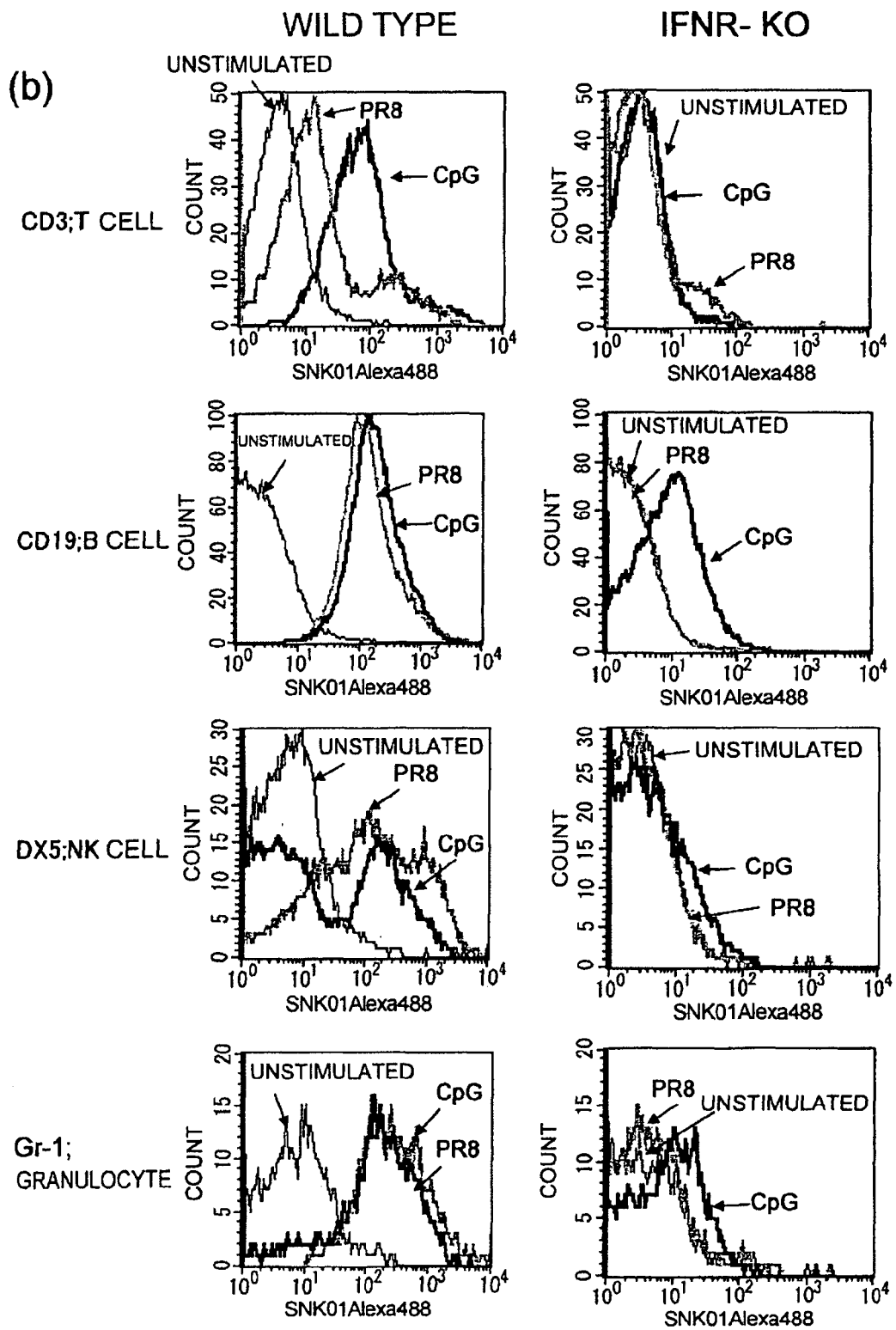
FIG. 12 (contd.)

FIG. 16
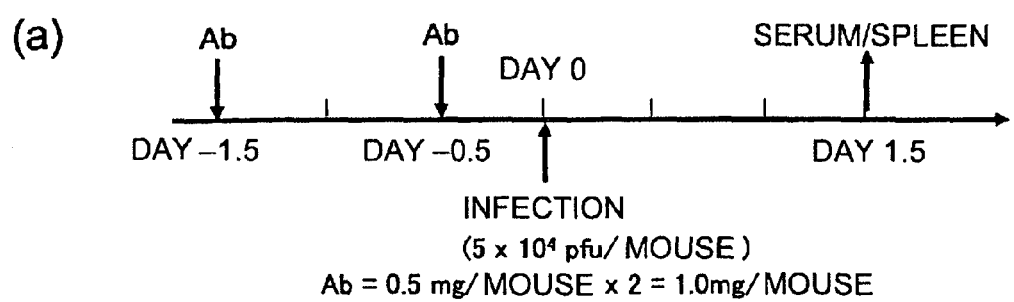
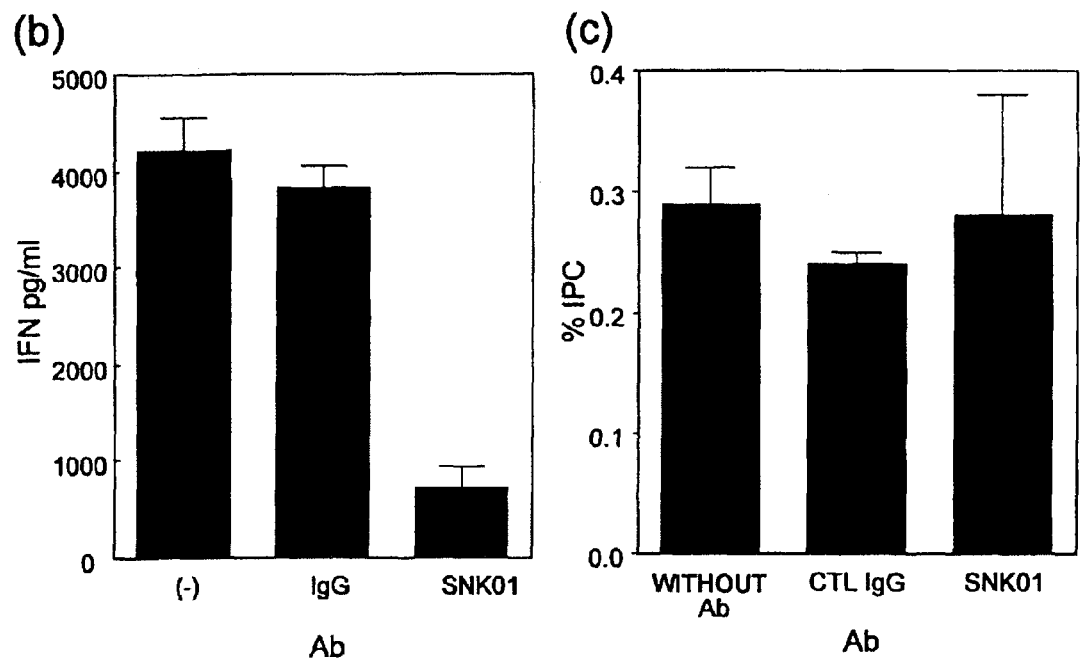

FIG. 17
(a)
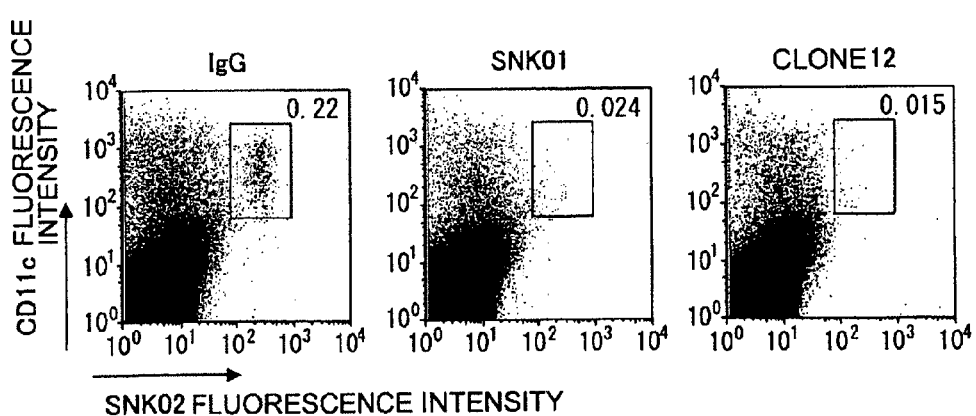
(b)
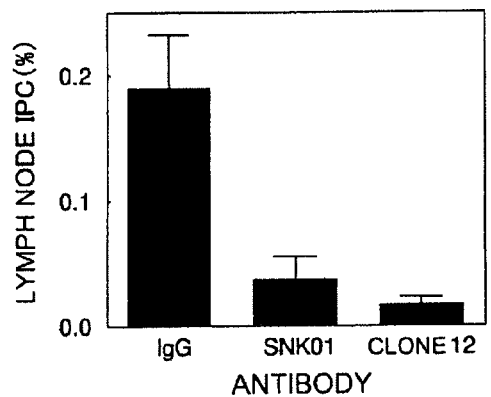
(c)
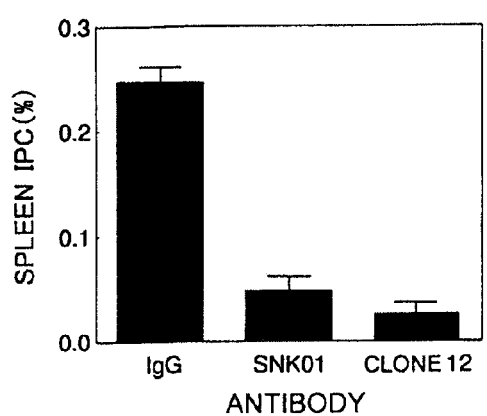
(d)
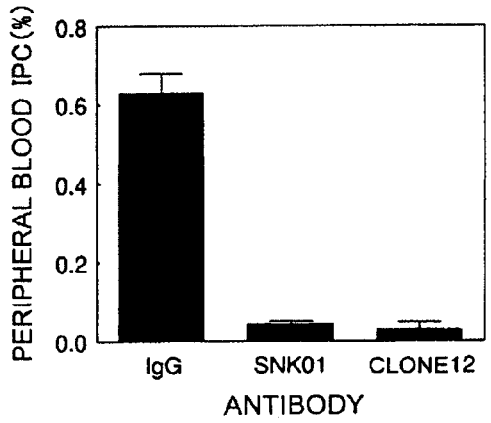

METHODS FOR SUPPRESSING ACTIVITY OF ACTIVATED INTERFERON-PRODUCING CELLS

CROSS-REFERENCE TO RELATED APPLICATIONS

This application is a 35 USC §371 U.S. national stage application of International Application WO 2006/008886, filed on Jun. 9, 2005, which in turn claims the priority benefit under 35 USC §119(a) of application JP 2004-173767, filed Jun. 11, 2004, the contents of which are hereby incorporated by reference.

TECHNICAL FIELD

The present invention relates to agents and methods for regulating the activity of interferon-producing cells (IPCs).

BACKGROUND ART

Interferon α (IFNα; hereinafter interferon is abbreviated to "IFN") and interferon β (IFNβ) are known as type 1 IFNs with antiviral or anti-tumor activity. In addition, IFNα has been shown to be involved in autoimmune diseases. For example, aberrant production of IFNα has been reported in patients with the autoimmune diseases listed below. Neutralization of IFNα has also been suggested to relieve autoimmune symptoms.

systemic lupus erythematosus (Shiozawa et al., Arthr. & Rheum. 35, 412, 1992)

rheumatoid arthritis (Hopkins et al., Clin. Exp. Immunol. 73, 88, 1988)

Furthermore, cases where symptoms of autoimmune diseases have developed or been exacerbated by administration of recombinant IFNα2 have also been reported (Wada et al., Am. J. Gastroenterol. 90, 136, 1995; Perez et al., Am. J. Hematol. 49, 365, 1995).

IFNα has been shown to induce the differentiation of dendritic cells. Dendritic cells are also antigen-presenting cells. The induction of dendritic cell differentiation is thus thought to constitute an important mechanism in autoimmune diseases. Indeed, a close correlation has been suggested between the induction of dendritic cell differentiation by IFNα and the onset of systemic lupus erythematosus (Blanco et al., Science, 16: 294, 1540-1543, 2001). Thus, IFNα is suggested to show close links with autoimmune diseases as well as anti-tumor activity.

Meanwhile, IPCs were identified as cells that produce large quantities of type 1 IFNs upon viral infection. Very few IPCs exist in the blood. IPCs are thought to accounts for 1% or less of peripheral blood lymphocytes. However, IPCs have an extremely strong IFN-producing ability. The ability of IPCs to produce IFNs is as much as 3000 pg/ml/$10^6$ cells, for example. Thus despite their small numbers, IPCs can be said to produce the majority of IFNα and IFNβ in the blood.

IPCs are undifferentiated lymphocytic dendritic cells that are positioned as precursor cells of dendritic cells. IPCs are also called plasmacytoid dendritic cells. When stimulated with viruses, IPCs differentiate into dendritic cells that induce the production of IFN-γ and IL-10 by T cells. IPCs also differentiate into dendritic cells when stimulated with IL-3. Such dendritic cells that differentiated upon stimulation with IL-3 induce the production of Th2 cytokines (IL-4, IL-5, and IL-10) by T cells. As described above, IPCs have the property of differentiating into different types of dendritic cells depending on the type of stimulation.

Thus, IPCs are cells with two aspects: they are IFN-producing cells, and also dendritic cell precursor cells. Both cells play important roles in the immune system. Therefore, IPCs are important cells that contribute to the immune system in various ways.

[Non-patent Document 1] Shiozawa et al., Arthr. & Rheum. 35, 412, 1992

[Non-patent Document 2] Hopkins et al., Clin. Exp. Immunol. 73, 88, 1988

[Non-patent Document 3] Wada et al., Am. J. Gastroenterol. 90, 136, 1995

[Non-patent Document 4] Perez et al., Am. J. Hematol. 49, 365, 1995

[Non-patent Document 5] Blanco et al., Science, 16:294, 1540-1543, 2001

DISCLOSURE OF THE INVENTION

Problems to be Solved by the Invention

An objective of the present invention is to provide agents and methods for regulating the activity of IPCs. Another objective of the present invention is to provide markers that can be used as indicators of IPC activation. Still another objective of the present invention is to provide screening methods that use such markers of IPC activation, and to provide methods for isolating or detecting activated IPCs.

Means to Solve the Problems

When regulating the activities of humoral factors such as IFNs, it is effective to administer antibodies that recognize these factors. For example, autoimmune disease therapies using antibodies against interleukin (IL)-1 or IL-4 have been put to practical use (Guler et al., Arthritis Rheum., 44. S307, 2001). Likewise, neutralizing antibodies against interferons are thought to be potential therapeutic agents for autoimmune diseases (Stewart, T A. Cytokine Growth Factor Rev. 14; 139-154, 2003). The same approach is also predicted to be effective for IFNs produced by IPCs. However, such approaches are based on inhibiting the activities of humoral factors after their production. More substantial therapeutic effects can be produced if the production of target humoral factors can be directly regulated.

Antibodies recognizing human IPCs have been reported. For example, anti-BDCA-2 monoclonal antibodies and anti-BDCA-4 monoclonal antibodies (Dzionek A. et al. J. Immunol. 165: 6037-6046, 2000) are specific to human IPCs. Of the above, anti-BDCA-2 monoclonal antibodies has been found to have the ability to suppress IFN production by human IPCs. Further, monoclonal antibodies that recognize mouse IPCs have also been reported to suppress interferon production (Blood 2004 Jun. 1; 103/11:4201-4206. Epub 2003 December). Monoclonal antibodies against mouse plasma cell-like dendritic cells (plasmacytoid dendritic cells) have been reported to reduce the number of dendritic cells (J. Immunol. 2003, 171:6466-6477).

BDCA2 was identified as an IPC-specific antigen. BDCA2 is constitutively expressed in IPCs. That is, antibodies recognizing BDCA2 bind to IPCs regardless of the level of IPC activation. In contrast, IFNs are produced by activated IPCs. Thus it would be ideal if antibodies that selectively act on activated IPCs could be obtained. Other than reports on BDCA-recognizing monoclonal antibodies, there are no reports that identify antigen molecules recognized by monoclonal antibodies, nor that identify their expression patterns.

The efficiency of treatment can be improved by selective action towards activated IPCs. Specifically, desired therapeutic effects can be obtained using smaller amounts of antibodies. In addition, selective action on the cells of interest can reduce the potential for unpredictable side effects. Based on this concept, the present inventors intensively studied methods that act specifically on activated IPCs and that can regulate their activity. As a result, the present inventors demonstrated that antibodies that bind to either or both of BST2 and its homologues acted on activated IPCs and regulated their activity. The present inventors thus completed the present invention. As described above, antibodies against BDCA-2 also suppress IFN production. However, BDCA-2 differs from BST2 in that BDCA-2 is expressed constitutively in IPCs regardless of the level of IPC activation. In addition, antibodies against BDCA-2 have been reported to enhance IL-12 production (Dzionek, A. et al. Hum Immunol. 63; 1133-1348, 2002).

The present inventors also discovered that BST2 and its homologues could be used as indicators for IPC activation, thus completing the present invention. Specifically, the present invention relates to the following agents and methods for regulating the activity of IPCs, methods for producing these agents, methods for detecting and separating activated IPCs, methods for determining IPC activation levels, methods for detecting the activity of regulating IPC activation, and methods of screening for substances with these activities:

[1] an agent for suppressing an activity of an interferon-producing cell, which comprises as an active ingredient an antibody recognizing either or both of BST2 and a homologue thereof;

[2] the agent of [1] for suppressing an activity of an interferon-producing cell, wherein the activity of the interferon-producing cell is either or both of the activity of producing interferon and survival of the interferon-producing cell;

[3] the agent of [2] for suppressing an activity of an interferon-producing cell, wherein the activity of the interferon-producing cell is the activity of producing interferon, and the interferon is a type 1 interferon;

[4] the agent of [1] for suppressing an activity of an interferon-producing cell, wherein the BST2 or homologue thereof is a protein comprising an amino acid sequence selected from the group consisting of SEQ ID NOs: 2, 4, and 6;

[5] the agent of [4] for suppressing an activity of an interferon-producing cell, which comprises as an active ingredient an antibody recognizing a protein comprising the amino acid sequence of SEQ ID NO: 4;

[6] the agent of [4] for suppressing an activity of an interferon-producing cell, which comprises as an active ingredient an antibody that recognizes all proteins comprising the amino acid sequences of SEQ ID NOs: 2, 4, and 6;

[7] a method for suppressing an activity of an interferon-producing cell, which comprises the step of contacting the interferon-producing cell with an antibody recognizing either or both of BST2 and a homologue thereof;

[8] the method of [5] for suppressing an activity of an interferon-producing cell, wherein the activity of the interferon-producing cell is either or both of the activity of producing interferon and survival of the interferon-producing cell;

[9] a method for producing an antibody that suppresses an activity of an interferon-producing cell, which comprises the steps of:

(1) administering an animal to be immunized with either or both of BST2 and a homologue thereof, or a fragment thereof as an immunogen, (2) selecting an antibody-producing cell that produces an antibody recognizing either or both of BST2 and a homologue thereof from the antibody-producing cells of the immunized animal of (1), (3) culturing the antibody-producing cell selected in (2), or isolating a gene encoding an antibody produced by the antibody-producing cell, and culturing a cell carrying and capable of expressing the gene, and (4) collecting an antibody that suppresses an activity of an interferon-producing cell from the culture of (3);

[10] the method of [9], wherein the immunogen is an interferon-producing cell collected from a human;

[11] a method for detecting an activated interferon-producing cell, which comprises the step of detecting an indicator substance of the following (a) to (d):

(a) a polynucleotide comprising a nucleotide sequence selected from the group consisting of SEQ ID NOs: 1, 3, and 5, (b) a polynucleotide comprising a consecutive nucleotide sequence selected from a nucleotide sequence selected from the group consisting of SEQ ID NOs: 1, 3, and 5, (c) a protein comprising an amino acid sequence selected from the group consisting of SEQ ID NOs: 2, 4, and 6, and (d) a protein comprising a consecutive amino acid sequence selected from an amino acid sequence selected from the group consisting of SEQ ID NOs: 2, 4, and 6;

[12] a method for separating an activated interferon-producing cell, which comprises the step of isolating an indicator substance of the following (a) to (d):

(a) a polynucleotide comprising a nucleotide sequence selected from the group consisting of SEQ ID NOs: 1, 3, and 5, (b) a polynucleotide comprising a consecutive nucleotide sequence selected from a nucleotide sequence selected from the group consisting of SEQ ID NOs: 1, 3, and 5, (c) a protein comprising an amino acid sequence selected from the group consisting of SEQ ID NOs: 2, 4, and 6, and (d) a protein comprising a consecutive amino acid sequence selected from an amino acid sequence selected from the group consisting of SEQ ID NOs: 2, 4, and 6;

[13] a reagent for detecting an activated interferon-producing cell, which comprises an antibody that recognizes a protein comprising an amino acid sequence selected from the group consisting of SEQ ID NOs: 2, 4, and 6;

[14] a reagent for detecting an activated interferon-producing cell, which comprises an oligonucleotide comprising a nucleotide sequence of at least 15 consecutive nucleotides selected from a nucleotide sequence selected from the group consisting of SEQ ID NOs: 1, 3, and 5;

[15] a reagent for separating an activated interferon-producing cell, which comprises an antibody that recognizes a protein comprising an amino acid sequence selected from the group consisting of SEQ ID NOs: 2, 4, and 6;

[16] a method for determining a level of in vivo activation of an interferon-producing cell, which comprises the steps of:

(1) detecting either or both of cells expressing an indicator substance of (a) to (d), and an expression level of the indicator substance in an interferon-producing cell comprised in a sample collected from a living body:

(a) a polynucleotide comprising a nucleotide sequence selected from the group consisting of SEQ ID NOs: 1, 3, and 5, (b) a polynucleotide comprising a consecutive nucleotide sequence selected from a nucleotide sequence selected from the group consisting of SEQ ID NOs: 1, 3, and 5, (c) a protein comprising an amino acid sequence selected from the group consisting of SEQ ID NOs: 2, 4, and 6, and (d) a protein comprising a consecutive amino acid sequence selected from an amino acid sequence selected from the group consisting of SEQ ID NOs: 2, 4, and 6, and (2) relating either or both of the number of cells or the expression level determined in (1) to an activation level of an interferon-producing cell in a subject;

[17] the method of [16], wherein the sample collected from a living body is any selected from the group consisting of a body fluid, skin, synovial tissue, hematopoietic tissue, pus, alveolar lavage fluid, and a biopsy sample that can comprise blood cells;

[18] a method for detecting an activity of a test substance in regulating the activation of an interferon-producing cell, which comprises the steps of:

(1) contacting an interferon-producing cell with a cell stimulant along with a test substance, or contacting an interferon-producing cell with a cell stimulant before or after contact with a test substance, (2) determining the expression level of an indicator substance of (a) to (d) in the interferon-producing cell:

(a) a polynucleotide comprising a nucleotide sequence selected from the group consisting of SEQ ID NOs: 1, 3, and 5, (b) a polynucleotide comprising a consecutive nucleotide sequence selected from a nucleotide sequence selected from the group consisting of SEQ ID NOs: 1, 3, and 5, (c) a protein comprising an amino acid sequence selected from the group consisting of SEQ ID NOs: 2, 4, and 6, and (d) a protein comprising a consecutive amino acid sequence selected from an amino acid sequence selected from the group consisting of SEQ ID NOs: 2, 4, and 6, and (3) comparing the expression level of the indicator substance determined in (2) with that of a control, and detecting an activity of the test substance in enhancing the activation of the interferon-producing cell when the expression level is significantly higher than that of the control, or detecting an activity of the test substance in suppressing the activation of the interferon-producing cell when the expression level is significantly lower than that of the control;

[19] the method of [18], wherein the cell stimulant is at least one selected from the group consisting of a virus, a viral component, a bacterial DNA, and an interferon;

[20] a method of screening for a test substance with the activity of regulating the activation of an interferon-producing cell, which comprises the steps of:

(1) measuring an activity of a test substance in regulating the activation of an interferon-producing cell using the method of [18], and (2) selecting a test compound with a strong activity of regulating the activation as compared to a control;

[21] a pharmaceutical composition for regulating an activity of an interferon-producing cell, which comprises as an active ingredient a test substance selected by the method of [20];

[22] a reagent for detecting an activity of regulating the activation of an interferon-producing cell, which comprises an antibody that recognizes a protein comprising an amino acid sequence selected from the group consisting of SEQ ID NOs: 2, 4, and 6;

[23] a reagent for detecting an activity of regulating the activation of an interferon-producing cell, which comprises an oligonucleotide comprising a nucleotide sequence of at least 15 consecutive nucleotides selected from a nucleotide sequence selected from the group consisting of SEQ ID NOs: 1, 3, and 5;

[24] a polynucleotide of any one of the following (i) to (vi):

(i) a polynucleotide encoding a protein comprising the amino acid sequence of SEQ ID NO: 4 or 6, (ii) a polynucleotide comprising a coding region in the nucleotide sequence of SEQ ID NO: 3 or 5, (iii) a polynucleotide encoding a protein which comprises an amino acid sequence with a substitution, deletion, insertion, and/or addition of one or more amino acids in the amino acid sequence of SEQ ID NO: 4 or 6 and which is functionally equivalent to a protein comprising the amino acid sequence of SEQ ID NO: 2, (iv) a polynucleotide that hybridizes under stringent conditions to a DNA comprising the nucleotide sequence of SEQ ID NO: 3 or 5, (v) a polynucleotide encoding the amino acid sequence of position 139 to 158 from the N terminus of the amino acid sequence of SEQ ID NO: 4, and (vi) a polynucleotide encoding the amino acid sequence of position 96 to 100 from the N terminus of the amino acid sequence of SEQ ID NO: 6;

[25] a protein comprising an amino acid sequence encoded by the polynucleotide of [24];

[26] an antibody against the protein of [25], which recognizes a region comprising the amino acid sequence of position 139 to 158 from the N terminus of the amino acid sequence of SEQ ID NO: 4:

[27] an antibody against the protein of [25], which recognizes a region comprising the amino acid sequence of position 96 to 100 from the N terminus of the amino acid sequence of SEQ ID NO: 6;

[28] the antibody of [26] or [27], which is a monoclonal antibody;

[29] a vector comprising the polynucleotide of [24];

[30] a transformed cell that carries the polynucleotide of [24] or a vector comprising the polynucleotide;

[31] a method for producing the protein of [25], which comprises the steps of culturing the transformed cell of [30] and collecting the protein of [25] from the culture;

[32] the hybridoma 3D3#7 deposited under FERM BP-10339, or the hybridoma 3G7#6 deposited under FERM BP-10340;

[33] a monoclonal antibody produced by the hybridoma 3D3#7 deposited under FERM BP-10339 or the hybridoma 3G7#6 deposited under FERM BP-10340, or a fragment thereof comprising an antigen-binding domain;

[34] a method for producing a monoclonal antibody or a fragment thereof comprising an antigen-binding domain, which comprises the steps of culturing the hybridoma 3D3#7 deposited under FERM BP-10339 or the hybridoma 3G7#6 deposited under FERM BP-10340, and collecting an immunoglobulin from the culture; and

[35] an agent for suppressing an activity of an interferon-producing cell, which comprises as an active ingredient a monoclonal antibody produced by the hybridoma 3D3#7 deposited under FERM BP-10339 or the hybridoma 3G7#6 deposited under FERM BP-10340, or a fragment thereof comprising an antigen-binding domain.

Effects of the Invention

The present invention provided techniques for acting on activated IPCs and suppressing their activity. Specifically, antibodies recognizing either or both of BST2 and its homologues bind to activated IPCs and suppress their activity. The antibodies recognizing either or both of BST2 and its homologues can be used as agents for suppressing IPC activity, or in methods for suppressing IPC activity. Since the expression levels of BST2 and its homologues are increased in activated IPCs, the agents or methods of the present invention for suppressing IPC activity act specifically on activated IPCs.

A few IPCs produce a large quantity of IFNs. IFN neutralization requires antibody molecules suited to the number of IFN molecules. However, the present invention directly suppresses the activity of IFN-producing cells. Thus, a stronger IFN-suppressing effect can be expected from fewer antibodies than when using anti-IFN antibodies for neutralization. Further, when IFNs are persistently produced, neutralization by IFN antibodies is predicted to be only transient. Since IPC activity is suppressed in the present invention, the effect of suppressing IFN production can be expected to be long lasting. Specifically, in a preferred embodiment of the present invention, antibodies recognizing BST2 or its homologues not only suppress IFN production in IPCs, but also reduce the number of cells. These effects act synergistically, effectively suppressing IFN production.

In the present invention, novel splicing variants BST2H and BST2HS, derived from human BST2 are also isolated. The antigen molecules identified in the present invention are expressed specifically in human IPCs, and thus are useful as markers for human IPCs. Specifically, the polynucleotides discovered in the present invention, which comprise nucleotide sequences of any SEQ ID selected from the group consisting of SEQ ID NOs: 1, 3, and 5, are useful as IPC markers. Proteins comprising the amino acid sequences encoded by these nucleotide sequences are also useful as IPC markers.

The present invention also identified the mouse homologues BST2H and BST2HS as novel molecules. Like the human molecules, these molecules are thought to be splicing variants of the known molecule mouse BST2D. These molecules are useful as markers for mouse IPCs.

The present invention also revealed that the expression levels of BST2 and its homologues were elevated along with IPC activation. Thus, the level of IPC activation can be evaluated by using these markers as indicators. The activity of regulating IPC activation can also be evaluated using these markers as indicators. Substances with this activity can be screened by evaluating the activity of various substances in regulating IPC activation. Such screening can discover agents that regulate IPC activation. Agents with the activity of regulating IPC activity, discovered based on the present invention, are useful as therapeutic agents for autoimmune and allergic diseases.

BRIEF DESCRIPTION OF THE DRAWINGS

FIG. 2 is micrographs (×400) showing the morphology of the cells separated by the monoclonal antibodies. (a): morphology before infection with influenza virus PR8; (b): morphology after 24 hours of culture with influenza virus PR8. The infected cells had dendrites and exhibited typical dendritic cell morphology.

FIG. 7 is diagrams showing the amino acid sequences and genomic structures of mouse BST2 and homologues thereof. (a) shows an alignment of the amino acid sequences of each of the isoforms. (b) shows exon maps.

FIG. 9 is photographs showing the results of comparing the expression levels of human BST2 mRNA between tissues and cells.

FIG. 10 is graphs showing the influence of prepared anti-mouse-BST2 monoclonal antibodies on interferon-producing ability. In these graphs, the horizontal axis indicates the types of hybridomas whose culture supernatants were used in the treatment, and the vertical axis indicates the IFNα concentration (pg/ml) in the culture supernatant. The panels labeled with CpG and PR8 show the results obtained by treatment with CpG and by infection with influenza virus PR8, respectively.

FIG. 16 shows analyses of mice administered with an anti-mouse-BST2 antibody SNK01 and infected with viruses. (a) shows the schedule of administration. (b) shows the serum IFNα concentration. The horizontal axis indicates the antibodies administered. (c) shows the proportion of IPCs in the spleen. The horizontal axis indicates the antibodies administered. The vertical axis indicates the IPC proportion. (–) indicates the group administered with PBS alone instead of the antibodies.

FIG. 17 shows analyses of cells collected from mice administered with an anti-mouse-BST2 antibody SNK01, clone 12, and a control antibody rat IgG (referred to as IgG). (a) shows examples of the results of FACS analysis of mouse lymph node cells administered with each antibody. The boxed cell fractions are IPCs. (b) is a graph showing the IPC proportion in lymph nodes, determined based on the results of (a). Likewise, (c) and (d) show the IPC proportions in the spleen and peripheral blood, respectively. The horizontal axes indicate the antibodies administered. The vertical axes indicate the IPC proportion.

BEST MODE FOR CARRYING OUT THE INVENTION

Figure 1:
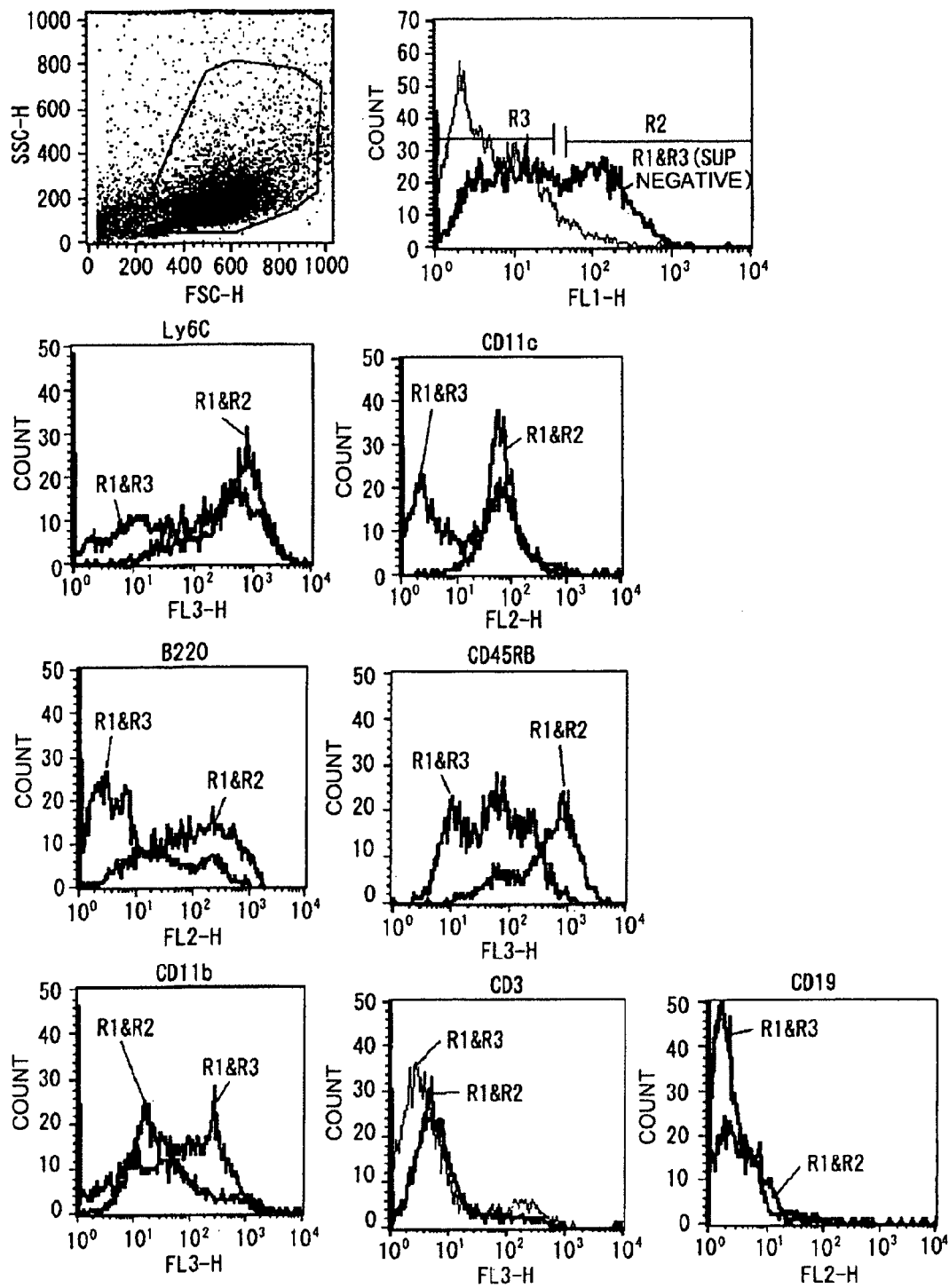
FIG. 1 is graphs showing FACS analyses in which the cell surface of mouse bone marrow cells cultured for ten days after addition of FLT-3 ligand (IPCs have been enriched) was stained with prepared antibodies and other markers. Positive and negative fractions of culture supernatant were labeled as R2 and R3, respectively. In the graphs, R1&R2 represents antibody-positive cell populations, and R1&R3 represents antibody-negative cell populations.

The present invention relates to agents for suppressing IPC activity, which comprise as active ingredients antibodies recognizing either or both of BST2 and its homologues. The present invention also relates to methods for suppressing IPC activity, which comprise the step of contacting IPCs with antibodies recognizing either or both of BST2 and its homologues. Furthermore, the present invention relates to methods for suppressing IPC activity in vivo, which comprise the step of administering antibodies recognizing either or both of BST2 and its homologues. The present invention also relates to uses of antibodies recognizing either or both of BST2 and its homologues in the production of agents for suppressing IPC activity.

IPCs are not particularly limited in the present invention and any cells may be used as long as the cells express either or both of human BST2 and its homologues, and produce IFNs. For example, IPCs in humans and mice have been shown to express either or both of BST2 and its homologues. Therefore, human and mouse IPCs are preferred as the IPCs of the present invention. In particular, the activation of human IPCs dramatically increases the expression levels of BST2 and its homologues. Thus, antibodies specifically recognizing BST2 and its homologues act specifically on activated IPCs in humans. Human IPCs are thus particularly preferred as the IPCs of the present invention.

In the present invention, a BST2 gene encodes a human-derived protein defined by the amino acid sequence of SEQ ID NO: 2. The amino acid sequence of SEQ ID NO: 2 is encoded by a cDNA comprising the nucleotide sequence of SEQ ID NO: 1. There is a report regarding the cDNA cloning and monoclonal antibodies of human BST2 (Ishikawa J. et al. Genomics 26:527, 1995; GenBank Acc#. D28137). BST2 was found to be a membrane protein able to support the growth of pre-B cells (Japanese Patent Application Kokai Publication No. (JP-A) H7-196694 (unexamined, published Japanese patent application)). The BST2 genomic gene and its promotor are also known (WO 99/43803). In addition, human BST2 has been shown to be an antigen recognized by the anti-HM1.24 antibody, a monoclonal antibody against myelomas (Ohmoto T. et al. B. B. R. C 258: 583, 1999). The anti-HM1.24 antibody is a monoclonal antibody established using a human plasma cell line as an antigen (Goto T. et al. Blood 84:1992, 1994).

The anti-HM1.24 antibody was further found to specifically recognize myelomas, and was humanized for myeloma therapy (Ozaki S. et al. Blood 93: 3922, 1999; WO 98/14580). The humanized anti-HM1.24 antibody has therapeutic effects on hematopoietic cancers (WO 02/064159). Currently, clinical trials aiming to put the antibody into practical use are being conducted. As described above, human BST2 is being used as a marker for hematopoietic tumors. However, to date, there have been no reports suggesting a relationship between IPCs and antibodies recognizing BST2.

In the present invention, BST2 comprises its homologues. Such homologues of BST2 can be defined as proteins functionally equivalent to a protein comprising the amino acid sequence of SEQ ID NO: 2. Such proteins comprise naturally occurring proteins. Generally, eukaryotic genes are polymorphic, as is known to be the case for IFN genes and others. Changes to nucleotide sequences due to these polymorphisms can result in substitutions, deletions, insertions, and/or additions of one or more amino acids. Thus, the BST2 homologues of the present invention also include human-derived proteins comprising an amino acid sequence with a substitution, deletion, insertion, and/or addition of one or more amino acids in the amino acid sequence of SEQ ID NO: 2, which are functionally equivalent to a protein comprising the amino acid sequence of SEQ ID NO: 2.

Specifically, for example, splicing variants of BST2 and mutants resulting from gene polymorphism of BST2 are included in the BST2 homologues. For example, the present inventors found splicing variants of cDNAs comprising the nucleotide sequence of SEQ ID NO: 1. The splicing variants were revealed to comprise the nucleotide sequences of SEQ ID NOs: 3 and 5, and to encode the amino acid sequences of SEQ ID NOs: 4 and 6, respectively.

In the present invention, BST2 comprises its splicing variants. All of these splicing variants are thus comprised in human BST2 or mouse BST2. Hereinafter, splicing variants are sometimes referred to as "subtypes".

Amino acid sequences may not change even when the nucleotide sequences comprise polymorphic alterations. Such nucleotide sequence mutations are called "silent mutations". Genes comprising nucleotide sequences with silent mutations are also comprised in the present invention. Herein, a polymorphism means that the nucleotide sequence of a certain gene differs between individuals in a population. In general, polymorphisms and mutations are genetically defined, based on the genotypic distribution rate. However, in the present invention, unless otherwise stated, both polymorphism and mutation are used as terms meaning that different nucleotide sequences exist, regardless of the distribution rate.

BST2 homologues comprise functionally equivalent proteins derived from species other than humans. Such proteins functionally equivalent to BST2 can be identified using hybridization, for example. Specifically, a polynucleotide encoding a BST2 such as that shown in SEQ ID NO: 1, or a fragment thereof, is used as a probe, and polynucleotides capable of hybridizing to the probe are isolated. Polynucleotides comprising highly homogenous nucleotide sequences are selected when such hybridization is carried out under stringent conditions, which increases the probability that the isolated proteins will comprise proteins functionally equivalent to BST2.

The present inventors confirmed that, like anti-human-protein antibodies, antibodies against mouse homologues of BST2 suppressed the activity of mouse IPCs. Mouse BST2 comprises the nucleotide sequence of SEQ ID NO: 9, encoding the amino acid sequence of SEQ ID NO: 10. Furthermore, in the same way, the present inventors also confirmed the existence of mouse homologue BST2H, which is a splicing variant of BST2. The nucleotide sequence of mouse BST2H is shown in SEQ ID NO: 7, and the amino acid sequence encoded by the nucleotide sequence is shown in SEQ ID NO: 8. Antibodies against mouse BST2H were also confirmed to suppress IPC activity.

The nucleotide and amino acid sequence information of the human and mouse BST2 and homologues thereof obtained in the present invention are summarized below.

|  | Nucleotide sequence | Amino acid sequence | Length of amino acid sequence |
|---|---|---|---|
| human BST2D | SEQ ID NO: 1 | SEQ ID NO: 2 | (180) |
| human BST2H | SEQ ID NO: 3 | SEQ ID NO: 4 | (158) |
| human BST2HS | SEQ ID NO: 5 | SEQ ID NO: 6 | (100) |
| mouse BST2H | SEQ ID NO: 7 | SEQ ID NO: 8 | (178) |
| mouse BST2D | SEQ ID NO: 9 | SEQ ID NO: 10 | (172) |
| mouse BST2HS | SEQ ID NO: 22 | SEQ ID NO: 23 | (105) |

Stringent conditions specifically include, for example, conditions of 6×SSC, 40% formamide, hybridization at 25° C., and washing with 1×SSC at 55° C. The stringency varies depending on conditions such as salt concentration, formamide concentration, and temperature. One skilled in the art can appropriately adjust these conditions so as to achieve the required stringency.

By using hybridization, for example, polynucleotides encoding a nonhuman homolog of BST2 can be isolated. BST2 homologs encoded by polynucleotides derived from nonhuman animals such as mice, rats, rabbits, pigs, or goats, constitute functionally equivalent proteins in the present invention.

Proteins encoded by polynucleotides isolated by the above hybridization techniques generally have a high amino acid sequence homology with human BST2D (SEQ ID NO: 2). "High homology" refers to a sequence identity of 30% or more, preferably 50% or more, and more preferably 80% or more (for example, 95% or more, 98% or more, or more preferably 99% or more). Nucleotide sequence or amino acid sequence identity can be examined by using an interne homology search site (for example, homology searches such as FASTA, BLAST, PSI-BLAST, and SSEARCH in the DNA Data Bank of Japan (DDBJ) can be used (for example, a homology search (Search and Analysis) page on the DNA Data Bank of Japan (DDBJ) website. In addition, searches using BLAST can be carried out at the National Center for Biotechnology Information (NCBI) (for example, the BLAST page on the NCBI website; Altschul, S. F. et al., J. Mol. Biol., 1990, 215(3):403-10; Altschul, S. F. & Gish, W., Meth. Enzymol., 1996, 266:460-480; Altschul, S. F. et al., Nucleic Acids Res., 1997, 25:3389-3402)].

For example, amino acid sequence identity can be calculated using Advanced BLAST 2.1 to determine an identity value (%) by using the blastp program with an expect value of 10; filters all set to OFF; using a BLOSUM62 matrix with gap existence cost, per residue gap cost, and lambda ratio set to 11, 1, and 0.85 (default values), respectively (Karlin, S, and S. F. Altschul (1990) Proc. Natl. Acad. Sci. USA 87:2264-68; Karlin, S, and S. F. Altschul (1993) Proc. Natl. Acad. Sci. USA 90:5873-7).

Furthermore, BST2 homologues can be discovered in other species by searching for the nucleotide sequence information of cDNAs or genomic DNAs whose structures have been already determined. Specifically, similar sequence information can be searched out using a homology search of databases with accumulated known nucleotide or amino acid sequence information, using as a query the nucleotide and/or amino acid sequence information of human BST2. Highly homogenous known genes and proteins derived from other species can be discovered by homology searches if they are present in the databases. Even when the full-length sequence of a gene has not yet been identified, if sequence information on fragments thereof, such as ESTs, is available, the full-length sequence of the gene may be constructed by in silico cloning. Such homologues derived from other species and thus identified can be used as BST2 homologues of the present invention if they can be confirmed to be actually expressed in IPCs of the animal species.

In the present invention, interferon-producing cells (IPCs) refer to cells that have the ability to produce IFNs and that express either or both of BST2 and its homologues on their cell surface. This includes cases where either or both of BST2 and its homologues are expressed along with activation of the cells. For example, preferred IPCs are human and mouse cells which are precursor cells of dendritic cells and which produce IFNs upon stimulation. Hereinafter, unless otherwise stated, IPCs comprise not only precursor cells of dendritic cells, but also cells that have the ability to produce IFNs and that express either or both of BST2 and its homologues on their cell surface. Methods for identifying such IPCs are known. For example, IPCs can be discriminated from other blood cell types using several cell surface markers as indicators. Specifically, a profile of cell surface markers for human IPCs is shown below (Shortman, K. and Liu, Y J. Nature Reviews 2: 151-161, 2002). Some recent reports define BDCA-2-positive cells as "IPCs" (Dzionek, A. et al. J. Immunol. 165: 6037-6046, 2000).

[Profile of Cell Surface Antigens in Human IPCs]
CD4-positive, CD 123-positive,
Lineage (CD3, CD14, CD16, CD19, CD20, CD56)-Negative, CD11c-Negative Thus, cells with these expression profiles for known markers and with the ability to produce IFNs can be regarded as IPCs. In addition, cells in the living body with the ability to produce IFNs are also comprised in IPCs, even when the cells belong to a cell group having a profile that differs from the above expression profile pattern.

Meanwhile, mouse IPCs are defined by the following profile:
[Profile of Cell Surface Antigens in Mouse IPCs]
CD11c-, B220-, Ly6C-, and CD45RB-positive
CD11b-, CD3-, and CD19-negative Furthermore, the following features are shared by human and mouse IPCs:
[Morphological Cell Features]
  similar to plasma cells
  a round cells with smooth surfaces
  relatively large nucleus
[Functional Cell Features]
  upon viral infection produce a large quantity of type 1 interferons in a short period
    differentiate into dendritic cells after viral infection In the present invention, "suppressing IPC activity" means suppressing at least one IPC function. IPC functions can include IFN production and cell survival. Cell survival is interchangeable with cell count. Thus, suppressing either or both of these functions is "suppressing IPC activity". Type 1 IFNs produced by IPCs have been shown to cause various diseases. Thus suppression of this production is useful as a therapeutic strategy for these diseases.

For example, relationships between IFNα and the pathological conditions of autoimmune diseases have been pointed out. IPCs produce the majority of IFNα. Therefore, suppression of this production can improve the pathological conditions caused by IFNα. In the present invention, the suppression of IFN production by IPCs means that the production of at least one type of IFN produced by IPCs is suppressed. Preferred IFNs of the present invention are type 1 IFNs. Of these, IFNα is important.

Specifically, the present invention relates to agents for suppressing IFN production, which comprise as active ingredients antibodies recognizing either or both of BST2 and its homologues. The present invention also provides methods for suppressing IFN production, which comprise the step of administering antibodies recognizing either or both of BST2 and its homologues. Furthermore, the present invention relates to uses of antibodies recognizing either or both of BST2 and its homologues in the production of pharmaceutical compositions for suppressing IFN production.

IPCs comprise small numbers of cells that produce large quantities of IFNs. For example, when stimulated with a virus, precursor cells of dendritic cells produce the majority of IFNs in vivo. The quantity of produced IFNs is reduced as a result of reducing the number of IPCs producing a large quantity of IFNs. Thus, the pathological conditions caused by IFNα can be improved by reducing the number of IPCs.

Antibodies used in the present invention, which recognize either or both of BST2 and its homologues, can be prepared by using as an antigen BST2 or its homologues, or fragments thereof. Such antibodies of the present invention may belong to any antibody class. In addition, there is no limitation on the animal species from which the antibodies are derived. Furthermore, fragments comprising an antigen-binding region of such antibodies may be used as such antibodies. For example, antibody fragments comprising an antigen-binding region produced by enzymatic digestion of an IgG can be used as the antibodies of the present invention. Specifically, antibody fragments such as Fab and F(ab')$_2$, can be prepared by papain or trypsin digestion. Such antibody fragments are known to be applicable as antibody molecules with binding affinity to antigens. Alternatively, antibodies constructed by genetic recombination can also be used, so long as they retain necessary antigen-binding activities. "Antibodies constructed by genetic recombination" include, for example, chimeric antibodies, CDR-transplanted antibodies, single-chain Fv, diabodies, linear antibodies, and multispecific antibodies formed from antibody fragments. Methods for preparing such antibodies using arbitrary antigens are known.

In the present invention, antibodies may be modified, if required. According to the present invention, antibodies that recognize either or both of BST2 and its homologues have the activity of reducing the number of IPCs. Specifically, the antibodies themselves are thought to be cytotoxic to IPCs. Subclasses of antibodies with strong effector activity are known. Alternatively, the effect of suppressing IPC activity can be further enhanced by modifying antibodies using cytotoxic agents. Such cytotoxic agents include the following substances:

Toxins: pseudomonas endotoxin (PE), diphtheria toxin, ricin

Radioisotopes: $Tc^{99m}$, $Sr^{89}$, $I^{131}$, $Y^{90}$

Anticancer agents: calicheamicin, mitomycin, paclitaxel

Toxins comprising proteins can be bound to antibodies, fragments thereof, or such using difunctional reagents. Alternatively, fusion proteins may be prepared by linking antibody-encoding genes with toxin-encoding genes. Methods for binding antibodies with radioisotopes are also known. For example, methods for labeling antibodies with radioisotopes using chelating agents are known. Furthermore, anticancer agents can be bound to antibodies using sugar chains or difunctional reagents.

The antibodies to be used in the present invention may have artificially altered structures. For example, various modification methods for improving cytotoxicity and stability of antibodies are known. Specifically, immunoglobulins having heavy chains with altered sugar chains are known (Shinkawa, T. et al. J. Biol. Chem. 278: 3466-3473.2003). Altering sugar chains enhances the antibody-dependent cell-mediated cytotoxicity (ADCC) of immunoglobulins. Immunoglobulins comprising Fc regions with altered amino acid sequences are also known. Specifically, ADCC is enhanced by artificially increasing the binding activity of immunoglobulins to Fc receptors (Shield, R L. et al. J. Biol. Chem. 276; 6591-6604, 2001).

Once bound to an Fc receptor, IgG is incorporated into cells. Next, the IgG binds to Fc receptors expressed in endosomes, then is again released into the blood in an identified phenomenon. The probability that IgG is again released into the blood after incorporation into cells is increased when its binding activity to Fc receptor is stronger. As a result, retention time of IgG in the blood is prolonged (Hinton, P R. et al. J Biol. Chem. 279: 6213-6216, 2004). In addition, alterations to the amino acid sequence of the Fc region may result in changes in complement-dependent cytotoxicity (CDC) activity. Such altered antibodies can be used as antibodies of the present invention.

For example, monoclonal antibodies can be collected from antibody-producing cells that produce the monoclonal antibodies. Cells producing monoclonal antibodies usable in the present invention can be obtained by administering animals to be immunized with BST2 or its homologues, or fragments thereof, or cells producing the same, or cell membrane fractions thereof, as an immunogen; and then cloning the antibody-producing cells. Specifically, the present invention provides methods for producing antibodies that suppress IPC activities, which comprise the steps of:

(1) administering BST2 or its homologues as antigens to animals to be immunized;

(2) selecting antibody-producing cells that produce antibodies which recognize BST2 from the antibody-producing cells of the immunized animals prepared in (1);

(3) culturing the antibody-producing cells selected in (2), or isolating genes encoding the antibodies produced in the antibody-producing cells, and culturing cells carrying and capable of expressing these genes; and
(4) collecting antibodies that suppress the activity of interferon-producing cells from the culture of (3).

In standard methods for producing monoclonal antibodies, hybridomas prepared by fusing immunocytes and tumor cells are used as antibody-producing cells. Immunogens that can be used in the present invention are BST2 or its homologues, or fragments thereof. Such immunogens can be purified from cells transformed with the genes encoding these immunogens. Alternatively, cells expressing BST2 or its homologues can be used as immunogens. Specifically, such cells can include the cells described below. Cell membrane fractions of these cells can also be used as immunogens.

IPCs collected from living bodies
IPCs obtained by inducing differentiation from hematopoietic stem cells or such
Cells carrying and capable of expressing an exogenous gene for a BST2 or a homologue thereof.

To collect IPCs from living bodies, for example, target cells can be collected based on expression profiles of cell surface markers, as described above. Methods for collecting particular cells using multiple cell surface markers as indicators are known. Cells exhibiting a desired expression profile can be readily fractionated, for example, by using immunostaining and cell sorting. For example, human IPCs are enriched by selecting BDCA-2-positive cells. Such IPCs collected from humans are used as immunogens after the cells are activated, if required.

IPCs may not only be derived from peripheral blood or hematopoietic tissues of living animals, but may also be obtained as cultured cells. IPCs can be prepared on a large scale, for example, by culturing human or mouse hematopoietic stem cells and differentiating the cells. Conditions for differentiating human and mouse hematopoietic stem cells into IPCs in vitro are known.

For example, there are reports of in vitro IPC derivation from hematopoietic stem cells in humans (Blom, B. et al. J. Exp. Med. 192: 1785-1796, 2000; Chen, W. et al. Blood 103: 2547-2553, 2004) and mice (Gilliert et al 2002, J. Exp. Med. 958-953). The in vivo derivation of mouse IPCs is also known (Bjorck et al., Blood 2001, 3520-3526). IPCs differentiated in vitro are advantageous as immunogens for preparing monoclonal antibodies that recognize IPCs.

Specifically, differentiation into IPCs is induced by culturing a population of cells comprising hematopoietic stem cells in the presence of an IPC inducer. Bone marrow cells can be used as cell populations comprising hematopoietic stem cells, for example. FLT-3 ligand or a combination of FLT-3 ligand and thrombopoietin (TPO) can be used as IPC inducers. The concentration of FLT-3 ligand in the culture medium is typically 1 to 100 ng/ml. Other culture conditions may correspond to those for standard blood cell cultures. Specifically, RPMI1640 or the like may be used as a basal medium, and can be supplemented with about 10% fetal calf serum. Alternatively, Yssel's medium was used to derive human IPCs. In vitro differentiation into human IPCs peaks at about 25 days, for example.

IPCs for immunogens can be prepared by obtaining IPCs differentiated from cultured hematopoietic stem cells. In practice, cells with cell surface antigens characteristic to IPCs are fractionated using several cell surface markers. Specifically, for example, BDCA-2-positive cells can be obtained as human IPCs. Alternatively, mouse IPCs can be yielded by using a cell sorter to fractionate cell fractions that are CD11c-positive, B220-positive and CD11b-negative.

Alternatively, IPCs can be fractionated as cells that react to antibodies already shown to be IPC-specific. Monoclonal antibodies that recognize mouse IPC-specific antigens, produced by monoclonal antibody-producing 2E6 cells (WO 2004/013325; FERM-BP-8445) and established by the present inventors, can be used to fractionate mouse IPCs.

IPCs can be fractionated from peripheral blood. However, as described above, the IPC population in peripheral blood is extremely small, and therefore large quantities of peripheral blood are required to collect IPCs. It is thus advantageous to use IPCs yielded by differentiating from hematopoietic stem cells as immunogens.

When preparing monoclonal antibodies for use in the present invention, it is not only possible to use IPCs as immunogens, but also to use proteins comprising an amino acid sequence selected from the group consisting of SEQ ID NOs: 2, 4, and 6, or fragments thereof. The monoclonal antibodies of the present invention were found to recognize as antigens those proteins comprising an amino acid sequence selected from the group consisting of SEQ ID NOs: 2, 4, and 6. Thus, the monoclonal antibodies of the present invention can be prepared using these proteins as immunogens.

Proteins comprising an amino acid sequence selected from the group consisting of SEQ ID NOs: 2, 4, and 6 may be prepared as recombinant proteins. For example, the nucleotide sequence of SEQ ID NO: 1 encodes the amino acid sequence of SEQ ID NO: 2. Further, the nucleotide sequence of SEQ ID NO: 3 encodes the amino acid sequence of SEQ ID NO: 4. Thus, desired proteins can be obtained by expressing DNAs comprising any of these nucleotide sequences by using appropriate hosts and vectors.

Alternatively, oligopeptides that comprise a consecutive amino acid sequence selected from an amino acid sequence selected from the group consisting of SEQ ID NOs: 2, 4, and 6 can also be used as immunogens. Amino acid sequences that should be selected as immunogens comprise, for example, about five to 50 amino acids, and preferably about seven to 20 amino acids. Methods for preparing oligopeptides comprising arbitrary amino acid sequences are known. Oligopeptides comprising a desired amino acid sequence can be prepared, for example, by chemically linking amino acids. Alternatively, fragments comprising a particular amino acid sequence can also be obtained by cleaving recombinant proteins comprising the full-length amino acid sequence, prepared as described above. The immunogenicity of the yielded oligopeptides can be increased by binding them with appropriate carrier proteins. Keyhole limpet hemocyanin, bovine serum albumin and such can be used as carrier proteins.

The majority of the amino acid sequences of SEQ ID NOs: 2, 4, and 6 are identical. Therefore, monoclonal antibodies that recognize all of these proteins can be prepared by using an amino acid sequence selected from the shared amino acid sequences. Such antibodies can act on cells expressing any of the subtypes and regulate their activities. In fact, the Examples confirm that antibody 3G7#6, which binds to all subtypes, regulates IPC activity.

Furthermore, two particular proteins can be discriminated from the other among three types of proteins by using an amino acid sequence shared by the two types. Alternatively, monoclonal antibodies capable of specifically recognizing each protein can also be prepared by using amino acid sequences unique to the each of the amino acid sequences. For example, the amino acid sequence of SEQ ID NO: 4 from position 139 to 158 from the N terminus is unique to SEQ ID NO: 4. Likewise, the amino acid sequence of SEQ ID NO: 6 from position 96 to 100 from the N terminus is unique to SEQ ID NO: 6. Antibodies recognizing epitopes comprising such amino acid sequences can act on cells expressing the subtypes recognized by the antibodies, and thus regulate the activity of the cells. As shown in the Examples, antibody 3D3#7, specific to SEQ ID NO: 4 (hBST2H), was indeed found to regulate IPC activity.

As a next step for preparing monoclonal antibodies, appropriate animals are immunized with immunogens. IPCs can be administered to the animals to be immunized along with an appropriate adjuvant. Alternatively, any protein selected from the group consisting of SEQ ID NOs: 2, 4, and 6, or a peptide comprising a partial amino acid sequence thereof, can be administered to animals to be immunized along with an adjuvant.

Furthermore, transformed cells carrying and capable of expressing DNAs encoding an amino acid sequence selected from the group consisting of SEQ ID NOs: 2, 4, and 6 can also be used as immunogens. For example, DNAs comprising a nucleotide sequence constituting the coding region of a nucleotide sequence selected from the group consisting of SEQ ID NOs: 1, 3, and 5 are preferred as the DNAs described above. Transformed cells useful as immunogens can be yielded by inserting such DNAs into appropriate expression vectors and transforming host cells with the constructs.

Such host cells for use as immunogens may be derived from the same animal species as the animals to be immunized. Immune responses specific to the foreign protein can be induced by using cells from the same species. For example, when rats are used as the animals to be immunized, it is advantageous to use rat-derived host cells. Fractions of transformed cells comprising the above proteins can also be used as immune animals. As shown in the Examples, transmembrane domains are found in amino acid sequences selected from the group consisting of SEQ ID NOs: 2, 4, and 6 (transmembrane regions shown in FIG. 8). Thus, proteins comprising these amino acid sequences may be expressed on cell membranes. When proteins comprising the amino acid sequences of SEQ ID NOs: 8 and 10 were expressed in COS cells, more proteins were indeed detected in precipitated fractions of the cultured transformants. Thus, cell membrane fractions of cells expressing the above proteins can be used as immunogens.

Any nonhuman vertebrates that recognize IPCs as foreign materials can be used as the animals to be immunized according to the present invention. When preparing monoclonal antibodies, animals for which fusion partners for hybridomas can be easily obtained are advantageous. For example, hybridomas have been established using cells derived from mice, rats, rabbits, cows, goats, and such. Such animals can be used for immunization in the present invention. Adjuvants include, for example, Freund's complete and incomplete adjuvants.

Animals are immunized multiple times at three to ten day intervals. The number of IPCs used in each immunization is arbitrary. Typically, $10^3$ to $10^8$ IPCs, for example, $10^6$ IPCs, are used in each immunization. Alternatively, for immunization using proteins or peptides, 1 μg to 100 μg is generally used. Monoclonal antibodies of the present invention can be yielded by collecting immunocompetent cells from animals immunized multiple times and then cloning cells that produce desired antibodies. Immunocompetent cells refer to cells with the ability to produce antibodies in immune animals.

Such immunocompetent cells can be cloned, for example, by hybridoma methods. A single immunocompetent cell produces a single type of antibody. Therefore, monoclonal antibodies can be prepared when a cell population derived from a single cell can be established (cloned). Hybridoma methods refer to methods that comprise immortalization of immunocompetent cells by fusion with an appropriate cell line, followed by cloning. Many cell lines useful in the hybridoma method are known. Such cell lines have superior immortalization efficiency for lymphocytic cells, and comprise various genetic markers required for selection of cells that succeeded in cell fusion. Furthermore, when aiming to obtain antibody-producing cells, cell lines lacking antibody-producing ability can be used.

For example, mouse myeloma P3x63Ag8.653 (ATCC CRL-1580) is a commonly used cell line useful in cell fusion methods for mice and rat cells. Since mice IPCs are used as immunogens in the present invention, the animals to be immunized are animals other than mice. Hybridomas are generally prepared by fusing cells from the same species; however, monoclonal antibodies can also be obtained from hetero-hybridomas between related but different species.

Specific protocols for cell fusion are known. Specifically, immunocompetent cells from immune animals are combined with appropriate fusion partners to achieve cell fusion. The immunocompetent cells include spleen cells and peripheral blood B cells. Various cell lines, described above, can be used as fusion partners. The polyethylene glycol method and the electrofusion method can be used to achieve cell fusion.

Next, cells that succeeded in cell fusion are selected using selection markers comprised by the fused cells. For example, when using HAT-sensitive cell lines for cell fusion, cells that succeeded in cell fusion are selected by selecting cells that can grow in HAT medium. The antibodies produced by selected cells are then confirmed to have the desired reactivity.

Each hybridoma is screened based on antibody reactivity. Specifically, hybridomas producing antibodies that bind to either or both of BST2 and its homologues are selected. Preferably, when selected hybridomas are subcloned and finally confirmed to produce desired antibodies, they are selected as hybridomas that produce the monoclonal antibodies of the present invention.

Specifically, such screening can be performed, for example, using as an antigen proteins comprising an amino acid sequence selected from the group consisting of SEQ ID NOs: 2, 4, and 6, or peptides comprising a partial amino acid sequence thereof. The antigens are immobilized onto appropriate solid phases, and monoclonal antibodies that bind to the antigens can be detected by using labeled antibodies that recognize the immunoglobulins of immune animals. Monoclonal antibodies can be rapidly screened by ELISA using enzyme-labeled antibodies and microplates in which antigens are bound to the inner wall. When a monoclonal antibody has been confirmed to have the binding activity to an antigen, its actual influence on IPC activity can be determined as required. Influences on IPCs can be confirmed, for example, by the methods described below.

Such monoclonal antibodies can be expressed by obtaining cDNAs encoding the antigen-binding regions of the antibodies from hybridomas, and inserting them into appropriate expression vectors. Techniques for obtaining cDNAs encoding antibody variable regions and expressing them in appropriate host cells are known. Techniques for producing chimeric antibodies by linking a constant region with a variable region comprising an antigen-binding region are also known.

Furthermore, the antigen-binding activity of a monoclonal antibody can be transferred to other immunoglobulins. Antigen-binding regions in immunoglobulins are constituted by complementarity determining regions (CDRs) and frame regions. The antigen-binding specificity of each immunoglobulin is determined by its CDR, and the frame maintains the structure of the antigen-binding region. CDR amino acid sequences are extremely diverse, while frame region amino acid sequences are highly conserved. Antigen-binding activity can also be transferred by inserting the CDR antigen into the frame region of another immunoglobulin molecule. Methods for transferring the antigen binding specificity of nonhuman immunoglobulins into human immunoglobulins using the above methods have been established.

Any monoclonal antibody prepared as described above can be used in the present invention. Specifically, in the present invention, it is possible to use monoclonal antibodies which comprise immunoglobulins comprising antigen-binding regions encoded by polynucleotides derived from cDNAs that encode the antigen-binding regions of such monoclonal antibodies.

Hybridomas producing monoclonal antibodies that can be used in the present invention include, for example, hybridomas 3D3#7 and 3G7#6. Hybridomas 3D3#7 and 3G7#6 were deposited under accession numbers FERM BP-10339 and FERM BP-10340 on May 27, 2005 in the International Patent Organism Depositary, National Institute of Advanced Industrial Science and Technology. The deposition is specified by the following description:
(a) Name and Address of Depositary Institution
  Name: International Patent Organism Depositary, National Institute of Advanced Industrial Science and Technology
  Address: Tsukuba Central 6, 1-1-1 Higashi, Tsukuba, Ibaraki, Japan (Zip code: 305-8566)
(b) Date of Deposition: May 27, 2005
(c) Accession Number: BP-10339 (hybridoma 3D3#7)
(c) Accession Number: BP-10340 (hybridoma 3G7#6)

These deposits were made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The hybridomas will be made available by the National Institute of Advanced Industrial Science and Technology under the terms of the Budapest Treaty, which assures permanent and unrestricted availability of the progeny of the culture to the public upon issuance of the pertinent U.S. patent.

The assignee of the present application has agreed that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

Monoclonal antibodies for use in the present invention can be collected from cultures of hybridomas producing these monoclonal antibodies. Hybridomas may be cultured in vitro or in vivo. Hybridomas can be cultured in vitro using known culture medium such as RPMI1640. Immunoglobulins secreted from such hybridomas are accumulated in culture supernatants. Thus, monoclonal antibodies of the present invention can be prepared by collecting such culture supernatants, then purifying as required. Immunoglobulins can be purified more simply when serum-free media are used. However, media can be supplemented with about 10% fetal calf serum for rapid growth of hybridomas and enhanced antibody production.

Hybridomas can also be cultured in vivo. Specifically, by inoculating hybridomas into the peritoneal cavity of nude mice, hybridomas can be cultured in peritoneal cavities. Monoclonal antibodies are accumulated in ascites. Thus, desired monoclonal antibodies can be obtained by collecting ascites, then purifying as required. The yielded monoclonal antibodies may be modified or processed appropriately for each purpose.

When contacted with IPCs, antibodies which bind to either or both of BST2 and its homologues suppress IPC activity. Thus, such antibodies can be used as agents or methods for suppressing IPC activity. Specifically, the present invention provides agents for suppressing IPC activity which comprise as an active ingredient at least one component selected from the group consisting of (a) to (c), shown below. The present invention also relates to methods for suppressing IPC activity, which comprise the step of administering at least one component selected from the group consisting of (a) to (c), shown below. Furthermore, the present invention relates to uses of at least one component selected from the group consisting of (a) to (c), shown below, in the production of agents for regulating IPC activity.

(a) antibodies which bind to either or both of BST2 and its homologues, or fragments that comprise an antigen-binding domain thereof;

(b) immunoglobulins transplanted with a complementarity determining region of an antibody of (a), or fragments comprising an antigen-binding region thereof; and (c) polynucleotides encoding the components described in (a) or (b).

In the present invention, the monoclonal antibodies that suppress IPC activity include monoclonal antibodies that recognize the protein comprising an amino acid sequence selected from the group consisting of SEQ ID NOs: 2, 4, and 6. One or more types of monoclonal antibodies can be used in the present invention. For example, two or more types of monoclonal antibodies that recognize a particular BST2 or subtypes thereof can be combined and used in the present invention. Alternatively, two or more types of monoclonal antibodies that recognize different types of BST2 or subtypes thereof can be used in combination.

An antibody's activity in suppressing the IFN-producing activity of IPCs can be confirmed as follows: IPCs produce a large quantity of IFNs upon viral stimulation. The antibodies are added before, after, or at the same time as viral stimulation of IPCs, and the IFN-producing ability of these IPCs is compared with that of IPCs in the absence of antibodies. IFN-producing ability can be evaluated by assaying the IFNα, IFNβ, and such comprised in IPC culture supernatants. When such a comparison reveals that addition of an antibody significantly reduced the IFN level in the supernatant, the tested antibody is demonstrated to have the activity of suppressing IFN-producing activity. Such methods for assaying IFNs are known. IPCs produce the majority of IFNs in vivo. Thus, in vivo IFN production can be regulated by suppressing the ability of IPCs to produce IFNs.

In the present invention, IPC activity comprises maintenance of the number of IPCs. Thus, in the present invention, suppression of IPC activity comprises reducing the number of IPCs. Like IFN production, IPC activation is induced upon stimulation with an infectious virus or such. When the number of activated IPCs is confirmed to be reduced in the presence of an antibody, that antibody is shown to suppress IPC activity. As a control, an inactive immunoglobulin derived from the same animal species as that from which the antibody tested for activity is derived can be used, as in IFN production. The number of IPCs can be compared quantitatively by counting cells. Cells can be counted using a FACS or microscope.

IPCs are also said to differentiate into dendritic cells 2 (DC2s), which are cells that derive Th2, as a result of viral infection or such. Differentiation into Th2 can be suppressed if the viral stimulation-induced IFN production by IPCs can be suppressed. Thus, the monoclonal antibodies of the present invention that suppress IFN production are expected to have therapeutic effects on various allergic diseases.

When an antibody recognizing either or both of BST2 and its homologues is administered to hosts that are heterologous to the species from which the antibody was derived, the antibody is preferably processed into a form hardly recognized as foreign material by the hosts. For example, when processed into the molecules described below, an immunoglobulin is hardly recognized as foreign material. Techniques for processing immunoglobulin molecules as described below are known.

- fragments comprising an antigen-binding region that lacks a constant region (Monoclonal Antibodies: Principles and Practice, third edition, Academic Press Limited. 1995; Antibody Engineering, A Practical Approach, IRL PRESS, 1996)
- chimeric antibodies composed of an antigen-binding region of a monoclonal antibody and a constant region of a host immunoglobulin (Experimental Manual for Gene Expression, Kodansha 1994 (eds., I. Ishida and T. Ando))
- CDR-substituted antibodies in which a complementarity determining region (CDR) of a host immunoglobulin has been replaced with a CDR of a monoclonal antibody (Experimental Manual for Gene Expression, Kodansha 1994 (eds., I. Ishida and T. Ando))

Alternatively, human antibodies can be obtained from non-human immune animals introduced with human antibody genes. For example, transgenic mice introduced with human antibody genes are in practical use as immune animals for producing human antibodies (Ishida et al., Cloning and Stem Cells, 4: 85-95, 2002). Human antibodies recognizing BST2 can be prepared by using such animals with human BST2 as an antigen. Human antibodies are preferably administered to humans.

In addition, genes for the variable regions of human immunoglobulins can be obtained by the phage display method (McCafferty J. et al., Nature 348: 552-554, 1990; Kretzschmar T. et al., Curr Opin Biotechnol. 2002 December; 13(6):598-602). The phage display method comprises integrating genes encoding the variable regions of human immunoglobulins into phage genes. Phage libraries can be prepared using various immunoglobulin genes as a source. Such variable regions are expressed as fusion proteins with proteins constituting phages. The variable regions expressed on phage surfaces by phages retain antigen-binding activity. Thus, phages expressing variable regions with desired binding activity can be screened from phage libraries by selecting phages that bind to antigens, cells expressing antigens, or the like. Furthermore, phage particles selected in this way carry genes that encode variable regions with desired binding activity. Specifically, genes encoding variable regions with desired binding activity can be obtained by the phage display method, using the variable region binding activity as an indicator.

In the present invention, when an antibody recognizing BST2, its homologues, or both, or fragments thereof, is used as an agent for suppressing IPC activity, or is used in the methods for suppressing IPC activity, it may be administered in the form of a protein or polynucleotide encoding the same. When administering such polynucleotides, it is preferable to use a vector carrying a polynucleotide encoding a target protein under the control of an appropriate promotor, such that the target protein can be expressed. Enhancers and terminators may also be arranged in the vector. Vectors that carry genes for the heavy and light chains constituting an immunoglobulin and allow expression of an immunoglobulin molecule are known.

Vectors that can express immunoglobulins can be administered by their introduction to cells. When administered to living bodies, vectors that can infect cells when administered to living bodies may be administered as is. Alternatively, lymphocytes isolated from living bodies may be introduced with such vectors and then returned to the body (ex vivo).

In the agents or methods for suppressing IPC activity of the present invention, the dose of monoclonal antibodies to be administered to a living body is typically 0.5 mg to 100 mg immunoglobulin/kg weight, for example, 1 mg to 50 mg immunoglobulin/kg weight, and preferably 2 mg to 10 mg immunoglobulin/kg weight. The intervals between administration of antibodies to a living body can be appropriately regulated so that an effective in vivo concentration of immunoglobulin is maintained during the treatment. Specifically, administration can be at one to two week intervals, for example. The administration route is arbitrary. Those skilled in the art can appropriately select effective administration routes for treatment. Specifically, administration can be oral or parenteral. For example, antibodies may be administered systemically or locally, by intravenous, intramuscular, intraperitoneal, or subcutaneous injections, or such. In the present invention, preparations suited to parenteral administration include injections, suppositories, and sprays. Alternatively, when added to cells, the immunoglobulins are typically added to culture media at a concentration of 1 µg/ml, preferably at 10 µg/ml or higher, more preferably at 50 µg/ml or higher, and still more preferably at 0.5 mg/ml or higher.

In the agents or methods of the present invention for suppressing IPC activity, monoclonal antibodies can be administered to the living body by any method. The monoclonal antibodies are generally formulated in combination with pharmaceutically acceptable carriers. The monoclonal antibodies may be combined with additives such as thickeners, stabilizers, preservatives, and solubilizing agents, if required. Such carriers or additives include lactose, citric acid, stearic acid, magnesium stearate, sucrose, starch, talc, gelatin, agar, vegetable oils, and ethylene glycol. The phrase "pharmaceutically acceptable" means being approved by supervisory authorities of the government in each country, or described in terms of its use for animals, mammals, and in particular humans, in Pharmacopoeia in each country or generally known Pharmacopoeia. Such agents of the present invention for suppressing IPC activity may also be provided in the form of single- or multiple-dose freeze-dried powders or tablets. Such freeze-dried powders or tablets may be combined with sterile water, physiological saline, or buffers for injection that are used to dissolve the composition to a desired concentration before administration.

Furthermore, when administering expression vectors for immunoglobulins, plasmids separately carrying the heavy chain and the light chain can be cotransfected at a dose of 0.1 to 10 mg/kg weight (for each plasmid), for example, 1 to 5 mg/kg weight. Such vectors can also be introduced into cells in vitro at a dose of 1 to 5 µg/$10^6$ cells.

Expression of BST2 or its splicing variants in IPCs was demonstrated to increase along with IPC activation. The expression of BST2 or its splicing variants is almost undetectable in non-activated human IPCs. Mouse BST2 is expressed in IPCs even before activation, and its expression level increases with IPC activation. Thus, BST2 or its splicing variants are useful as markers for IPC activation. Specifically, the present invention relates to methods for detecting activated IPCs, which comprise the step of detecting an indicator substance of the following (a) to (d):
(a) polynucleotides comprising a nucleotide sequence selected from the group consisting of SEQ ID NOs: 1, 3, and 5;
(b) polynucleotides comprising a consecutive nucleotide sequence selected from a nucleotide sequence selected from the group consisting of SEQ ID NOs: 1, 3, and 5;
(c) proteins comprising an amino acid sequence selected from the group consisting of SEQ ID NOs: 2, 4, and 6; and
(d) proteins comprising a consecutive amino acid sequence selected from an amino acid sequence selected from the group consisting of SEQ ID NOs: 2, 4, and 6.

The activation markers can be detected using the presence of the proteins or mRNAs encoding the proteins. Such proteins and mRNAs may be full-length or partial sequences. When using partial sequences as detection targets, the selected targets for detection are preferably sequences long enough to ensure specificity. For example, mRNAs comprising a consecutive nucleotide sequence of generally 10 b or more, and preferably 15 b or more, for example, about 15 b to 500 b, can be such detection targets.

Methods for detecting the above indicator substances are known. For example, polynucleotides such as indicator substances (a) or (b) can be detected based on hybridization, using oligonucleotides comprising a nucleotide sequence complementary to each nucleotide sequence. Meanwhile, proteins such as proteins (c) or (d) can be immunologically detected using antibodies recognizing these protein.

In the present invention, the phrase "detection of activated IPCs" means that cells constituting samples are confirmed to comprise IPCs activated by some stimulation. By detecting activated IPCs using the present invention, IPCs in the living bodies or tissues from which the sample is derived can be shown to be activated. The level of IPC activation in vivo can also be determined using the methods of the present invention. Specifically, the present invention relates to methods for determining the level of IPC activation in vivo, which comprise the steps of:
(1) detecting either or both of cells expressing an indicator substance of (a) to (d), and the expression level of the substance, in interferon-producing cells comprised in samples collected from a living body:
    (a) polynucleotides comprising a nucleotide sequence selected from the group consisting of SEQ ID NOs: 1, 3, and 5;
    (b) polynucleotides comprising a consecutive nucleotide sequence selected from a nucleotide sequence selected from the group consisting of SEQ ID NOs: 1, 3, and 5;
    (c) proteins comprising an amino acid sequence selected from the group consisting of SEQ ID NOs: 2, 4, and 6; and
    (d) proteins comprising a consecutive amino acid sequence selected from an amino acid sequence selected from the group consisting of SEQ ID NOs: 2, 4, and 6; and (2) relating either or both of the number of cells and expression level determined in (1) to the activation level of interferon-producing cells in a subject.

In the present invention, any samples that may comprise IPCs can be used as the samples collected from a living body. Representative samples include body fluids, skin, synovial tissue, hematopoietic tissue, pus, alveolar lavage fluid, and other biopsy samples that can comprise blood cells. The body fluids include blood, spinal fluid, synovial fluid, urine, lacrimal fluid, saliva, and nasal discharge. Hematopoietic tissues include bone marrow and spleen. Alternatively, peripheral blood can be also used as a sample. The number of activated IPCs can be determined by detecting cells expressing any of the markers described above in the above tissues. When the ratio of the number of activated IPCs to the total number of IPCs is determined, the level of IPC activation in vivo can be related to the number of cells in which the above markers are detected. Markers that also allow detection of non-activated IPCs can be used to determine the ratio between the two. Such markers include, for example, BDCA2 and BDCA4. The total number of IPCs can be determined by counting cells expressing these markers. Thus, for example, the ratio of [number of BDCA2-positive cells]:[number of cells positive for BST2 or its splicing variants], represents the ratio of activated IPCs to IPCs. The greater the ratio of activated IPCs, the greater the level of IPC activation in a subject.

Alternatively, the expression levels of the above indicator substances detected in biological samples may be related to the activation level of interferon-producing cells in subjects. For example, expression of the above indicator substances is almost undetectable in human non-activated IPCs. Therefore, expression levels of the above indicator substances can correlate directly to the level of IPC activation. Thus, when expression levels of the above indicator substances are higher in biological samples, the level of IPC activation in those biological samples from the subject is elevated. In other words, increased IPC activation levels in biological samples are detected based on increases in the expression levels of indicator substances. The expression levels of indicator substances are determined depending on the activation level of each IPC and the number of activated IPCs. However, it is not necessary to evaluate the two independently, and the level of IPC activation can be evaluated based on the overall expression levels of indicator substances. In humans in particular, the expression of the above indicator substances is undetectable in inactive IPCs; the level of IPC activation can thus be evaluated based only on the expression level of indicator substances, without determining the number of positive (or negative) cells for indicator substances.

IPCs are important cells that support the immune system in vivo, through producing IFNs and the like. Thus knowing whether IPCs are activated is clinically important. For example, when activated IPCs or an increased level of IPC activation in a subject is confirmed according to the present invention, the subject's immune system is confirmed to be in an activated state. Specifically, autoimmune diseases, viral infections, and such can be suspected.

For example, IPC accumulations have been reported in the skin lesions of patients with systemic lupus erythematosus (Farkas, L. et al. Am. J. Pathol. 159: 237-243, 2001). Further, IPCs have been found to be increased in the synovial fluid of spondylarthrosis patients (Van Krinks. C. H. et al. Rheumatology, 43: 453-460, 2004). By determining the expression levels of the above indicator substances in such biological samples, information for evaluating the degree of autoimmune symptoms can be obtained.

The type of cytokine whose production is induced upon viral infection is known to sometimes vary depending on the type of virus (Dalod, M. et al. J. Exp. Med. 195: 517-528, 2002). Thus, when the types of virus that particularly stimulate IPC activation are identified in advance by the methods of the present invention, IPC activation can be used as a diagnostic material for identifying the type of virus that is the source of infection.

Specifically, the present invention relates to methods for detecting autoimmune diseases or viral infections, which comprise the steps of:

(1) determining either or both of cells expressing an indicator substance of (a) to (d) below, and the expression level of an indicator substance of the above (a) to (d) in biological samples; and (2) relating either or both of the number of cells and the expression level determined in (1) with an autoimmune disease or viral infection:

(a) polynucleotides comprising a nucleotide sequence selected from the group consisting of SEQ ID NOs: 1, 3, and 5;

(b) polynucleotides comprising a consecutive nucleotide sequence selected from a nucleotide sequence selected from the group consisting of SEQ ID NOs: 1, 3, and 5;

(c) proteins comprising an amino acid sequence selected from the group consisting of SEQ ID NOs: 2, 4, and 6; and (d) proteins comprising a consecutive amino acid sequence selected from an amino acid sequence selected from the group consisting of SEQ ID NOs: 2, 4, and 6.

In the present invention, autoimmune diseases or viral infections are detected when the number of cells or expression level determined in (1) is higher than that of a control. In the present invention, the determined results for healthy subjects can be used as controls. Alternatively, changes in the symptoms of autoimmune diseases or viral infections in subjects can be monitored by repeatedly performing the detection methods of the present invention for these subjects.

The detection methods of the present invention or the methods of the present invention for determining activation levels can be conducted, for example, as follows:

Samples comprising cells are contacted with monoclonal antibodies, and antibodies that bind with the above markers are bound to the IPCs in samples. The cell samples and antibodies are contacted under conditions that can maintain the immunological binding activity of the antibodies. Specifically, contact is preferably at a weakly acidic to weakly basic pH and a salt concentration close to that of physiological saline. Any samples that can comprise IPCs can be used as the samples. For example, lymphocyte populations in peripheral blood, or lymphocytic tissues in lymph nodes, the spleen, and such can be used as the samples. Methods for preparing such cell samples are known. Alternatively, IPCs differentiated from hematopoietic stem cells can be used as cell samples. Methods for differentiating cell populations comprising hematopoietic stem cells into IPCs in vitro or in vivo are known. Detection or identification of IPCs artificially differentiated is beneficial in searching conditions required for IPC differentiation.

Next, antibodies bound to cells are detected. Activated IPCs can be detected, for example, by labeling anti-BST2 antibodies and monitoring the label. Methods for labeling antibodies are known. Antibodies can be labeled, for example, with components such as enzymes, fluorescent substances, luminescent substances, substances with binding affinity, micro-beads, and radioisotopes. Methods for binding such components with antibodies are also known. Enzymes, fluorescent substances, micro-beads, or the like can be bound directly to antibodies using, for example, difunctional reagents such as maleimide derivatives. Alternatively, antibodies can be physically adsorbed onto the surface of micro-beads.

Alternatively, antibodies may be bound onto appropriate solid phases. Such solid phases include the inner walls of plates, tubes, columns, and capillaries, and the surfaces of bead-shaped solid phases.

The antibodies of the present invention can also be labeled indirectly. For example, rat-derived antibodies can be labeled indirectly using labeled antibodies that recognize rat immunoglobulins. Labeled antibodies for indirectly labeling antibodies are generally called secondary antibodies.

When using the methods of the present invention for detecting activated IPCs or the level of IPC activation, labels on antibodies can be monitored using techniques corresponding to each labeling component. For example, when the label is a fluorescent substance, fluorescence can be detected by emitting excitation light. When the label is an enzyme, the label can be monitored using a product in the enzyme reaction as an indicator.

Cells reacted with the antibodies may be separated prior to label detection. Antibodies that recognize different cell surface antigens can be used to separate such cells. Specifically, antibodies against the above markers are used in combination with arbitrary IPC-recognizing antibodies. For example, IPCs are specifically captured by contacting a cell population with IPC-specific antibodies that are immobilized onto beads. Then, the arbitrary IPC-recognizing antibodies are allowed to bind to the captured IPCs. Activated IPCs can be detected using labeled antibodies as the IPC-recognizing antibodies.

Antibodies that bind to either or both of BST2 and its splicing variants can be used as reagents for detecting activated IPCs. Kits for determining the level of IPC activation in subjects can be provided by combining reagents of the present invention for detecting activated IPCs, with the reagents for detecting IPCs. The reagents of the present invention for detecting IPCs refer to reagents capable of detecting IPCs regardless of their degree of activation. Such reagents for detecting IPCs include, for example, antibodies recognizing BDCA2 or BDCA4. The antibodies for the reagents of the present invention for detecting activated IPCs and detecting IPCs may be prelabeled with the above labeling components. Alternatively, the antibodies may be supplied in combination with secondary antibodies. The antibodies used in these reagents can be arbitrary fragments comprising the antigen-binding regions of the antibodies. Thus, not only complete immunoglobulin molecules but also fragments with the antigen-binding activity of immunoglobulins can be used. Such fragments include, for example, F(ab)2 and Fab.

The detection methods of the present invention can be conducted, for example, as described below: Specifically, when targeting mRNAs comprised in cell samples, the above indicators (a) or (b) are detected. Preferable indicators particularly include mRNAs and cDNAs derived from mRNAs. The indicators (a) or (b) can be detected using oligonucleotides comprising nucleotide sequences complementary to consecutive nucleotide sequences selected from a nucleotide sequence selected from the group consisting of SEQ ID NOs: 1, 3, and 5. Such oligonucleotides are DNAs, RNAs, and derivatives thereof, whose lengths are, for example, 10 b to 50 b, and preferably 15 b to 30 b. Such DNAs can be chemically synthesized. Such DNAs can be prepared as DNA derivatives when synthesized using fluorescent derivatives.

Oligonucleotides hybridize to polynucleotides comprising complementary nucleotide sequences. The presence of mRNAs comprising target nucleotide sequences for detection can be determined by detecting this hybridization. For example, whether mRNAs comprise target mRNAs can be directly tested using Northern blotting. Alternatively, the presence of target mRNAs can also be detected using RT-PCR methods. Further, mRNAs comprised in cells can also be directly analyzed by in situ hybridization or in situ PCR. All these analysis methods are known.

Oligonucleotides that can be used in the detection methods of the present invention can be used as reagents for detecting activated IPCs. The oligonucleotides in the reagents of the present invention for detecting activated IPCs may be prelabeled. Labels include fluorescent substances, luminescent substances, radioactive substances, and substances with binding affinity. Known fluorescent substances include FITC and rhodamine. As substances with binding affinity, biotin, digoxigenin and the like can be used.

The nucleotide sequences of oligonucleotides used to detect activated IPCs in the present invention comprise nucleotide sequences complementary to a nucleotide sequence selected from the group consisting of SEQ ID NOs: 1, 3, and 5. Nucleotide sequences that specifically hybridize are not necessarily perfectly complementary to target nucleotide sequences. Mutations in the sequences are acceptable as long as the desired specificity is achieved under stringent conditions. Oligonucleotides comprising set nucleotide sequences can be prepared by chemical synthesis. When appropriate labels are added, the oligonucleotides can be used in various types of hybridization assays.

When using the oligonucleotides as primers, multiple regions may be set according to the principle of complementary strand synthesis. For example, when used as PCR primers, the oligonucleotides are selected as primers for regions prescribed by the 5' and 3' ends of a target segment to be synthesized. The oligonucleotides of the present invention are applicable to various complementary strand synthesis reactions, including not only standard PCR but also RT-PCR using RNAs as templates, nested PCR in which the region to be amplified are nested to allow highly sensitive detection, and cDNA synthesis.

Furthermore, the level of in vivo IPC activation can be determined not only by methods using antibodies but also by hybridization assays or methods using nucleic acid amplification. Specifically, the level of in vivo IPC activation can be determined by determining the ratio of the number of activated IPCs detected according to the present invention to the total number of IPCs. Markers that can reflect the entire IPC population include BDCA2 and BDCA4, described above. The number of cells cannot be directly determined by measuring markers using hybridization assays or nucleic acid amplification. However, total RNAs extracted from samples or results obtained using total mRNAs as a target reflect the number of cells that express each marker. Thus, by comparing the expression levels of each marker, the activation levels can also be determined. Normalization of cell counts between control samples is sometimes needed to accurately compare expression levels between samples. Genes that maintain constant expression levels regardless of cell type and condition can be used to normalize cell counts. Such marker genes include β-actin and glyceraldehyde-3-phosphate dehydrogenase (GAPDH).

Furthermore, the present invention also provides methods for separating activated IPCs using BST2 or its homologues as indicators. Specifically, the present invention relates to methods for separating activated IPCs, which comprise the step of isolating cells that comprise an indicator substance of (a) to (d):
(a) polynucleotides comprising a nucleotide sequence selected from the group consisting of SEQ ID NOs: 1, 3, and 5;
(b) polynucleotides comprising a consecutive nucleotide sequence selected from a nucleotide sequence selected from the group consisting of SEQ ID NOs: 1, 3, and 5;
(c) proteins comprising an amino acid sequence selected from the group consisting of SEQ ID NOs: 2, 4, and 6; and
(d) proteins comprising a consecutive amino acid sequence selected from an amino acid sequence selected from the group consisting of SEQ ID NOs: 2, 4, and 6.

Like the antibodies in the above detection methods, antibodies which bind to indicator substances in the separation methods of the present invention may be bound to labeling components or solid phases. Activated IPCs can be separated by binding cell populations that comprise activated IPCs to antibodies against a marker described in (c) or (d) above, and then fractionating cells bound to the antibodies. For example, when using antibodies bound to a label component, activated IPCs can be separated by monitoring the label component and fractionating cells bound to the label component. When antibodies immobilized onto a solid phase are used, activated IPCs can be separated by collecting the solid phase.

Techniques for separating activated IPCs using antibodies are specifically described below. For example, methods that comprise directly or indirectly binding cells to antibodies immobilized onto water-insoluble carriers can be used. Such water-insoluble carriers include beads and matrices made of cellulose derivatives, agarose, and the like. Immunoadsorption columns can be prepared by filling columns with such water-insoluble carriers immobilized with antibodies. Activated IPCs captured by antibodies on insoluble carriers can be eluted using buffers capable of dissociating immunological bonds.

Alternatively, fluorescent antibody-based methods and methods using immunomagnetic beads can be used to separate cells. Specifically, such methods comprise separating target cells bound to antibodies one by one using a fluorescent label or magnetic label as an indicator. Cell sorters such as FACS and MACS are advantageously used in such separation methods. Methods for separating cells using cell sorters are known.

For example, when cells are separated using AutoMACS, cell populations comprising activated IPCs are contacted with antibodies that recognize markers. After washing the cells with PBS, the cells are then reacted with a secondary antibody. When the antibody against a marker is mouse IgG, the secondary antibody can be a biotinylated anti-mouse IgG antibody and such. Alternatively, secondary antibodies are unnecessary when antibodies against markers are previously biotinylated. After washing the cells with PBS, the cells are reacted with streptavidin magnetic beads. Thus, activated IPCs bind to the magnetic beads. By passing the yielded cells through a magnetic column, the activated IPCs can be captured in the column. After the column is washed, the cells that remained in the column are eluted, and the activated IPCs can be collected. When MACS is used, the treatment is completed in about 30 minutes. Thus, the separation methods of the present invention are useful for preparing large quantities of activated IPCs, only a small amount of which are detected in vivo.

The present invention also relates to methods for separating activated IPCs, which comprise the step of isolating cells that comprise an above indicator substance (a) to (d). The present invention demonstrated that the above indicator substances (a) to (d) could be used as markers specific to activated IPCs. Thus, activated IPCs can be separated by isolating cells in which these indicator substances have been detected. Methods for detecting these indicator substances are described above.

The present inventors also confirmed that the expression of the above indicator substances (a) to (d) is enhanced upon viral stimulation of IPCs. Based on this finding, the level of IPC activation can be determined by measuring an above indicator substances (a) to (d). Specifically, the present invention provides methods for determining the level of IPC activation, which comprise the steps of:

(1) determining the expression level of an above indicator substance (a) to (d) in IPCs; and
(2) judging that tested cells are activated when the expression level of the indicator substance determined in (1) is increased as compared with that in unstimulated IPCs.

Alternatively, activated IPCs are detected when the expression level of the indicator substance determined in (1) is increased as compared with that in unstimulated IPCs.

Methods for determining the expression levels of the above indicator substances (a) to (d) are described above. When the expression levels of the above indicator substances (a) to (d) in IPCs are increased in vivo or in vitro as compared with that in unstimulated IPCs, the IPCs can be confirmed to be activated. IPCs have been found to be activated upon viral stimulation. Thus, an increase in the expression levels of the above indicator substances (a) to (d) in IPCs is a useful indicator of viral stimulation of the IPCs. Specifically, the contact of IPCs with viruses can be detected by detecting an increase in the expression levels of an above indicator substance (a) to (d). Contact between IPCs and viruses means that the individuals from which the IPCs were derived have experienced viral infection. Thus, viral infection in individuals can be detected by the present invention.

The present invention also provides methods for measuring the activity of regulating IPC activation by using as indicators the above indicator substances (a) to (d) in IPCs. Specifically, the present invention provides methods for detecting the activity of test substances in regulating the activation of IFN-producing cells, which comprise the steps of:
(1) contacting IFN-producing cells with a cell stimulant along with a test substance, or contacting IFN-producing cells with a cell stimulant before or after contact with a test substance;
(2) determining the expression level of an indicator substance (a) to (d) in the IFN-producing cells:
  (a) polynucleotides comprising a nucleotide sequence selected from the group consisting of SEQ ID NOs: 1, 3, and 5;
  (b) polynucleotides comprising a consecutive nucleotide sequence selected from a nucleotide sequence selected from the group consisting of SEQ ID NOs: 1, 3, and 5;
  (c) proteins comprising an amino acid sequence selected from the group consisting of SEQ ID NOs: 2, 4, and 6; and
  (d) proteins comprising a consecutive amino acid sequence selected from an amino acid sequence selected from the group consisting of SEQ ID NOs: 2, 4, and 6; and
(3) comparing the expression level of the indicator substance determined in (2) with that of a control, and detecting an activity of the test substance in enhancing IPC activation when the expression level is significantly higher than that of the control, or detecting an activity of the test substance in suppressing IPC activation when the expression level is significantly lower than that of the control.

Figure 13:
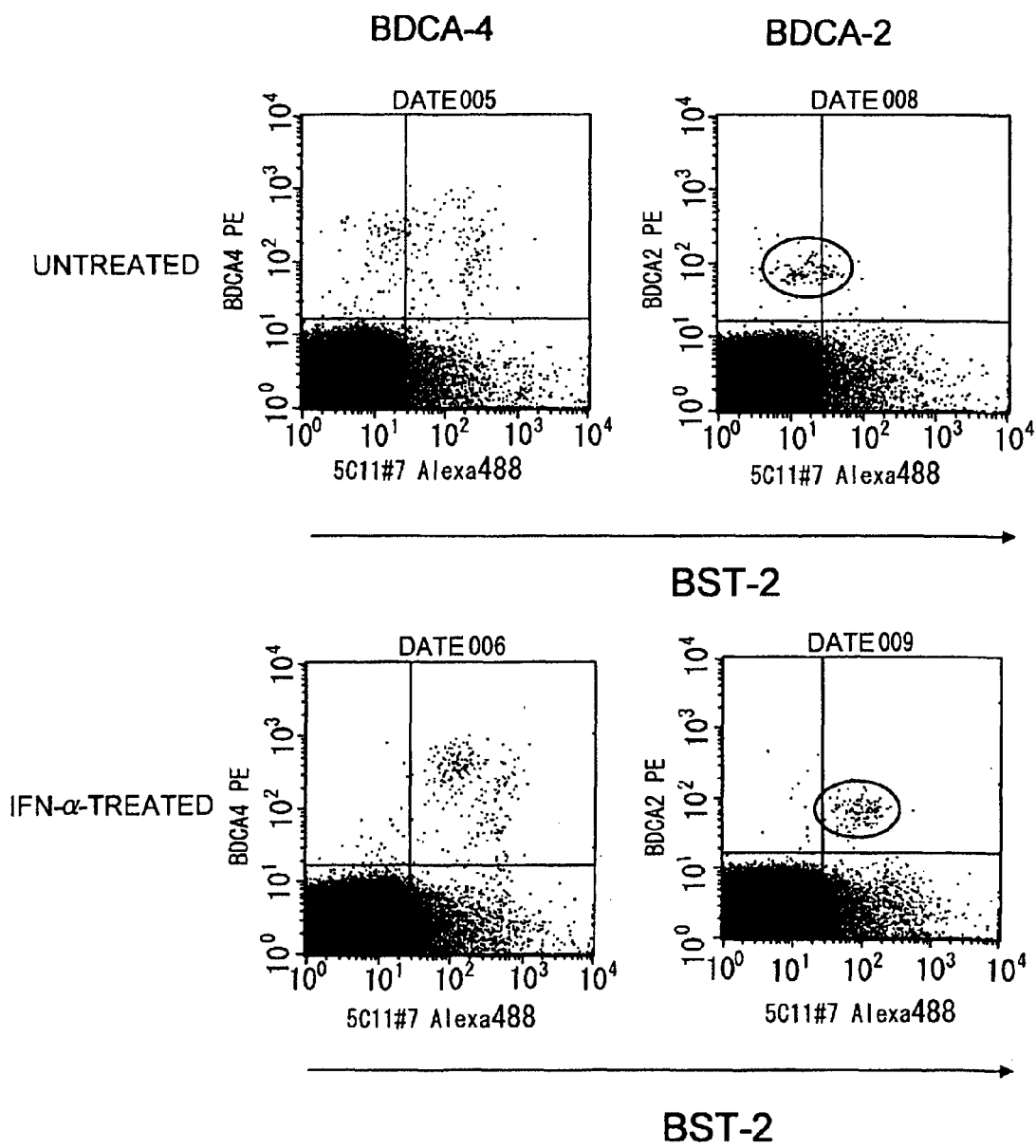
FIG. 13 is graphs showing the analysis of BST2 expression in human IPCs stimulated with IFNα. Anti-BDCA-4 and BDCA-2 antibodies were used as markers for human IPCs. The horizontal axes indicate the fluorescence intensity for 5C11#7 antibody, namely, the BST2 expression level. The vertical axes indicate cell count.

The cell stimulants in the methods of the present invention refer to substances capable of inducing IPC activation. For example, the cell stimulants can include viruses and viral components. Specifically, IPCs are known to be activated upon administration of viruses such as herpes simplex virus (HSV) and influenza virus. Further, the bacterial DNA CpG is also known to have the activity of activating IPCs. In addition, IPCs are also known to be activated upon contact with interferons. Specifically, as shown in FIG. 13, IPCs themselves are activated by IFN-α. These cell stimulants may be used singly or in combination. IPCs may be simultaneously contacted with cell stimulants and test substance, or IPCs may be contacted with test substances before or after contact with cell stimulants.

In the present invention, the cell stimulants, IPCs, and test substances may be contacted in vitro, in vivo, or ex vivo. When contacted in vitro, cell stimulants and test substances may be contacted with IPCs in any order, as described above, under conditions that allow IPC culture. When contact is in vivo, IPCs are collected after in vivo administration of the test substances or cell stimulants to the IPCs. The level of cellular activation can be evaluated after the collected IPCs are contacted with cell stimulants or test substances in vitro. The level of cellular activation can be evaluated based on changes in the concentration of IFNs produced in the cells, or such.

Furthermore, in ex vivo evaluation, IPCs prepared in vitro are contacted with the cell stimulants or test substances. After contact, IPCs are administered to the living body, and then the test substances or cell stimulants are administered. The activity of a test substance is evaluated by evaluating the level of IPC activation in vivo. The level of IPC activation can be evaluated, for example, using blood IFN levels as an indicator. The in vitro preparation of IPCs means that IPCs are collected from a living body, or IPCs are artificially prepared by inducing the differentiation of IPC precursor cells.

Since IFN production is induced by stimulating IPCs, production can be regulated by regulating IPC activation. In the present invention, regulation of IPC activation comprises suppression and enhancement of activation. Specifically, substances capable of enhancing IPC activation are useful as enhancers for IFN production. In the present invention, various substances can be evaluated for the activity of enhancing or suppressing IPC activation by stimulation such as viral stimulation. Substances capable of suppressing IPC activation can be used as agents for suppressing IFN production.

In the methods of the present invention, substances whose influences on IPC activation are already known can be used as controls, instead of test substances. For example, physiological saline is a substance that does not influence IPC activation. Alternatively, by using substances confirmed to enhance or suppress IPC activation as controls, test compound activities can also be evaluated by comparison with such substances.

Reagents for determining the above indicators (a) to (d) can be used as reagents for measuring the activity of regulating IPC activation based on the present invention. For example, oligonucleotides comprising a nucleotide sequence comprising at least 15 consecutive nucleotides selected from a nucleotide sequence selected from the group consisting of SEQ ID NOs: 1, 3, and 5 are useful as reagents for detecting the activity of regulating IPC activity.

Alternatively, antibodies that recognize proteins comprising an amino acid sequence selected from the group consisting of SEQ ID NOs: 2, 4, and 6 are useful as reagents for detecting the activity of regulating IPC activity. Such antibodies can include antibodies recognizing either or both of BST2 and its splicing variants.

The reagents of the present invention for measuring the activity of regulating IPC activation can also be combined with cell stimulants for activating IPCs, media and vessels for culturing IPCs, and such. Further, substances whose influences on IPC activation are known can also be combined as controls.

The present invention also provides methods of screening for substances with the activity of regulating IPC activation, by using the methods for measuring the activity of regulating IPC activation. Specifically, the present invention provides methods of screening for test substances with the activity of regulating IPC activity, which comprise the steps of:
(1) contacting IFN-producing cells with a cell stimulant along with a test substance, or contacting IFN-producing cells with a cell stimulant before or after contact with a test substance;

(2) determining the expression level of an indicator substance (a) to (d) in IFN-producing cells:
(a) polynucleotides comprising a nucleotide sequence selected from the group consisting of SEQ ID NOs: 1, 3, and 5;
(b) polynucleotides comprising a consecutive nucleotide sequence selected from a nucleotide sequence selected from the group consisting of SEQ ID NOs: 1, 3, and 5;
(c) proteins comprising an amino acid sequence selected from the group consisting of SEQ ID NOs: 2, 4, and 6; and
(d) proteins comprising a consecutive amino acid sequence selected from an amino acid sequence selected from the group consisting of SEQ ID NOs: 2, 4, and 6;
(3) comparing the expression level of the indicator substance determined in (2) with that of a control, and detecting an activity of the test substance in enhancing IPC activation when the expression level is significantly higher than that of the control, or detecting an activity of the test substance in suppressing IPC activation when the expression level is significantly lower than that of the control; and
(4) selecting a test substance that has a strong above-described activity of regulating activation as compared with a control.

Compounds that can be selected by the screening methods of the present invention are useful as agents for regulating IPC activation. When IPCs that have been contacted with substances known to have the activity of enhancing IPC activation are used as controls in the screening methods of the present invention, substances with an activation-enhancing activity that is stronger than these substances can be discovered. Conversely, when IPCs that have been contacted with substances with the activity of suppressing IPC activation are used as controls, substances with an activation-suppressing activity that is stronger than these substances can be discovered.

IPCs are important cells that produce a majority of IFNs in vivo. Thus, compounds that can be obtained by the screening methods of the present invention are important as agents for regulating the immune system. For example, methods of screening for therapeutic agents for autoimmune diseases or allergies are provided by using the methods for measuring the activity of suppressing IPC activation based on the present invention. The present invention also relates to therapeutic agents for autoimmune diseases or allergies, which comprise as active ingredients compounds with the activity of suppressing IPC activation, which are selected by the screening methods of the present invention.

For example, IFNα is currently used clinically as a therapeutic agent for hepatitis C virus. IFNα preparations are very expensive. Substances with the activity of enhancing IPC activation, which can be selected by screening according to the present invention, can be used as agents for enhancing IFN production in IPCs. Administration of such agents is expected to have the same therapeutic effect as that of IFNα administration. IFNα is thought to be applicable not only to hepatitis C but also to AIDS and other viral diseases. IFNα can also be expected to produce anti-cancer effects. Specifically, methods of screening for therapeutic agents for viral diseases or cancers are provided by using the methods for measuring the activity of enhancing IPC activation based on the present invention. The present invention also relates to therapeutic agents for viral diseases or cancers, which comprise as active ingredients compounds with the activity of enhancing IPC activation, which are selected by the screening methods of the present invention.

The test substances to be used in the screening methods of the present invention include preparations of compounds synthesized by combinatorial chemistry, as well as mixtures comprising multiple compounds such as extracts of animal and plant tissues and cultures of microorganisms, and preparations obtained by purifying these mixtures.

Of the substances identified as markers specific to activated IPCs in the present invention, the polynucleotides comprising the nucleotide sequences of the SEQ IDs below, and the proteins comprising the amino acid sequences encoded by these polynucleotides, were novel substances. These markers with novel structures were thought to be splicing variants of the known gene BST2. In the present invention, the splicing variants are called "BST2H" and "BST2HS".

|        | Nucleotide sequence | Amino acid sequence encoded by the nucleotide sequence |
|--------|--------------------|--------------------------------------------------------|
| BST2H  | SEQ ID NO: 3       | SEQ ID NO: 4                                           |
| BST2HS | SEQ ID NO: 5       | SEQ ID NO: 6                                           |

Specifically, the present invention relates to the polynucleotides described below in (i) to (vi), and proteins comprising the amino acid sequences encoded by the polynucleotides:
(i) polynucleotides encoding proteins comprising the amino acid sequence of SEQ ID NO: 4 or 6;
(ii) polynucleotides comprising a coding region of the nucleotide sequence of SEQ ID NO: 3 or 5;
(iii) polynucleotides encoding proteins that comprise amino acid sequences with a substitution, deletion, insertion, and/or addition of one or more amino acids in the amino acid sequence of SEQ ID NO: 4 or 6 and that are functionally equivalent to a protein comprising the amino acid sequence of SEQ ID NO: 2;
(iv) polynucleotides that hybridize under stringent conditions to a DNA comprising the nucleotide sequence of SEQ ID NO: 3 or 5;
(v) polynucleotides encoding the amino acid sequence of position 139 to 158 from the N terminus of the amino acid sequence of SEQ ID NO: 4; and
(vi) polynucleotides encoding the amino acid sequence of position 96 to 100 from the N terminus of the amino acid sequence of SEQ ID NO: 6.

The polynucleotides of the present invention comprise isolated polynucleotides. In the present invention, isolated polynucleotides mean polynucleotides separated from other nucleic acid molecules that exist in the natural sources from which the polynucleotides are derived. Isolated polynucleotides include, for example, recombinant DNA molecules comprised in vectors, recombinant DNA molecules in heterologous host cells, partially or substantially purified nucleic acid molecules, and synthetic DNA and RNA molecules. When "isolated" polynucleotides such as cDNA molecules are prepared by recombinant techniques, they comprise virtually no other cellular materials or culture media. Meanwhile, chemically synthesized polynucleotides can comprise virtually no chemical precursors or other chemical substances.

The proteins of the present invention comprise isolated or purified proteins. "Isolated" or "purified" proteins, and biologically active segments thereof comprise virtually no cellular material or other contaminating proteins sourced from cells or tissues, for example, from which proteins comprising the above amino acid sequence of SEQ ID NO: 4 or 6 are derived. When the proteins of the present invention are chemically synthesized, they comprise virtually no chemical precursors or other chemical substances. The phrase "comprise virtually no cellular material" means that the proteins are separated from cellular components of the cells from which they were isolated or prepared by recombination. In one embodiment, the phrase "comprise virtually no cellular material" means other proteins contaminating the proteins of the present invention are less than about 30%, more preferably less than about 20%, still more preferably less than about 10%, and most preferably less than about 5% by dry weight. When prepared by recombination, the proteins of the present invention or biologically active segments thereof preferably comprise virtually no culture medium. In the present invention, the phrase "comprise virtually no culture medium" means that culture medium accounts for less than about 20%, more preferably less than about 10%, and most preferably less than about 5% of the volume of a protein preparation.

The amino acid sequence from the N terminus to position 138 of the amino acid sequence of SEQ ID NO: 4 is identical to the amino acid sequence of SEQ ID NO: 2. Likewise, the amino acid sequence from the N terminus to position 95 of the amino acid sequence of SEQ ID NO: 6 is identical to the amino acid sequence of SEQ ID NO: 2. The amino acid sequence of SEQ ID NO: 2 is known as BST2 (bone marrow stromal cell antigen 2; GenBank Acc#. BC027328). The proteins comprising novel amino acid sequences, discovered by the present inventors, are thought to be BST2 splicing variants.

The polynucleotides of the present invention and the proteins comprising the amino acid sequences encoded by these polynucleotides, and any materials functionally equivalent thereto, are all useful as indicators of IPC activation. The amino acid sequences unique to the proteins of the present invention described below, which were identified by the present invention, are also useful as immunogens for preparing antibodies that specifically bind to the proteins of the present invention. By using such antibodies, proteins comprising the amino acid sequences of SEQ ID NOs: 4 and 6 can be detected and discriminated from proteins comprising the amino acid sequence of SEQ ID NO: 2. Specifically, the present invention relates to antibodies that recognize regions comprising the following amino acid sequences:
the amino acid sequence from position 139 to 158 in SEQ ID NO: 4; and
the amino acid sequence from position 96 to 100 in SEQ ID NO: 6.

The antibodies of the present invention can be prepared by using polypeptides comprising the above amino acid sequences as immunogens. Specifically, for example, polypeptides of five to 50 amino acid residues, for example, five to 30 amino acid residues, can be used as immunogens. Polypeptides for use as immunogens can be prepared by chemical synthesis or by digesting proteins comprising the amino acid sequences of SEQ ID NOs: 4 and 6. The immunogen polypeptides may be linked with carrier proteins. Keyhole limpet hemocyanin and the like can be used as carrier proteins. Alternatively, proteins comprising the amino acid sequences of SEQ ID NOs: 4 and 6 may be used as immunogens without any treatment.

The antigenic determinants for the yielded antibodies can be identified using epitope mapping. Epitope mapping refers to the identification of amino acid sequences recognized by antibodies (antigenic determinants). In fact, antigenic determinants can be identified using absorption tests or binding tests using peptides comprising the above amino acid sequences or partial sequences thereof, or multiple oligopeptides that comprise various amino acid sequences comprising the above amino acid sequences.

Antibodies that distinguish conformations unique to each subtype, in addition to recognizing such differences in primary structure, can be used to detect and discriminate subtypes. Antibodies that distinguish conformations can be selected by clarifying whether antibodies prepared using each of the subtypes as an immunogen exhibit cross-reactivity to other subtypes. For example, when the binding activity of a selected antibody that specifically binds to each of the subtypes is not cancelled by absorption treatment using oligopeptides comprising an above unique amino acid sequence, that antibody may recognize a conformation unique to a subtype.

Likewise, nucleotide sequences that encode these amino acid sequences in the nucleotide sequences of SEQ ID NO: 3 or 5 are useful as target sequences for specifically detecting each gene. Specifically, oligonucleotides that hybridize to polynucleotides comprising the following nucleotide sequences are useful as probes or primers for detecting the polynucleotides of the present invention:
the nucleotide sequence from position 418 to 477 of SEQ ID NO: 3; and
the nucleotide sequence from position 289 to 303 of SEQ ID NO: 5.

The polynucleotides of the present invention can be yielded by screening IPC cDNA libraries using probes designed based on the nucleotide sequence of SEQ ID NO: 1. Alternatively, the polynucleotides of the present invention can be synthesized by PCR (Current Protocols in Molecular Biology edit. Ausubel et al. (1987) Publish. John Wiley & Sons Section 6.1-6.4) using primers designed based on the nucleotide sequence of SEQ ID NO: 1 and an mRNA or an IPC cDNA library as a template. Those skilled in the art can design probes and primers based on given nucleotide sequences.

The polynucleotides of the present invention comprise polynucleotides which encode proteins that comprise amino acid sequences with a substitution, deletion, insertion, and/or addition of one or more amino acids in the amino acid sequence of SEQ ID NO: 4 or 6 and that are functionally equivalent to a protein comprising the amino acid sequence of SEQ ID NO: 4 or 6. Herein, "proteins functionally equivalent" comprise proteins expressed in activated IPCs and whose expression levels increase along with IPC activation. In a preferred embodiment of the present invention, the activities of cells expressing the functionally equivalent proteins can be suppressed when the cells are contacted with antibodies which bind to the proteins. Herein, cell activities comprise either or both of IFN-producing ability and the number of cells. Herein, the IFN-producing ability of cells preferably refers to the ability to produce type 1 IFN. More specifically, IFN-producing ability refers to the ability to produce either or both of IFNα and IFNβ.

Mutations in amino acid sequences may be artificial or spontaneous mutations. The proteins of the present invention are preferably derived from natural sources. In the present invention, an acceptable number of amino acid mutations is typically 50 amino acids or less, preferably 30 amino acids or less, and more preferably ten amino acids or less. For example, substitutions of five amino acids or less, or of three amino acids or less are acceptable. When amino acids are substituted, conservative substitutions are preferred. In general, to retain protein functions, the substituted amino acids preferably have properties similar to those of the amino acid before substitution. Such amino acid residue substitutions are called "conservative substitutions".

Conservative amino acid substitutions can be achieved, for example, by substitution between the amino acids in each of the following categories:
Non-polar amino acids: Ala, Val, Leu, Ile, Pro, Met, Phe, and Trp
Non-charged amino acids: Gly, Ser, Thr, Cys, Tyr, Asn, and Gln
Acidic amino acids: Asp and Glu
Basic amino acids: Lys, Arg, and His The polynucleotides of the present invention may also be conjugated to polynucleotides encoding other proteins or polypeptides. Such polynucleotides produce conjugates between the proteins of the present invention and other proteins or polypeptides (fusion proteins). For example, methods for attaching histidine tags, flag-tags, and the like to arbitrary proteins are known. These attached proteins can be used to detect or purify the proteins of the present invention. As long as they retain a function of a protein of the present invention, the proteins of the present invention may also be fusion proteins comprising such proteins.

The polynucleotides of the present invention also comprise polynucleotides that hybridize under stringent conditions to DNAs comprising the nucleotide sequence of SEQ ID NO: 1. In the present invention, hybridization conditions can be exemplified by washing conditions typically around "1×SSC/ 0.1% SDS at 37° C.", more stringent conditions of around "0.5×SSC/0.1% SDS at 42° C.", and still more stringent condition of around "0.1×SSC/0.1% SDS at 65° C.". Polynucleotides exhibiting higher homology can be obtained as the stringency of conditions increases. In the present invention, stringent conditions can be exemplified by hybridization in "6×SSC/40% formamide at 37° C." and washing with "0.2× SSC at 55° C.".

The above combinations of SSC, SDS, and temperature conditions are examples. Those skilled in the art can achieve hybridization stringencies equivalent to the above by controlling the various conditions that determine the stringencies. For example, conditions in addition to those described above that influence stringency include probe concentration, probe length, and hybridization reaction time.

Polynucleotides obtained using such hybridization techniques have high homology to the nucleotide sequence of SEQ ID NO: 1. Further, the amino acid sequences encoded by polynucleotides with highly homologous nucleotide sequences are also expected to have high homology. In the present invention, high homology means identity of 90% or more, 93% or more, 95% or more, 97% or more, or 99% or more. Identity can be determined using a BLAST search algorithm.

The homologies of the amino acid sequences and nucleotide sequences of the present invention can be determined using the BLAST algorithm of Karlin and Altschul (Proc. Natl. Acad. Sci. USA 90:5873-5877, 1993). Programs called blastn and blastx have been developed based on this algorithm (Altschul et al. J. Mol. Biol. 215:403-410, 1990). When a nucleotide sequence is analyzed using blastn, based on BLAST, the parameters are set, for example, at score=100 and wordlength=12. Also, when an amino acid sequence is analyzed using blastx, based on BLAST, the parameters are set, for example, at score=50 and wordlength=3. When using the BLAST and Gapped BLAST programs, default parameters for each of the programs are used. Specific procedures for these analysis methods are known (http://www.ncbi.nlm.nih.gov/).

In addition, the present invention relates to vectors inserted with the polynucleotides of the present invention. Such vectors of the present invention are not particularly limited, and any vector can be used as long as it can stably carry the insert DNA. For example, when using *E. coli* as the host, a pBluescript vector (Stratagene) or the like is preferred as a cloning vector. When using such vectors to produce the proteins of the present invention, expression vectors can be used. Various vectors for expressing arbitrary genes are commercially available. Desired vectors can be obtained by inserting DNAs of the present invention into the cloning sites of these vectors.

The present invention also relates to transformants carrying the vectors of the present invention. Host cells introduced with the vectors of the present invention are not particularly limited, and various host cells can be used, depending on purpose. Eukaryotic cells for expressing the proteins at high levels can include, for example, COS cells and CHO cells.

Methods for introducing vectors into host cells are known. For example, vectors can be introduced into host cells using the calcium phosphate precipitation method, electroporation (Current Protocols in Molecular Biology edit. Ausubel et al. (1987) Publish. John Wiley & Sons. Section 9.1-9.9), lipofectamine methods (GIBCO-BRL), microinjection methods, or such. The expression of proteins with an amino acid sequence of interest is induced by culturing cells introduced with the vectors under conditions allowing induction of expression of the gene. Furthermore, the proteins of the present invention can be isolated by purifying proteins from transformant cultures. Methods for purifying recombinant proteins are also known. Proteins of the present invention that can be thus prepared are useful, for example, as immunogens for preparing antibodies that recognize the proteins of the present invention.

All prior-art documents cited herein are incorporated herein by reference.

Hereinbelow, the present invention will be specifically described with reference to Examples.

Example 1

Protocol for Monoclonal Antibody Preparation

Cells for use as immunogens were prepared as described below: Bone marrow cells from female Balb/c mice (four to six weeks old) were cultured for ten days in RPMI1640 containing 10% FCS [RPMI1640 containing 10% fetal calf serum (FCS), penicillin, and streptomycin] supplemented with 10 ng/ml FLT-3 ligand (R&D Systems). After ten days of culture, interferon-producing cells (IPCs) were separated as CD 11 c-positive, B220-positive, and CD11b-negative fractions using a cell sorter (FACSVantage; Becton Dickinson). The antibodies used were obtained from Becton Dickinson.

On days zero, four, and eleven, cells separated as described above were injected along with Freund's complete adjuvant (CFA: Iatron) into the foot pads of rats, at a dose of $1\times10^6$ cells/leg. On day 12, lymph nodes were excised from the immunized rats and lymphocytes were collected. Cells of mouse myeloma P3x63Ag8.653 and the rat lymphocytes were combined at a ratio of 4:5, and then polyethylene glycol (PEG) was added to fuse the cells. After fusion, the cells were washed thoroughly, dispersed in HAT medium, then plated in 96-well plates at $5\times10^4$ cells/well.

Cells were harvested from the wells in which they were grown, diluted, and screened using the reactivity of the culture supernatants to mouse spleen cells and to cultured bone marrow cells as indicators. Screening methods are described in detail in Example 2. Cells from wells showing a positive response were cloned using limiting dilution, and hybridoma clones that produced monoclonal antibodies were established. Further, antibodies were purified from the culture supernatants of the hybridomas or from ascites yielded by transplanting the hybridomas into mouse peritoneal cavities, and these purified antibodies were analyzed for reactivity.

Example 2

Screening of Culture Supernatants

Bone marrow cells from female Balb/c mice (four to six weeks old) were cultured for ten days in RPMI1640 containing 10% FCS supplemented with 10 ng/ml FLT-3 ligand. About 40% of cells had become IPCs by day 10. The cells were stained using culture supernatants of hybridomas as primary antibodies and an FITC-labeled anti-rat Ig antibody as a secondary antibody (BD Pharmingen). Then, the cells were double stained using various antibodies (against CD11b, CD11c, CD3, CD19, CD45RB, B220, and Ly6C; all Becton Dickinson) and analyzed using flow cytometry methods (FACS analysis).

Positive and negative fractions of culture supernatant are referred to as R2 and R3, respectively; the expression of the various antigens in each gate are shown in a histogram (FIG. 1). The cell surface antigen profiles of cell populations stained with several of the prepared antibodies were identical to those of mouse IPCs defined in previous reports (Nature Immunol., 2001; 2, 1144-1150). Thus, these antibodies were thought to bind specifically to mouse IPCs.

Example 3

Morphology of Cells Separated Using Antibodies

Bone marrow cells cultured as in Example 2 were stained using culture supernatants as primary antibodies and an FITC-labeled rat Ig antibody as a secondary antibody. Then, positive cells were separated using a cell sorter (FACSVantage, Becton Dickinson). After cytospinning, cells were Giemsa-stained, and observation under a microscope revealed IPC-specific morphology (FIG. 2a). Specifically, the cells were round and had large nuclei.

$1 \times 10^5$ cells were cultured in the presence of influenza virus PR8 in round-bottomed 96-well plates for 24 hours at 37° C. The cells were then similarly Giemsa-stained and observed under a microscope, showing that the cells had differentiated into dendritic cells with typical morphology (FIG. 2b). This result confirmed that cells separated using the above antibodies differentiate into dendritic cells upon viral infection, and thus have features characteristic of mouse IPCs. SNK01 was selected from these mouse-IPC-specific monoclonal antibodies and hybridomas producing such antibodies, and was used in the subsequent experiments.

Example 4

The Interferon-Producing Ability of Cells Separated Using Antibodies

Bone marrow cells cultured as in Example 2 were stained using the SNK01 culture supernatant and a secondary antibody, and then positive and negative cells were separated using a cell sorter. $1 \times 10^5$ cells of each cell fraction were dispensed into round-bottomed 96-well plates (100 µl/well), and infected with influenza virus PR8. After 24 hours, the concentration of IFNα in the culture supernatant was determined by the following ELISA method:

First, 96-well plates were coated with a rat anti-mouse IFNα antibody (PBL Biomedical Laboratory) by reaction overnight at 4° C. After washing the plates, 100 µl of culture supernatant was added, and this was reacted at 4° C. overnight. After the plates were washed, a labeled anti-interferon antibody recognizing IFNα and IFNβ was added, the plates were incubated for one hour, and then detection was carried out. Each reaction was conducted in triplicate and values were averaged. The concentration of IFNα in the culture supernatant was calculated by preparing a standard curve.

Figure 3:
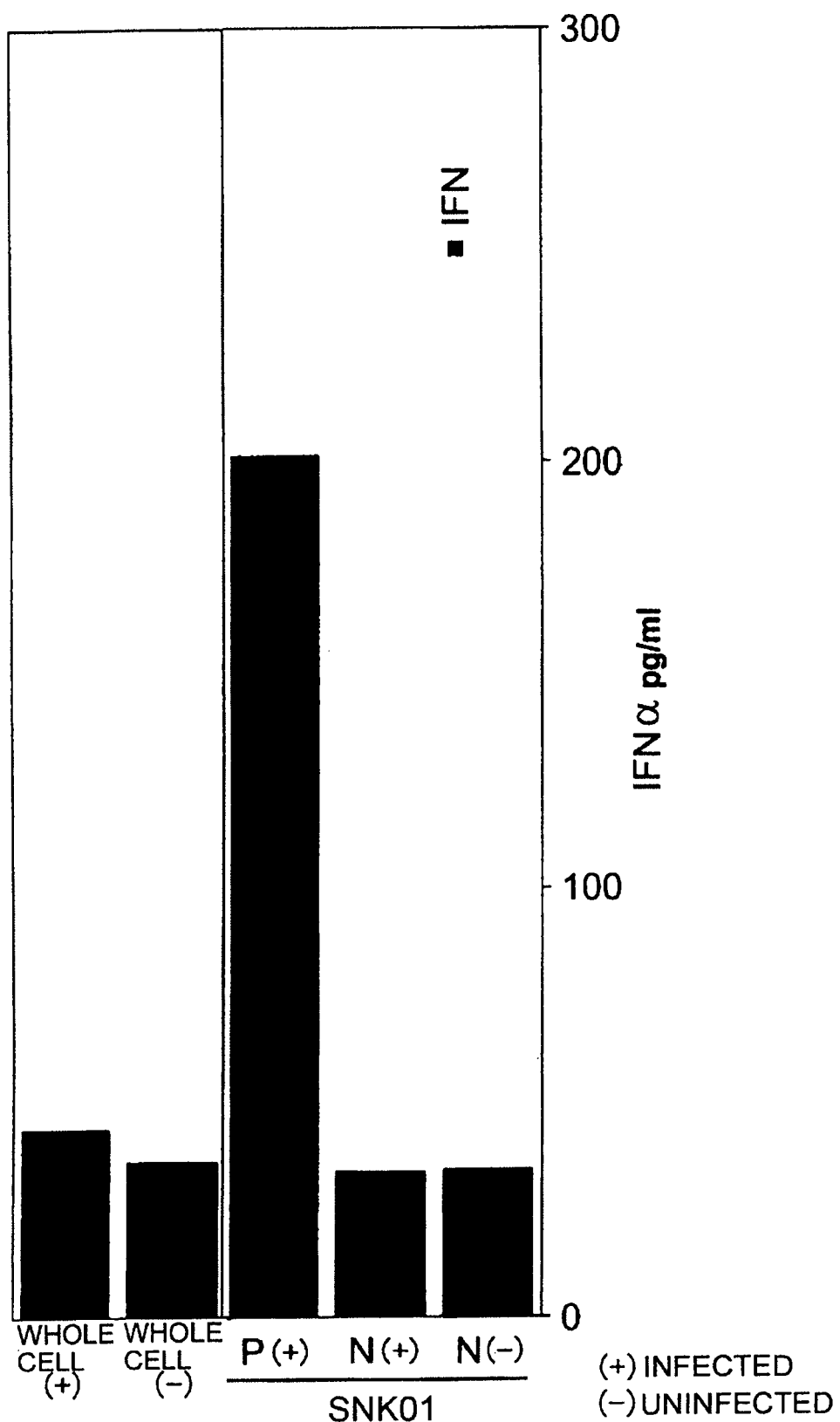
FIG. 3 is a graph showing the interferon-producing ability of cells isolated using monoclonal antibody SNK01. In the graph, the horizontal axis indicates the types of cell treatment, and the vertical axis indicates the concentration of IFNα (pg/ml) in the culture supernatant. P(+) on the horizontal axis shows the results when cells bound to the monoclonal antibody are infected with the virus; N(+) shows the results when cells which did not bind to the monoclonal antibody are infected with the virus; and N(-) shows the results for cells which did not bind to the monoclonal antibody and were not infected with the virus.

SNK01-positive cells were found to produce interferon at a higher level than negative cells. Specifically, the antigen recognized by monoclonal antibody SNK01 was confirmed to be an IPC-specific surface antigen (FIG. 3).

Example 5

Influence of Antibodies on Interferon-Producing Ability

Figure 4:
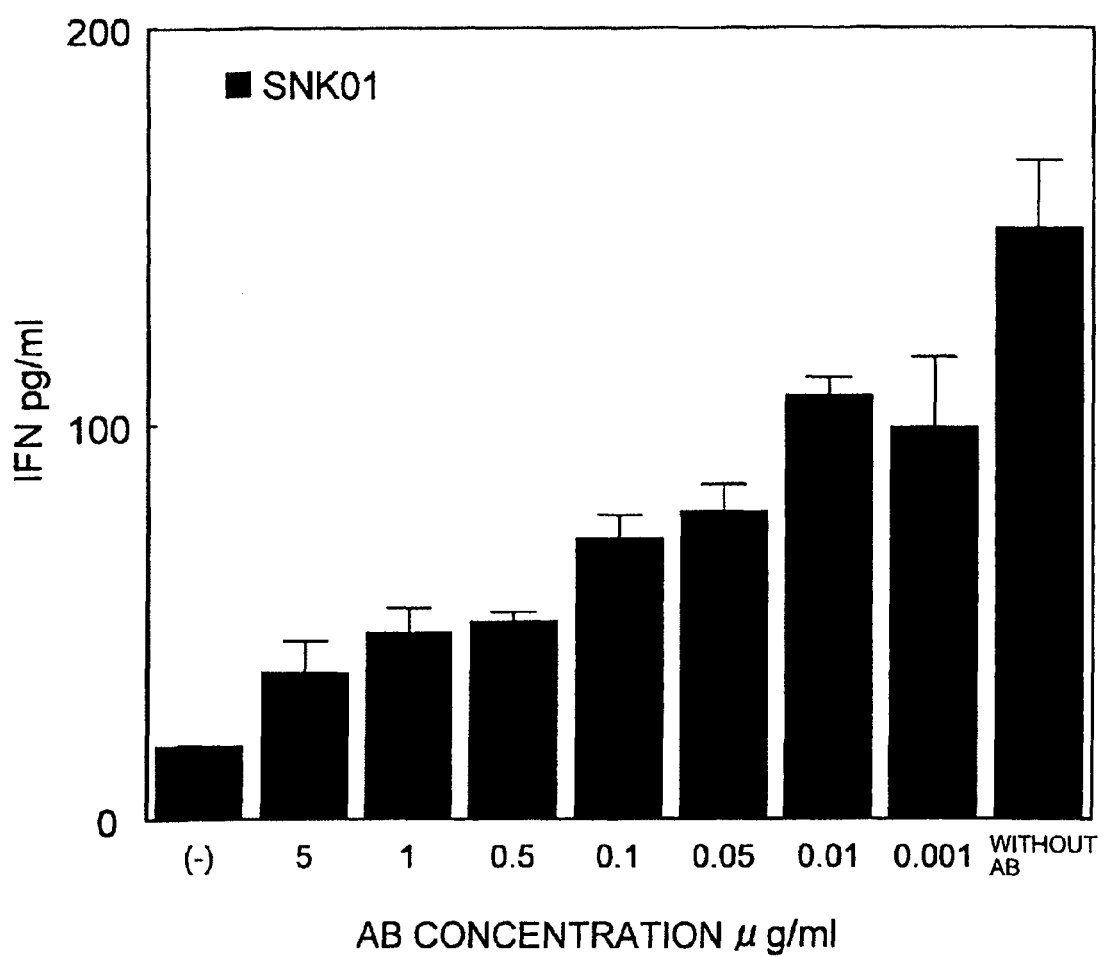
FIG. 4 is a graph showing the influence of monoclonal antibody SNK01 on interferon-producing ability. In this graph, the horizontal axis indicates the antibody concentration (μg/ml) used in the treatment, and the vertical axis indicates the IFNα concentration (pg/ml) in the culture supernatant. In the horizontal axis, (-) shows the results without viral treatment. SNK01 exhibited the activity of suppressing interferon production in a concentration-dependent manner.

Mouse bone marrow cells cultured as in Example 2 were dispensed into round-bottomed 96-well plates at $1 \times 10^5$ cells/well. SNK01 antibody or the control antibody rat IgG was added to each well, the plates were incubated at 37° C. for 30 minutes, then influenza virus PR8 was added and the cells were cultured at 37° C. for 24 hours. IFNα in the culture supernatant was measured using the ELISA described above in Example 4 (FIG. 4). The results showed that SNK01 suppressed IFNα production in a concentration-dependent manner. Specifically, the effect of the antibody on mouse IPCs is thought to be a specific effect.

Example 6

Cloning of Molecules Recognized by the Antibodies (1) Preparation of an IPC cDNA Library IPCs were derived from bone marrow cells using FLT-3 ligand as in Example 2. Total RNAs were extracted from these IPCs by the phenol-guanidine method, and the mRNAs were purified using oligo-dT columns. cDNAs were synthesized from the purified mRNAs using the Gubler-Hoffman method. After EcoRI-NotI adapter (Invitrogen) was bound to both ends, unreacted EcoRI adapter and short cDNAs of 500 nucleotides or less were removed using a spin column (Chroma Spin 400, Clontech). The yielded cDNAs with EcoRI sites at both ends were bound to the EcoRI site of animal cell expression vector pME18s (from which the XhoI fragment was removed) using T4 ligase, and *E. coli* DH10 (Invitrogen) were transformed with this construct using electroporation. The *E. coli* were cultured in 500 ml of LB media containing 100 µg/ml carbenicillin (LB/carbenicillin) at 30° C. overnight. The plasmids were extracted and purified using a QIA Filter Plasmid Maxi kit (Qiagen) as per its protocol, and an IPC cDNA library was obtained.

(2) Expression Cloning Using COS7 Cells

COS7 cells were plated in ten 6-cm dishes at $5 \times 10^5$ cells/dish, and cultured at 37° C. under 5% $CO_2$ for 20 hours. Using Effectene Transfection Reagent (Qiagen) as per its protocol, the cells were transfected with the IPC cDNA library yielded as described above in (1). After 48 hours of culture at 37° C. under 5% $CO_2$, the cells were washed with Phosphate Buffered Saline (PBS), and then detached from the dishes with PBS/5 mM EDTA. After further washing with PBS, the cells were passed through Cell Strainers (70 µm, Falcon). The supernatants were removed by centrifugation (at 1300 rpm for five minutes). The cells were suspended in 1 ml of PBS/0.5% BSA/2 mM EDTA, 40 µl of Fc block (Pharmingen) was added to the cells, and this was stood at 4° C. for 20 minutes. 30 µg to 50 µg of biotinylated SNK01 antibody was added to this mixture, and this was incubated on ice for 30 minutes. After washing with PBS, the cells were suspended in 100 µl of PBS and 10 µl to 20 µl of streptavidin micro beads (Miltenyi Biotec) was added thereto. The mixture was allowed to stand at 10° C. for 15 minutes. Excess streptavidin micro beads were removed by washing with PBS/0.5% BSA/2 mM EDTA, and the cells were suspended in 1 ml of PBS/0.5% BSA/2 mM EDTA. The cells were then fractionated by AutoMACS (Miltenyi Biotec) under posselds conditions. The plasmids were extracted and purified using a modified Hirt method (BioTechniques Vol. 24, 760-762, 1998). *E. coli* DH10 were transformed with the yielded plasmids using electroporation, and were then cultured in 100 ml of LB/carbenicillin at 30° C. overnight. The plasmids were extracted and purified using a QIA Filter Plasmid Midi kit (Qiagen) as per its protocol.

The same procedure as described above was repeated four times to enrich plasmids encoding the antigen that reacted to SNK01 antibody. Finally, positive cells were fractionated using a cell sorter (FACSVantage; Becton Dickinson) instead of AutoMACS, and plasmids were extracted from these cells, transformed into *E. coli* DH10, and an adequate number of the cells were spread onto LB/carbenicillin plates. The plates were cultured at 30° C. overnight, 30 formed colonies were selected, and plasmids were extracted from each. COS7 cells were transfected with these plasmids, and positive plasmids were selected by FACS analysis using SNK01 antibody.

The nucleotide sequences of cloned cDNAs in the yielded plasmids were determined, and the genes were identified by using a blast search and nucleotide sequence information recorded in a mouse gene database. Further, at the same time, human counterpart genes were identified by searching a human gene database.

The results showed that clones to which monoclonal antibody SNK01 bound comprise the nucleotide sequences of SEQ ID NOs: 7 and 9. The amino acid sequences encoded by these nucleotide sequences are shown in SEQ ID NOs: 8 and 10. The nucleotide sequence of SEQ ID NO: 9 was the nucleotide sequence known as mouse BST2 (GenBank Acc#. BC027328). Meanwhile, the nucleotide sequence of SEQ ID NO: 7 comprises a nucleotide sequence partially identical to the nucleotide sequence of SEQ ID NO: 9, but a different nucleotide sequence was observed at its 3' end, and thus its encodes a different amino acid sequence. Specifically, the amino acid sequence from the N terminus to position 139 of the amino acid sequence of SEQ ID NO: 8 was identical to the amino acid sequence of SEQ ID NO: 10. The amino acid sequence from position 140 to 178 from the N terminus in the amino acid sequence of SEQ ID NO: 8 was unique to the amino acid sequence of SEQ ID NO: 8. The two sequences were thought to be variants caused by alternative splicing. Based on these findings, the protein comprising the amino acid sequence (SEQ ID NO: 8) encoded by the nucleotide sequence of SEQ ID NO: 7 was thought to be a novel splicing variant of mouse BST2. Hereinafter, the genes comprising the nucleotide sequences of SEQ ID NOs: 7 and 9 are also referred to as mBST2H and mBST2D, respectively (FIG. 7 (*a*)).

(3) Confirmation by FACS

The plasmids yielded by the expression cloning described above were again highly purified from *E. coli* cells using QIA Filter Plasmid Midi kit (Qiagen), and COS7 cells were again transfected with the plasmids. After 48 hours, the cells were reacted with SNK01 antibody and an FITC-labeled anti-rat Ig antibody according to conventional methods. The cells were analyzed with a FACS to confirm whether or not the cDNAs cloned in the plasmids encoded the antigens.

As a result, the above monoclonal antibody SNK01 was found to bind to COS7 cells introduced with the plasmids. Thus, both of the cDNAs cloned in the plasmids were confirmed to encode antigens recognized by the monoclonal antibodies.

Example 7

Confirmation of Antibody Reactivity by Western Blotting

Western blotting was used to confirm that the above monoclonal antibodies recognized and bound to proteins comprising the amino acid sequence of SEQ ID NO: 8 or 10. The amino acid sequence of SEQ ID NO: 8 or 10 was expressed as a recombinant and tested for its reactivity to the monoclonal antibodies of the present invention. The specific procedure is as follows:

(1) Construction of pcDNA3.1-mBST2D and pcDNA3.1-mBST2H

DNAs comprising the nucleotide sequence of SEQ ID NO: 7 or 9 were amplified by PCR using plasmids (1 µg) encoding cloned mBST2D or mBST2H as templates. The nucleotide sequences of the primers used in the PCR are as follows:

```
forward primer (SEQ ID NO: 11):
5'-tttttgctagcgacggatcacatggcgccctctttctatcactatct
gcccgtgcccatggatgagatgggggggaagcaagga-3' reverse primer (SEQ ID NO: 12):
5'-tttttttctcgagtcctcaaaagagcaggaacagtgac-3'
```

The composition of the reaction mixture is as follows:
1×GC buffer I,
dNTP mix (0.25 mM),
LATaq DNA polymerase 5U (all Takara Bio)/100 µl
forward primer (1 pmol):
reverse primer (1 pmol)

After the reaction mixture was incubated at 95° C. for one minute, PCR was carried out using 25 cycles of [95° C. for 30 seconds/55° C. for 30 seconds/72° C. for 90 seconds]. Agarose gel electrophoresis was used to confirm that a DNA fragment of target size was amplified. After phenol chloroform extraction and ethanol precipitation, the collected amplification products were dissolved in 10 µl of TE buffer. This was then digested with the restriction enzymes NheI and XhoI (Takara Bio), purified by agarose gel electrophoresis using a QIAquick® column Gel Extraction Kit (QIAGEN), ethanol precipitated, and dissolved in 4 µl of TE buffer.

Meanwhile, 5 µg of expression plasmid pcDNA3.1 (Invitrogen) for mammalian cells was digested with the restriction enzymes NheI and XhoI. After CIAP (Takara Bio) treatment, the DNAs were purified by agarose gel electrophoresis, ethanol precipitated, and then dissolved in 4 µl of TE buffer. 0.5 µl of the plasmid was ligated with 2 µl of each of the above DNA fragments using a Ligation Kit ver. II (Takara Bio), and these were transformed into *E. coli* DH5.

After the *E. coli* cells were cultured on LB media (100 µg/ml ampicillin) at 37° C. overnight, several formed colonies were selected, and plasmids were extracted using a QIAprep® column Spin Miniprep kit (QIAGEN). The nucleotide sequences of the DNA fragments inserted into the extracted plasmids were determined using conventional methods. The plasmids were confirmed to comprise DNA fragments comprising nucleotide sequences encoding the amino acid sequence of SEQ ID NO: 8 or 10. The desired constructs pcDNA3.1-mBST2D and pcDNA3.1-mBST2H were thus obtained.

(2) Construction of pcDNA3.1-mBST2D-His and pcDNA3.1-mBST2H-His

A nucleotide sequence encoding His tag was added by PCR using 1 μg of pcDNA3.1-mBST2D (when constructing pcDNA3.1-mBST2D-His) or pcDNA3.1-mBST2H (when constructing pcDNA3.1-mBST2H-His) as a template. The nucleotide sequences of the primers used in the PCR are shown below. The forward primer (SEQ ID NO: 13) was used to amplify both pcDNA3.1-mBST2D-His and pcDNA3.1-mBST2H-His. The reaction mixture composition and thermal cycling profile were the same as in (1).

```
forward primer (SEQ ID NO: 13):
5'-ccagctcacccgcacccaggacagtc-3' reverse primer (for pcDNA3.1-mBST2D-His;
SEQ ID NO: 14):
5'-tttttttctcgagtcaatgatgatgatgatgatgaaagagcagaaac agtgacactttga-3' reverse primer (for pcDNA3.1-mBST2H-His;
SEQ ID NO: 15):
5'-tttttttctcgagtcaatgatgatgatgatgatggaagtctcctttt ggatcctgagctg-3'
```

Agarose gel electrophoresis was used to confirm that a DNA fragment of target size was amplified, and after phenol chloroform extraction and ethanol precipitation, this DNA was dissolved in 10l of TE buffer. After digestion with the restriction enzymes BamHI and XhoI (Takara Bio), the DNAs were purified by agarose gel electrophoresis using a QIAquick® column Gel Extraction Kit (QIAGEN), ethanol precipitated, and then dissolved in 4 μl of TE buffer.

Meanwhile, 5 μg of pcDNA3.1-mBST2D and pcDNA3.1-mBST2H were digested with the restriction enzymes BamHI and XhoI, treated with CIAP (Takara Bio), and then purified by agarose gel electrophoresis. The DNAs were ethanol precipitated, and then dissolved in 4 μl of TE buffer. 2 μl of each of the DNA fragments amplified by PCR were ligated with 0.5 μl of the plasmids described above using a Ligation Kit ver. II (Takara Bio), and thus obtained DNAs were transformed into E. coli DH5.

Several of the colonies formed by culturing the transformed bacteria on LB media (100 μg/ml ampicillin) at 37° C. overnight were selected, and plasmids were extracted using a QIAprep® column Spin Miniprep kit (QIAGEN). The nucleotide sequences of DNA fragments inserted into the extracted plasmids were determined using conventional methods. The plasmids were confirmed to comprise DNA fragments comprising nucleotide sequences encoding His tag. The desired constructs pcDNA3.1-mBST2D-His and pcDNA3.1-mBST2H-His were thus obtained.

(3) Western-Blotting

COS7 cells were plated in ten 6-cm dishes at $5 \times 10^5$ cells and cultured at 37° C. under 5% $CO_2$ for 20 hours. Using Effectene Transfection Reagent (Qiagen) as per its protocol, the cultured COS7 cells were transformed with pcDNA3.1-mBST2D-His or pcDNA3.1-mBST2H-His. The cells were cultured at 37° C. under 5% $CO_2$ for 48 hours, then washed with PBS, and harvested by detaching the cells from the dishes using PBS/5 mM EDTA. The harvested cells were further washed with PBS, then 2 ml of RIPA buffer containing 1× Halt Protease Inhibitor Cocktail (PIERCE) was added and the cells were lysed on ice for one hour. The composition of RIPA buffer is as follows:

50 mM Tris-HCl (pH 7.4)
150 mM NaCl
1% Triton X-100
0.5% sodium deoxycholate
0.1% SDS The cell lysate was centrifuged at 15,000 rpm and 4° C. for five minutes. The supernatant was concentrated to 50 μl or less using Microcon YM-10 (Millipore), and then used as a sample in Western blotting. Meanwhile, the precipitate was once again washed with 1 ml of RIPA buffer containing 1× Halt Protease Inhibitor Cocktail (PIERCE), and then used as a sample in Western blotting.

200 μl of 1× denaturation buffer was added to the precipitate, and an equal volume of 2× denaturation buffer was added to the concentrated supernatant. These samples were boiled at 100° C. for ten minutes, and then 5 μl of each sample was electrophoresed in NuPAGE4-12% Bis-Tris Gel (Invitrogen). After electrophoresis, the samples were transferred from the gel to PVDF membrane (Millipore) using a semi-dry blotting device (Biocraft; MODEL BE-330).

Figure 5:
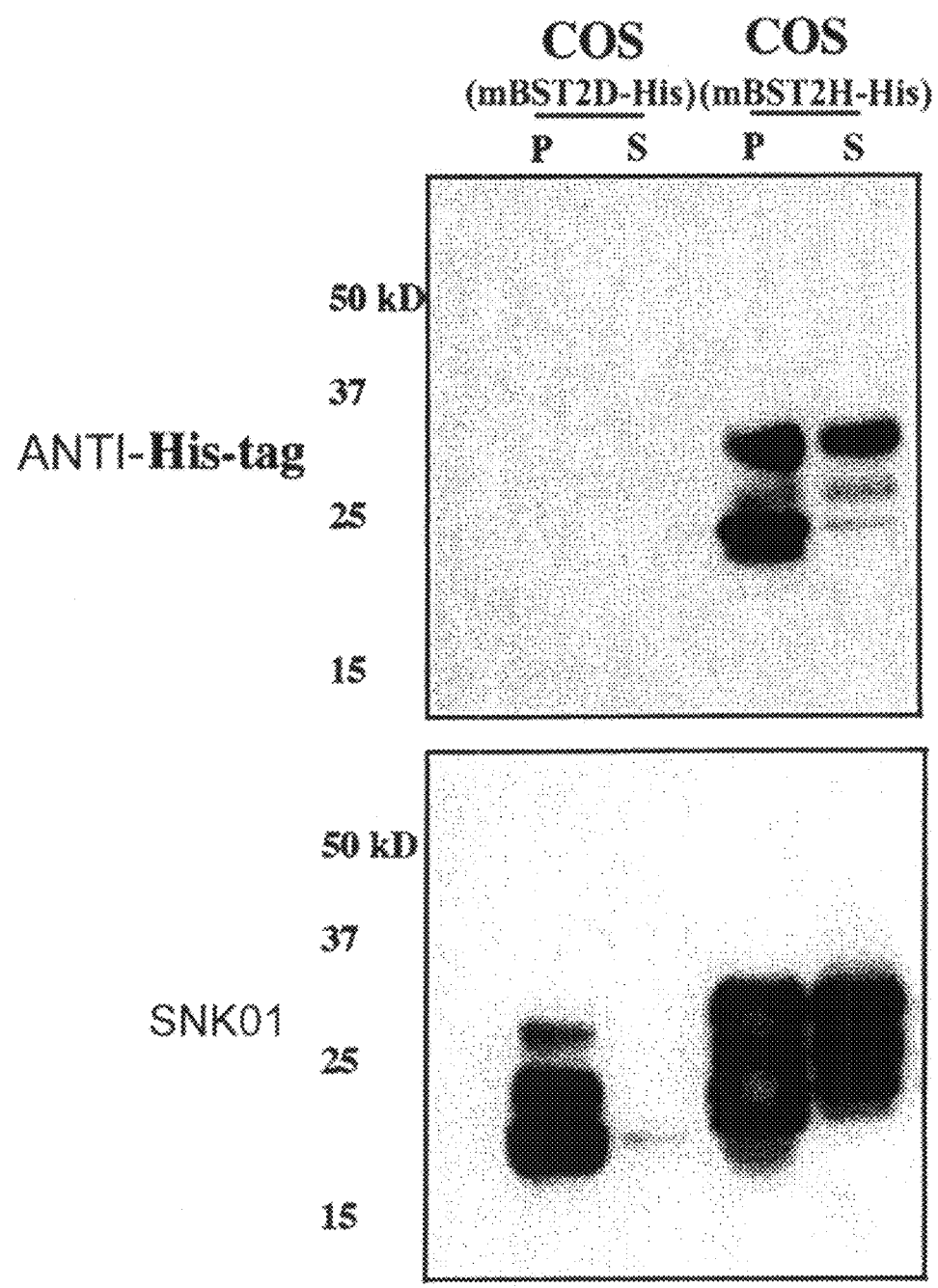
FIG. 5 is photographs showing the results of Western blotting assays using a monoclonal antibody SNK01. The upper panel shows the results obtained using an anti-His tag antibody, and the bottom panel shows the results obtained using the monoclonal antibody SNK01 of the present invention. The left lanes contain COS7 cells transfected with pcDNA3.1-mBST2Dhis and the right lanes contain COS7 cells transfected with pcDNA3.1-mBST2H-His. The results for the precipitates (P) and supernatants (S) of lysates of the cultured cells are shown.

The detection using antibodies used an ImmunoStar kit (Wako Pure Chemical Industries). First, the signal was detected using 5000 times diluted HRP-labeled anti-His tag antibody (Invitrogen) as a primary antibody, as per the ImmunoStar kit protocol. After signal detection, the PVDF membrane was shaken in a denaturation solution (containing 7 M guanidine hydrochloride, 50 mM glycine, 0.05 mM EDTA, 0.1 M potassium chloride, and 20 mM 2-mercaptoethanol) at room temperature for one hour to remove the labeled anti-His tag antibodies. The signal was then detected in the same way using biotinylated SNK01 antibody. The results are shown in FIG. 5.

In the case of monoclonal antibody SNK01, an intense band was observed at the molecular weight position (about 20 kD) predicted from the amino acid sequence. SNK01 reacted strongly with both BST2D (SEQ ID NO: 10) and BST2H (SEQ ID NO: 8). Strong signals were detected at positions for 20 kD or higher. These proteins with large molecular weights were deduced to be glycosylated. For BST2D (SEQ ID NO: 10), the precipitate gave a stronger signal than the supernatant. For BST2H (SEQ ID NO: 8), similarly, the precipitate gave a stronger signal, and a strong reaction was also detected between the supernatant and the antibody. The antibody against His tag is thought to have given no detectable signal for BST2D (SEQ ID NO: 10) because the His tag attached to the C terminus was removed by processing.

Example 8

Confirmation of Mouse BST2 Expression by RT-PCR cDNAs synthesized from RNAs extracted from each cell type were used as a template for PCR carried out by conventional methods, and the antigen genes were confirmed to be specifically expressed in IPCs. The nucleotide sequences of primers used in the PCR are as follows:

```
forward for SEQ ID NO: 7 (SEQ ID NO: 16):
5'-acatggcgccctctttctatcac-3' reverse (SEQ ID NO: 17):
5'-gagcccaggttttgaaggaagtg-3'
```

-continued

Figure 6:
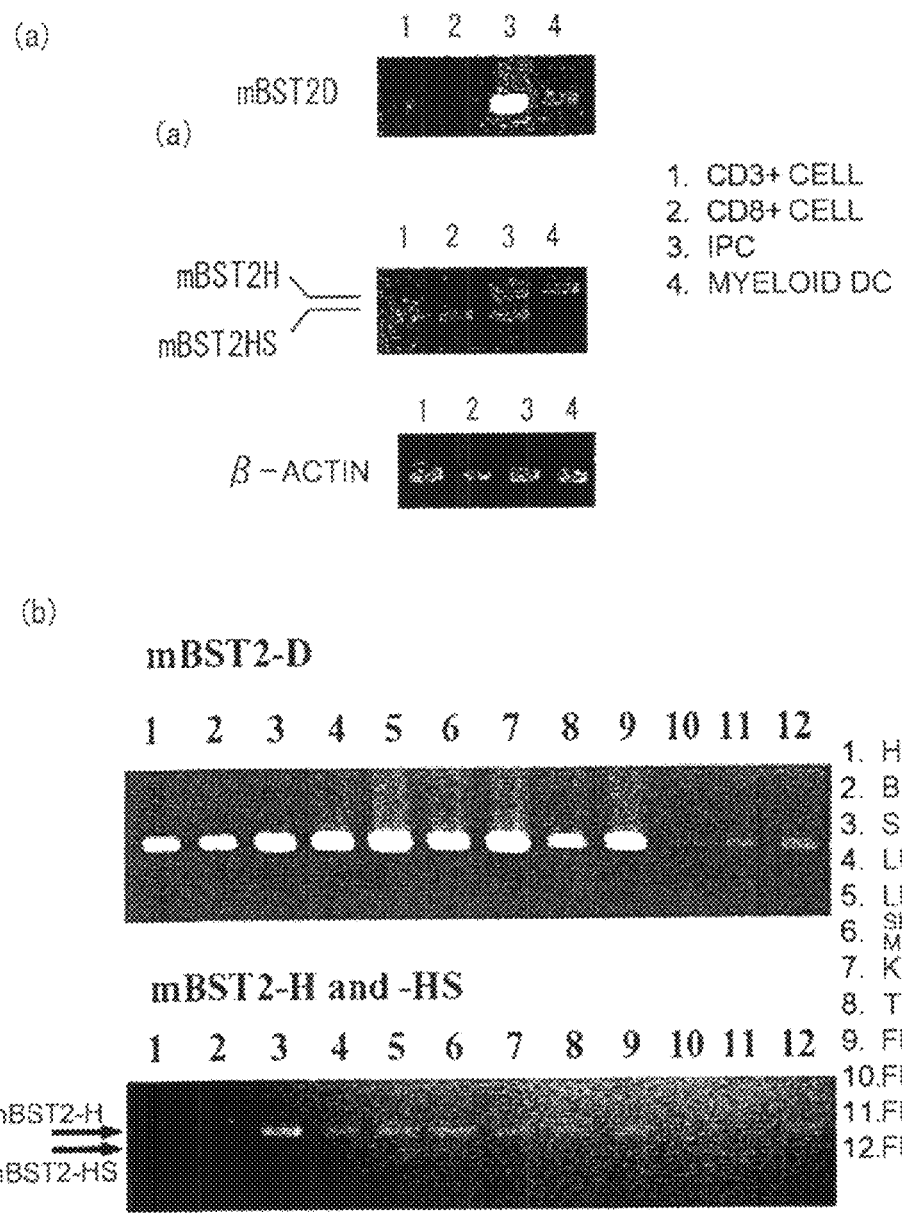
FIG. 6 is photographs showing the results of comparing the expression levels of mouse BST2 mRNA between tissues and cells. Lanes show each of the analyzed tissues and cells.

```
forward for SEQ ID NO: 9 (SEQ ID NO: 18):
5'-agctcacccgcacccaggacagt-3' reverse (SEQ ID NO: 19):
5'-cactccccagtcctaaagttct-3' sense primer for β-actin (SEQ ID NO: 20):
5'-gtgggccgctctaggcaccaa-3' antisense primer (SEQ ID NO: 21):
5'-ctctttgatgtcacgcacgatttc-3'
``` cDNAs and cells used to compare expression levels are listed below. A commercially available DNA panel (Clontech) was used. The cells used were highly separated using a cell sorter (FACSVantage, Becton Dickinson). The results are shown in FIG. 6. BST2D (SEQ ID NO: 9) was found to be expressed in multiple cell types. IPCs were revealed to express BST2D at high levels. BST2H (SEQ ID NO: 7) was found to be highly expressed in mouse IPCs.

CD3-positive cells (T cells)
CD8-positive cells
mouse IPCs
myeloid DCs; and
cDNA panels synthesized from RNAs extracted from each mouse organ

Example 9

Cloning of Novel Splicing Variants of Mouse BST2

In addition to the amplified fragment corresponding to the cDNA of SEQ ID NO: 7 detected using the primer pair for SEQ ID NO: 7 in Example 8, a shorter amplified fragment was also detected. This amplified fragment was cloned and its nucleotide sequence was confirmed using conventional methods. It was found to comprise an mBST2H nucleotide sequence where the second exon is deleted from the sequence of SEQ ID NO:7. Specifically, it was thought to be a novel splicing variant of mouse BST2, comprising the nucleotide sequence of SEQ ID NO: 22. The amino acid sequence encoded by this gene is shown in SEQ ID NO: 23. As shown in Example 8, this gene was also confirmed to be expressed in mouse IPCs. Hereinafter, genes for SEQ ID NO: 22 are also referred to as mBST2HS.

An alignment of the amino acid sequences of mBST2D, mBST2H, and mBST2HS is shown in FIG. 7 (a); each genomic structure is shown in FIG. 7 (b).

Example 10

Preparation of Expression Vector for Mouse BST2

PCR was carried out under the conditions described below using the mBST2D and mBST2H cDNAs obtained as described in Example 6 as templates, and primers comprising the following nucleotide sequences:

```
pmBST2-F:
                                           (SEQ ID NO: 24)
tttttgctagcgacggatcacatggcgccctctttctatcactatctgcc cgtgcccatggatgagatggggggaagcaagga
and pmBST2-R:
                                           (SEQ ID NO: 25)
ttttttctcgagtcctcaaaagagcaggaacagtgac
```

DNA polymerase: LA Taq (Takara Bio)
25 Cycles of [95° C. For 30 Seconds, 55° C. For 30 Seconds, and 72° C. For Two Minutes]

Each expression vector was prepared by digesting each of the amplified fragments with the restriction enzymes NheI and XhoI (both Takara Bio), and then ligating them with animal cell expression vector pcDNA3.1-Zeo(+) (Invitrogen), which had been treated with NheI and XhoI in the same way, using a ligation kit ver. II (Takara Bio). The expression vector for mBST2HS was prepared by removing the second exon from mBST2H using PCR according to conventional methods.

Example 11

Cloning of Human Orthologue cDNAs and Preparation of Expression Vectors

A search for the human orthologue of mouse IPC-specific antigen BST2, identified in the present invention, turned up the known gene reported as human BST2 (Ishikawa, J. et al. Genomics, 1995; 26, 527-; GenBank Acc#. D28137). Further, genes comprising the human orthologues of the novel splicing variants identified in mouse were also cloned by PCR as described below. Three types of expression vectors were constructed.

Human IPCs stimulated with Herpes Simplex virus were prepared according to the method described in the Examples below. After RNA extraction, the first strand of a cDNA was synthesized using a Superscript First Strand System kit (Invitrogen). PCR was carried out using this strand as a template, and LA Taq (Takara Bio) as an enzyme, and hBST2 primer F: aaaaaaagctagctggatggcatctacttcgtatg (SEQ ID NO: 26) and hBST2 primer R: aaaaaaactcgagacccataacaacaggcagcacat (SEQ ID NO: 27) (25 cycles of: 95° C. for 30 seconds, 55° C. for 30 seconds, and 72° C. for two minutes). The amplified fragment was digested with the restriction enzymes NheI and XhoI, and then inserted into the NheI and XhoI sites of pcDNA3.1-Zeo(+) (Invitrogen) to construct an expression plasmid for human BST2.

The orthologue genes of the mouse splicing variants were amplified by PCR (25 cycles of: 95° C. for 30 seconds, 55° C. for 30 seconds, and 72° C. for two minutes) using an IPC cDNA library as a template and LA Taq (Takara Bio) as an enzyme, with primers comprising the nucleotide sequences shown below. The cDNAs were synthesized using a GeneRacer kit (Invitrogen). The amplified fragments were digested with the restriction enzymes NheI and XhoI, and then inserted into NheI and XhoI sites of pcDNA3.1-Zeo(+) (Invitrogen) to construct an expression plasmid.

```
<primers for mBST2H orthologue>
hBST2 primer F (SEQ ID NO: 26) and primer hBHR:
                                           (SEQ ID NO: 28)
tttttctcgagctagggatgtgggggtgagaggaatgtggcaggtggag ggtagcgggggaaggctatctctgacctcagtcgctccacctctgcagac <primers for mBST2HS orthologue>
hBST2 primer F (SEQ ID NO: 26) and primer
hBST2HSR1:
                                           (SEQ ID NO: 29)
aaaaaaactcgagcttatggtttaatgtagtgatctctccacagtgtggt tgcaggtggcggcct
```

The nucleotide sequence of human BST2, which is a known gene, is shown in SEQ ID NO: 1; its amino acid sequence is shown in SEQ ID NO: 2. Hereinafter, genes comprising this sequence are also called hBST2D. Further, the nucleotide sequence of the human orthologue of mBST2H obtained as described above (hereinafter also referred to as hBST2H) is shown in SEQ ID NO: 3, and the amino acid sequence is shown in SEQ ID NO: 4. The nucleotide sequence of the human orthologue of mBST2HS (hereinafter also referred to as hBST2HS) is shown in SEQ ID NO: 5, and the amino acid sequence is shown in SEQ ID NO: 6.

Figure 8:
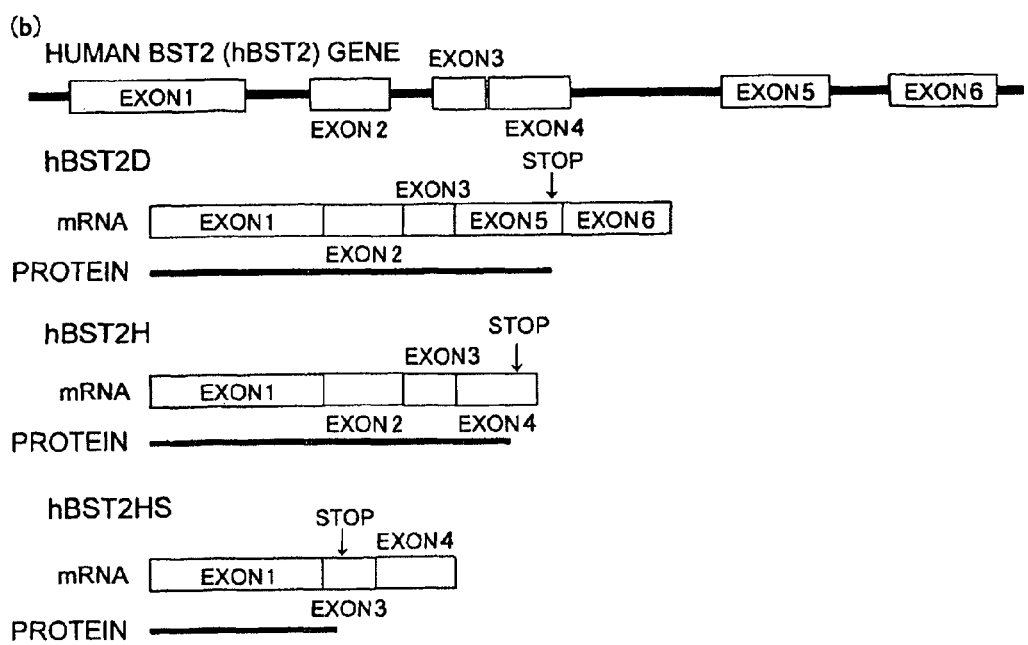
FIG. 8 is diagrams showing the amino acid sequences and genomic structures of human BST2 and homologues thereof. (a) shows an alignment of the amino acid sequences of each of the isoforms. (b) shows exon maps.

An alignment of the amino acid sequences of hBST2D, hBST2H, and hBST2HS is shown in FIG. 8 (*a*), and each genomic structure is shown in FIG. 8 (*b*). hBST2H and hBST2HS were suggested to be novel splicing variants.

Example 12

Confirmation of the Expression of Human BST2 Gene by RT-PCR cDNAs were synthesized from RNAs extracted from each cell type. PCR was carried out using conventional methods to examine the expression of each variant of human BST2. The PCR conditions were: incubation at 95° C. for one minute, followed by 30 cycles of [95° C. for 30 seconds, 60° C. for 30 seconds, and 73° C. for 45 seconds] for type D; and 35 cycles of the same for types H and HS (FIG. 9).

The sequences of the primers are as follows:

```
Forward primer:
                                           (SEQ ID NO: 30)
gccttcgggcagtgatggagtgtc Reverse primer for D:
                                           (SEQ ID NO: 31)
tcaagcgaaaagccgagcaggac Reverse primer for H and HS:
                                           (SEQ ID NO: 32)
aatgtggcaggtggagggtag
```

The results showed that human BST2 mRNA was expressed in multiple tissues and cell types. In addition, expression in IPCs was found to be enhanced by HSV stimulation.

Example 13

Preparation and Evaluation of Antibodies Recognizing Mouse BST2

(1) Preparation of Anti-Mouse BST2 Antibodies

Antibodies which recognize one or more of the three subtypes of mouse BST2—D, H, and HS—were prepared as described below:

COS7 cells were plated in five 6 cm dishes at $4 \times 10^5$ cells/dish. After 20 hours of culture, Effectene Transfection Reagent (Qiagen) was used as per its protocol to transfect the cells with a mixture of equal amounts (1 µg/dish) of the three types of expression vectors carrying each type of cDNA prepared above in Example 10. After 24 hours, the medium was exchanged for fresh medium. After another 24 hours, the cells were harvested using PBS/5 mM EDTA, washed with PBS, and then injected in combination with adjuvant CFA into both foot pads of Wister rats (five or six weeks old). This procedure was carried out on days zero, four, and eleven, and lymph nodes were excised from the immunized rats on day 12. Hybridomas were prepared by the same method as described in Example 1. Clones that reacted with COS7 cells transfected with the three types of expression vectors, but not to host COS7 cells, were selected by using Cell ELISA to screen the culture supernatants of the hybridomas. Furthermore, binding activity was also confirmed by FACS analysis, cell cloning was carried out, and five positive clones were finally yielded.

(2) Influence on the Ability to Produce Mouse IFNs

The influence on IFN production was examined using culture supernatants of the yielded clones according to the method described in Example 5. All culture supernatants had the activity of suppressing IFN production in IPCs as compared with a control antibody. Furthermore, when stimulated with 0.1 µM CpG ODN 1668 (MWG Biotech), the supernatants exhibited the activity of suppressing IFN production (FIG. 10). These results confirmed that anti-mBST2 antibodies other than SNK01 also exhibited the activity of suppressing IFN production in IPCs.

Example 14

Preparation and Evaluation of Antibodies Recognizing Human BST2 (hBST2)

(1) Preparation of Human BST2 Antibodies

Antibodies which recognize one or more of the three subtypes of human BST2—D, H, and HS—were prepared by the same method as described in Example 13. The hybridomas were screened by FACS analysis of the culture supernatants, using the three types of expression vectors carrying each type of human cDNA, prepared in Example 11. Multiple clones were yielded, including clone 3D3#7 that reacts only with hBST2H; clones 3E2#8 and 5C11#7 that react with both hBST2H and hBST2D; and clone 3G7#6 that reacts with all hBST2H, hBST2D, and hBST2HS. Antibodies were purified using the yielded multiple clones and further analyzed.

(2) Influence on the Ability to Produce Human IFNs

Figure 11:
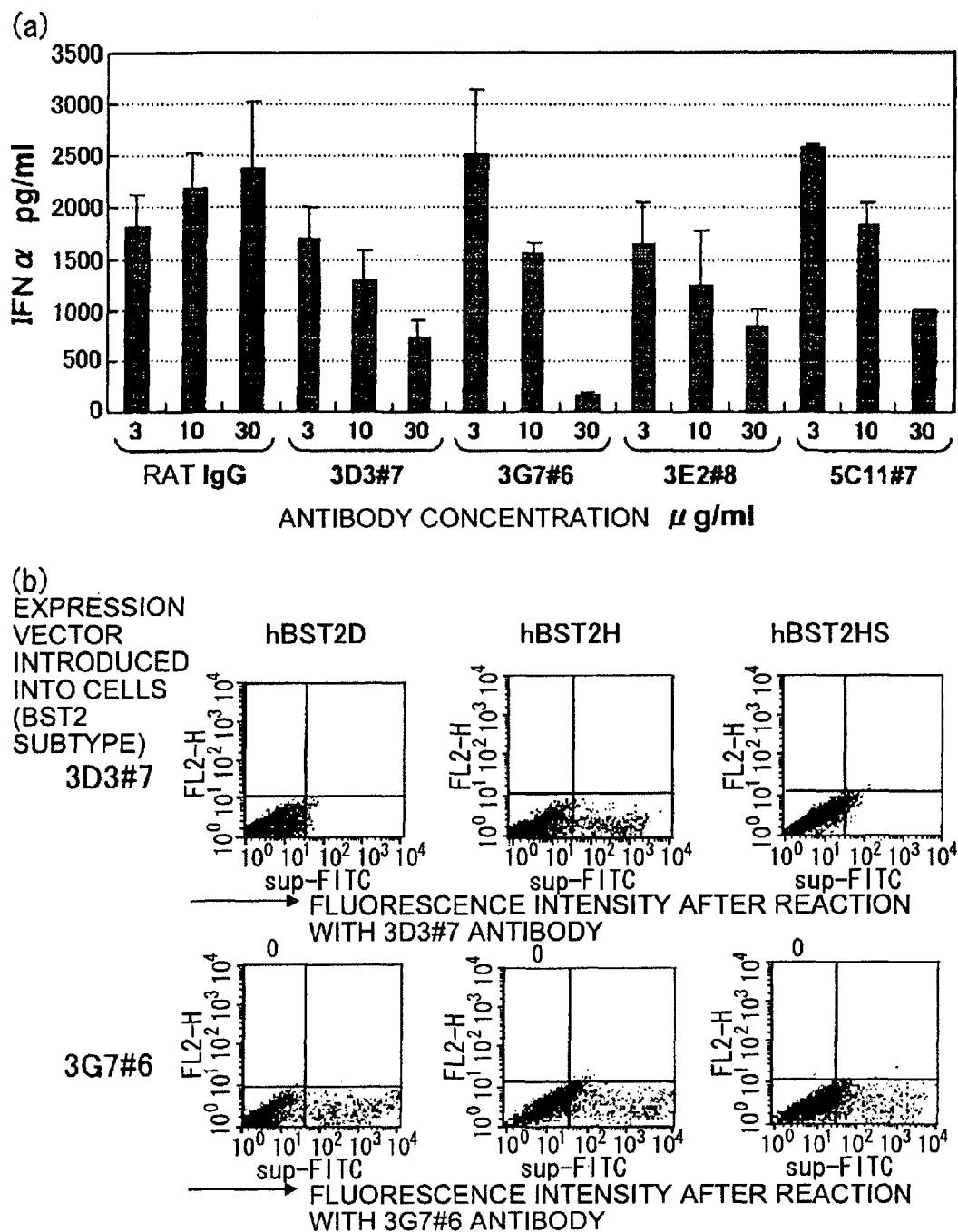
FIG. 11 is graphs showing the influence of prepared anti-human-BST2 monoclonal antibodies on interferon-producing ability. (a) is a graph showing the influence on interferon-producing ability; the horizontal axis indicates the types and concentrations of antibodies used in the treatment, the vertical axis indicates the IFNα concentration (pg/ml) in the culture supernatant when human IPCs were stimulated with HSV. (b) shows the results of analyzing the reactivities of clones 3D3#7 and 3G7#6 with the BST2 subtypes.

Peripheral blood was collected from normal subjects, and peripheral blood lymphocytes (PBLs) were separated. Various cells were removed by MACS using lineage antibodies (CD3, CD14, CD16, CD19, CD20, and CD56 antibodies). A CD4-positive, CD123-positive, lineage-negative cell population was separated as IPCs by fractionation using a cell sorter. Human IPCs prepared in this way were plated in 96-well plates at $2 \times 10^4$ cells/well. An anti-BST2 antibody was added to each well at 3, 10, or 30 µg/ml, and the cells were incubated at 37° C. for one hour. After one hour of incubation, Herpes Simplex virus (20 pfu/cell) was added, and the cells were cultured at 37° C. for 24 hours. The IFNα in the culture supernatants was measured using an ELISA kit (Bender Med System). The results showed that like the previously reported BDCA2 antibody (Miltenyi), the anti-human BST2 antibodies exhibited the activity of suppressing human IFN production (FIG. 11*a*). Clone 3D3#7 reacted with hBST2H; clone 3G7#6 reacted with all of hBST2H, hBST2D, and hBST2HS (FIG. 1*b*). Thus, antibodies recognizing human BST2 were found to influence the IFN-producing activity of IPCs.

Example 15

Expression Pattern of BST2 Proteins (1) Expression Pattern of Mouse BST2

Figure 12:
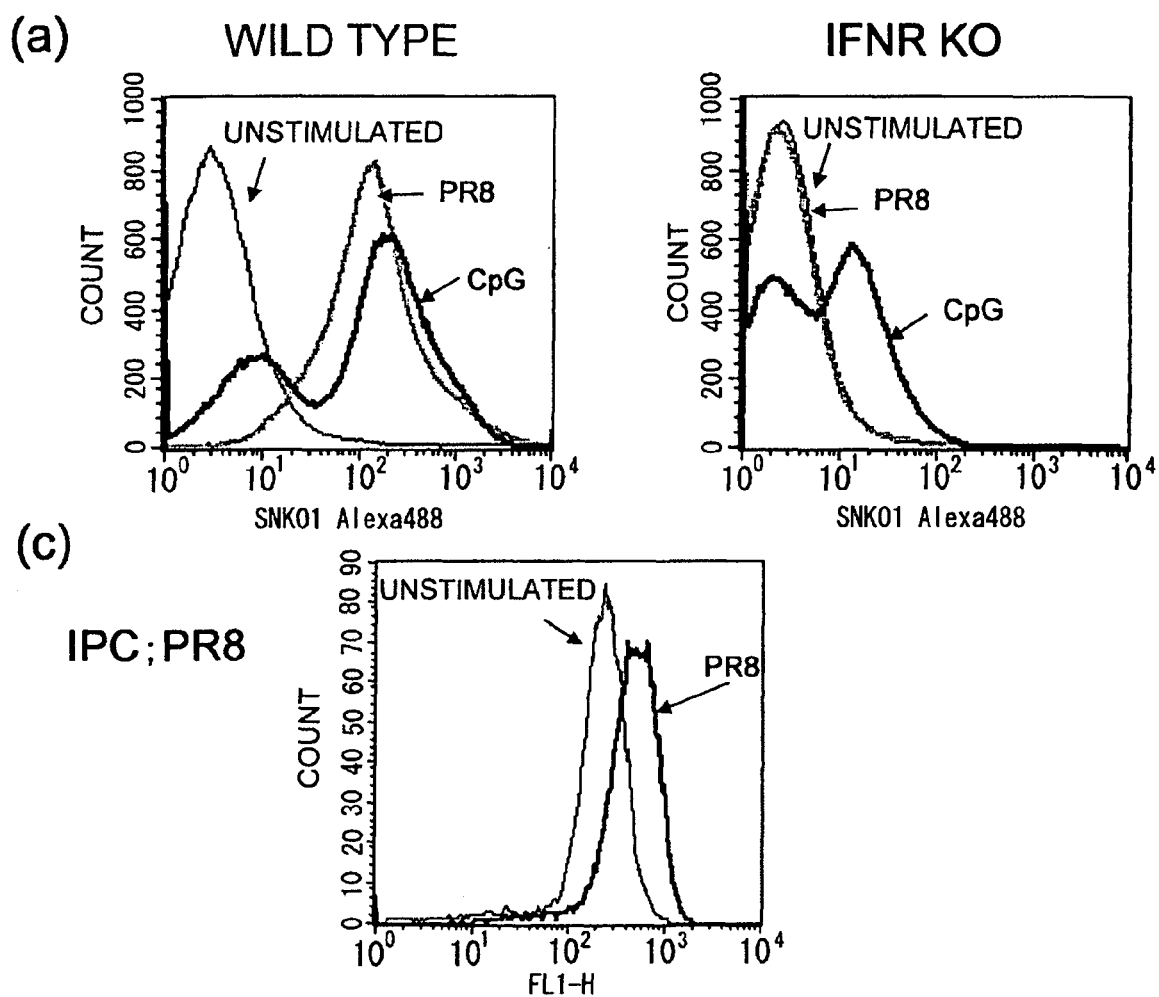
FIG. 12 shows the results of stimulating various cells of wild-type mice (WT) or IFN receptor-knockout mice (IFNR-KO) with CpG or influenza virus PR8, and then staining the cells with SNK01 antibody labeled with fluorescent dye Alexa488. The horizontal axes indicate the fluorescence intensity of SNK01, namely the BST2 expression level, and the vertical axes indicate cell count. (a) shows the analysis of the whole spleen cells; (b) shows the analysis of each cell type after fractionation; and (c) shows the analysis of the IPC fractionation.

The expression of mouse BST2 protein was analyzed by FACS using monoclonal antibody SNK01. Spleen cells from Balb/c mice or Type I IFN receptor-knockout mice were stimulated with CpG (0.5 µM) or influenza virus PR8 for 24 hours, then stained using various antibodies. In their usual unstimulated condition, BST2 was specifically expressed in IPCs, as shown in FIG. 1; however, stimulation was found to induce the expression of BST2 in many cell types of Balb/c mice (FIG. 12). Similar tendencies were also found in CD3-positive T cells, CD19-positive B cells, DX5-positive NK cells, and Gr-1-positive granulocytes. Furthermore, since neither CpG nor the virus enhanced the expression of BST2 in IFNR-knockout mice, BST2 expression was inferred to be induced via IFN signals.

(2) Expression Pattern of Human BST2

Figure 14:
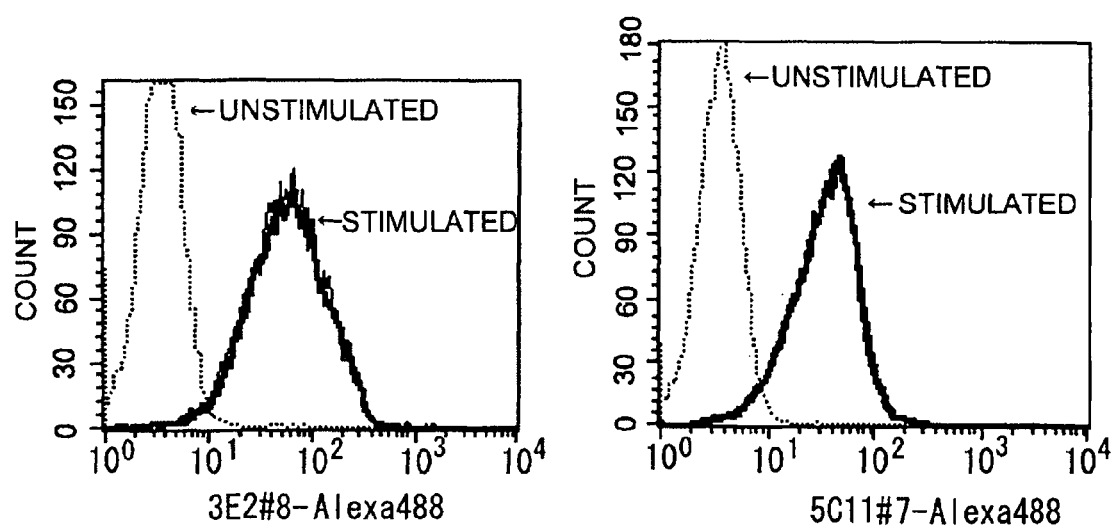
FIG. 14 is graphs showing the analysis of BST2 expression in human IPCs stimulated with CpG. The horizontal axes indicate the fluorescence intensities for anti-human-BST2 antibodies 3E2#8 and 5C11#7, namely, the BST2 expression level. The vertical axes indicate cell count. Thick and dotted curves indicate the patterns for CpG-stimulated and unstimulated human IPCs, respectively.

The expression of human BST2 protein was analyzed by FACS using antibody 5C11, prepared in (1) of Example 14. PBLs were collected from the peripheral blood of normal subjects, and IFNα was added at a concentration of 1 ng/ml. The cells were cultured at 37° C. for 24 hours, and then double-stained with 5C11 and an anti-BDCA-2 antibody or anti-BDCA-4 antibody (FIG. 13). The results showed that BST2 expression in human IPCs was usually undetectable, but was induced by IFN stimulation. Specifically, as in mice, the expression of BST2 in humans was found to be induced by IFNs, and IFN production itself was also influenced by IFNs. Further, expression in IPCs was also found to be induced upon stimulation with CpG (FIG. 14).

Example 16

Figure 15:
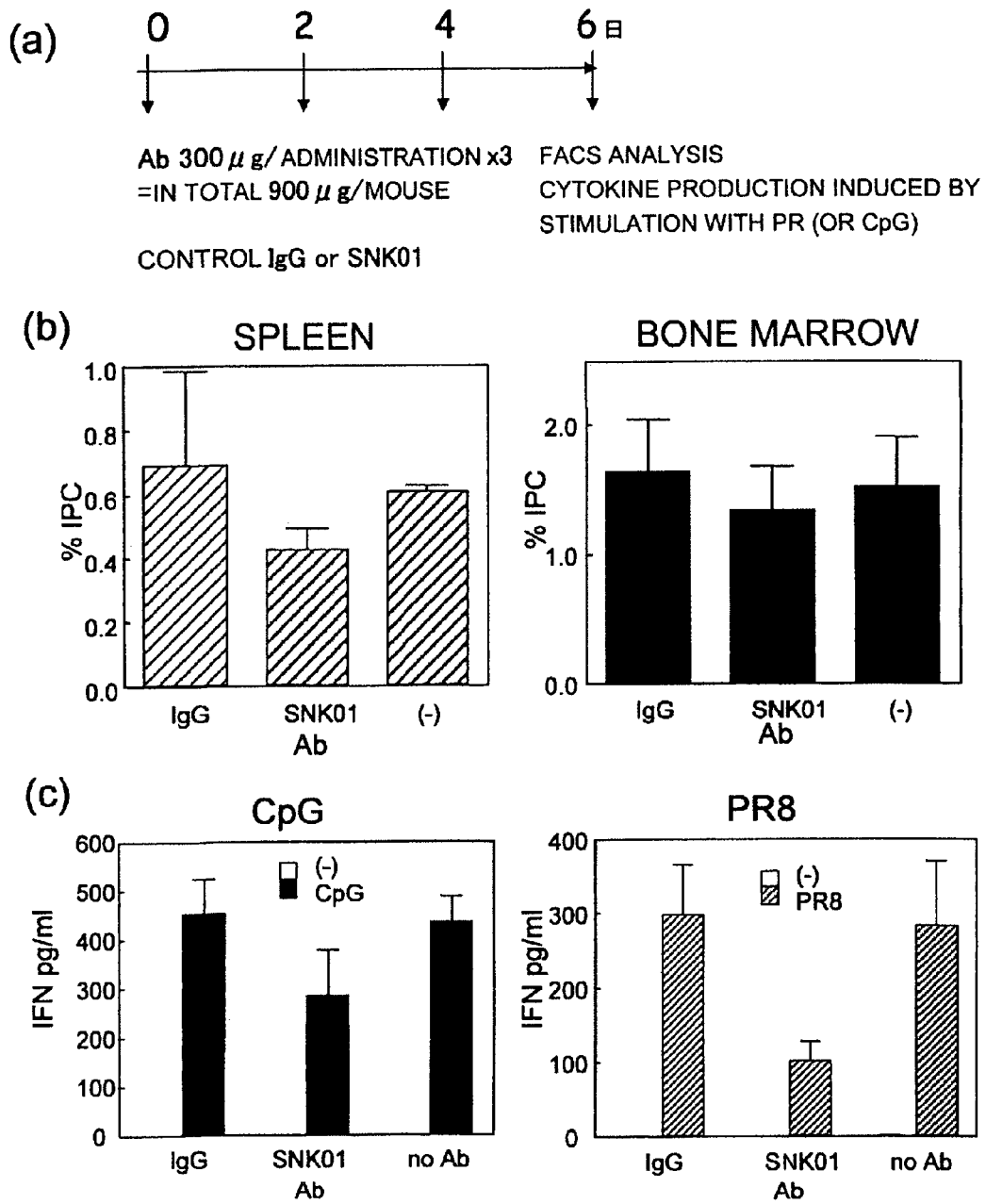
FIG. 15 shows analyses of cells collected from mice administered with an anti-mouse-BST2 antibody SNK01. (a) shows the schedule of administration. (b) shows the IPC proportion in each organ. The horizontal axes indicate the antibodies administered, and the vertical axes indicate the IPC proportion. (–) indicates groups administered with PBS alone instead of the antibodies. (c) shows the concentration of IFNs produced by bone marrow cells upon stimulation with CpG or influenza virus PR8. The horizontal axes indicate the antibodies administered.

In Vivo Evaluation of Antibodies (1) Analysis of Cells Collected from Mice Administered with Antibodies 300 μg/mouse of SNK01 or of control rat IgG was administered into the peritoneal cavity of Balb/c mice, every second day for three times in total (0.9 mg/mouse). On day 6 the spleen and bone marrow were excised, and the abundance of IPCs was analyzed by staining with B220, CD11c, and CD11b. Bone marrow cells were then plated in 96-well plates at $1 \times 10^6$ cells/well, and simulated with CpG (0.5 μM) or influenza virus PR8. After 24 hours, the concentrations of cytokines in the culture supernatants were determined by ELISA (FIG. 15).

The results showed that the IFN-producing ability after each stimuli was low in the SNK01-administered group. There was no influence on the production of IL-12. This showed that the administration of this antibody caused changes in the function of cells expressing the molecule, and suppressed IFN-producing ability due to in vitro stimulation.

(2) Analysis Using Virus-Infected Mice

Antibodies were administered to mice (n=3) at a dose of 500 μg/mouse prior to 1.5 and 0.5 days. These mice were infected by administration of $5 \times 10^4$ pfu/mouse of mouse cytomegalovirus (MCMV) into the peritoneal cavity. On day 1.5 after infection, IFNα in mouse sera was measured using ELISA. In addition, the abundance of IPCs in the spleen was analyzed using B220, CD11c, and CD 11b staining (FIG. 16).

The results showed that the level of IFNs produced in the serum was suppressed in the SNK01-administered group. There was no influence on TNFα production. Specifically, in vivo administration of this antibody was shown to suppress IFN-producing ability. Binding of the antibody to the cells was thought to regulate the cell function.

(3) Analysis of the Cells of Antibody-Administered Mice

SNK01, anti-mouse BST2 antibody clone #12 prepared in Example 13, or rat IgG (control), were each administered at 500 μg/mouse into the peritoneal cavity of Balb/c mice (n=3). After 24 hours, the abundance of IPCs in each organ was analyzed by FACS. In this case, staining was carried out using an anti-CD 11c antibody (Becton Dickinson) and SNK02 antibody, an IPC-specific antibody prepared by the method described in Example 1. The results showed that IPCs were reduced in the peripheral blood, spleen, lymph nodes, and bone marrow in the group administered with the anti-mouse BST2 antibody (FIG. 17). Large changes in the numbers of T cells and B cells were not detectable in the lymph nodes. Thus, the antibody was shown to regulate IPC activity.

INDUSTRIAL APPLICABILITY

The present invention provides agents and methods for regulating IPC activity. IPCs include cells that produce several thousand times more IFNs than other cells. Therefore, IFN production can be effectively suppressed by suppressing either or both of the ability to produce IFNs and cell survival (or the number of cells). The overproduction of type 1 IFNs by IPCs has been shown to be closely associated with mechanisms underlying the onset of autoimmune diseases. Thus, the agents and methods for regulating IPC activity, which are provided by the present invention, can be used to treat autoimmune diseases.

BDCA-2-, BDCA-4-positive cells have also been reported to cause leukemias (Jacob, M C. et al. Haematologica 88: 941-955, 2003; Chaperot L. et al. Eur. J. Immunol. 34: 418-426, 2004). There is a possibility that cancerous cells involved in such leukemias can be directly suppressed based on the present invention. Thus, the agents of the present invention for suppressing IPC activation are useful as agents for suppressing cancer cells comprising cells that express BST2 or its homologues.

The present invention also provides uses of BST2 and its homologues as markers for IPC activation. In vivo IPC activation implies the triggering of increased production of type 1 IFNs. Thus, BST2 and its homologues are useful, for example, as detection markers or diagnostic indicators for autoimmune diseases caused by IFNs. IPCs are activated in the early phase of viral infection. Thus, IPC activation can also be used as a marker for determining the possibility of viral infection at such an early phase of viral infection that antibodies against the viruses are undetectable in the blood. The level of in vivo IPC activation is clinically important information in every situation.

Furthermore, test compounds can be evaluated for their activity in regulating the activated state of IPCs by using as an indicator the expression levels of BST2 and its homologues in cultured cells. Specifically, compounds for regulating IPC activation can be screened by using the expression levels of BST2 and its homologues as an indicator. Compounds detectable using screening methods based on the present invention are also useful as agents or in methods for regulating IPC activities. Such compounds can be used as therapeutic agents for autoimmune diseases.

The invention claimed is:

1. A method for suppressing an activity of an activated interferon-producing cell, which comprises the step of contacting the activated interferon-producing cell with an antibody that binds bone marrow stromal cell antigen 2 (BST2), thereby suppressing the activity of the activated interferon-producing cell.

2. The method of claim 1 for suppressing an activity of an activated interferon-producing cell, wherein the activity of the activated interferon-producing cell is either or both of the activity of producing interferon or survival of the activated interferon-producing cell.

3. The method of claim 1, wherein the contact is achieved by administering the antibody to a subject in need thereof.

4. The method of claim 1, wherein the antibody is an antibody against a protein comprising the amino acid sequence of any one or more of SEQ ID NO: 2, 4 or 6.

5. The method of claim 4, wherein the antibody binds a region comprising the amino acid sequence of position 139 to 158 from the N terminus of the amino acid sequence of SEQ ID NO: 4.

6. The method of claim 4, wherein the antibody binds a region comprising the amino acid sequence of position 96 to 100 from the N terminus of the amino acid sequence of SEQ ID NO: 6.

7. The method of claim 4, wherein the antibody is a monoclonal antibody.

8. The method of claim 1, wherein the antibody is produced by the hybridoma 3D3#7 deposited under FERM BP-10339 or the hybridoma 307#6 deposited under FERM BP-10340, or a fragment thereof comprising an antigen-binding domain.

9. The method of claim 1, wherein the BST2 is a human or mouse BST2.

10. The method of claim 9, wherein the BST2 is a human BST2.

11. The method of claim 1, wherein the activated interferon-producing cell is a precursor cell of a dendritic cell.

12. The method of claim 1, wherein the antibody is an antibody that binds BST2 and that binds to the activated interferon-producing cell, thereby allowing the antibody to effectively suppress the activity of the activated interferon-producing cell.

13. A method for suppressing an activity of an activated interferon-producing cell, comprising the steps of:
   (1) identifying an activated interferon-producing cell; and
   (2) contacting the activated interferon-producing cell with an antibody that binds bone marrow stromal cell antigen 2 (BST2), thereby suppressing the activity of the activated interferon-producing cell.

14. The method of claim 13, wherein the identification comprises determining the level of bone marrow stromal cell antigen 2 (BST2).

15. The method of claim 13, wherein the identification comprises determining the level of interferon produced by the interferon-producing cell.

* * * * *

UNITED STATES PATENT AND TRADEMARK OFFICE
CERTIFICATE OF CORRECTION

| | | |
|---|---|---|
| PATENT NO. | : 8,435,530 B2 | Page 1 of 1 |
| APPLICATION NO. | : 11/629045 | |
| DATED | : May 7, 2013 | |
| INVENTOR(S) | : Jun Ohkawa | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1582 days.

Signed and Sealed this
Twenty-fourth Day of June, 2014

Michelle K. Lee
*Deputy Director of the United States Patent and Trademark Office*

SEQUENCE LISTING

<160> NUMBER OF SEQ ID NOS: 32

<210> SEQ ID NO 1
<211> LENGTH: 866
<212> TYPE: DNA
<213> ORGANISM: Homo sapiens
<220> FEATURE:
<221> NAME/KEY: CDS

<222> LOCATION: (4)..(546)
<223> OTHER INFORMATION:

<400> SEQUENCE: 1

```
tgg atg gca tct act tcg tat gac tat tgc aga gtg ccc atg gaa gac      48
    Met Ala Ser Thr Ser Tyr Asp Tyr Cys Arg Val Pro Met Glu Asp
    1               5                   10                  15 ggg gat aag cgc tgt aag ctt ctg ctg ggg ata gga att ctg gtg ctc      96
Gly Asp Lys Arg Cys Lys Leu Leu Leu Gly Ile Gly Ile Leu Val Leu
                20                  25                  30 ctg atc atc gtg att ctg ggg gtg ccc ttg att atc ttc acc atc aag     144
Leu Ile Ile Val Ile Leu Gly Val Pro Leu Ile Ile Phe Thr Ile Lys
            35                  40                  45 gcc aac agc gag gcc tgc cgg gac ggc ctt cgg gca gtg atg gag tgt     192
Ala Asn Ser Glu Ala Cys Arg Asp Gly Leu Arg Ala Val Met Glu Cys
        50                  55                  60 cgc aat gtc acc cat ctc ctg caa caa gag ctg acc gag gcc cag aag     240
Arg Asn Val Thr His Leu Leu Gln Gln Glu Leu Thr Glu Ala Gln Lys
    65                  70                  75 ggc ttt cag gat gtg gag gcc cag gcc gcc acc tgc aac cac act gtg     288
Gly Phe Gln Asp Val Glu Ala Gln Ala Ala Thr Cys Asn His Thr Val
80                  85                  90                  95 atg gcc cta atg gct tcc ctg gat gca gag aag gcc caa gga caa aag     336
Met Ala Leu Met Ala Ser Leu Asp Ala Glu Lys Ala Gln Gly Gln Lys
                100                 105                 110 aaa gtg gag gag ctt gag gga gag atc act aca tta aac cat aag ctt     384
Lys Val Glu Glu Leu Glu Gly Glu Ile Thr Thr Leu Asn His Lys Leu
            115                 120                 125 cag gac gcg tct gca gag gtg gag cga ctg aga aga gaa aac cag gtc     432
Gln Asp Ala Ser Ala Glu Val Glu Arg Leu Arg Arg Glu Asn Gln Val
        130                 135                 140 tta agc gtg aga atc gcg gac aag aag tac tac ccc agc tcc cag gac     480
Leu Ser Val Arg Ile Ala Asp Lys Lys Tyr Tyr Pro Ser Ser Gln Asp
    145                 150                 155 tcc agc tcc gct gcg gcg ccc cag ctg ctg att gtg ctg ctg ggc ctc     528
Ser Ser Ser Ala Ala Ala Pro Gln Leu Leu Ile Val Leu Leu Gly Leu
160                 165                 170                 175 agc gct ctg ctg cag tgagatccca ggaagctggc acatcttgga aggtccgtcc     583
Ser Ala Leu Leu Gln
                180 tgctcggctt ttcgcttgaa cattcccttg atctcatcag ttctgagcgg gtcatggggc    643 aacacggtta gcggggagag cacggggtag ccggagaagg gcctctggag caggtctgga    703 ggggccatgg ggcagtcctg ggtgtgggga cacagtcggg ttgacccagg gctgtctccc    763 tccagagcct ccctccggac aatgagtccc ccctcttgtc tcccaccctg agattgggca    823 tggggtgcgg tgtgggggc atgtgctgcc tgttgttatg ggt                       866
```

<210> SEQ ID NO 2
<211> LENGTH: 180
<212> TYPE: PRT
<213> ORGANISM: Homo sapiens

<400> SEQUENCE: 2

```
Met Ala Ser Thr Ser Tyr Asp Tyr Cys Arg Val Pro Met Glu Asp Gly
1               5                   10                  15

Asp Lys Arg Cys Lys Leu Leu Leu Gly Ile Gly Ile Leu Val Leu Leu
                20                  25                  30

Ile Ile Val Ile Leu Gly Val Pro Leu Ile Ile Phe Thr Ile Lys Ala
            35                  40                  45
```

```
Asn Ser Glu Ala Cys Arg Asp Gly Leu Arg Ala Val Met Glu Cys Arg
     50                  55                  60

Asn Val Thr His Leu Leu Gln Gln Glu Leu Thr Glu Ala Gln Lys Gly
 65                  70                  75                  80

Phe Gln Asp Val Glu Ala Gln Ala Ala Thr Cys Asn His Thr Val Met
                 85                  90                  95

Ala Leu Met Ala Ser Leu Asp Ala Glu Lys Ala Gln Gly Gln Lys Lys
                100                 105                 110

Val Glu Glu Leu Glu Gly Glu Ile Thr Thr Leu Asn His Lys Leu Gln
            115                 120                 125

Asp Ala Ser Ala Glu Val Glu Arg Leu Arg Arg Glu Asn Gln Val Leu
        130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Gly Leu Ser
                165                 170                 175

Ala Leu Leu Gln
            180

<210> SEQ ID NO 3
<211> LENGTH: 480
<212> TYPE: DNA
<213> ORGANISM: Homo sapiens
<220> FEATURE:
<221> NAME/KEY: CDS
<222> LOCATION: (4)..(480)
<223> OTHER INFORMATION:

<400> SEQUENCE: 3 tgg atg gca tct act tcg tat gac tat tgc aga gtg ccc atg gaa gac      48
    Met Ala Ser Thr Ser Tyr Asp Tyr Cys Arg Val Pro Met Glu Asp
    1               5                  10                  15 ggg gat aag cgc tgt aag ctt ctg ctg ggg ata gga att ctg gtg ctc      96
Gly Asp Lys Arg Cys Lys Leu Leu Leu Gly Ile Gly Ile Leu Val Leu
                 20                  25                  30 ctg atc atc gtg att ctg ggg gtg ccc ttg att atc ttc acc atc aag     144
Leu Ile Ile Val Ile Leu Gly Val Pro Leu Ile Ile Phe Thr Ile Lys
             35                  40                  45 gcc aac agc gag gcc tgc cgg gac ggc ctt cgg gca gtg atg gag tgt     192
Ala Asn Ser Glu Ala Cys Arg Asp Gly Leu Arg Ala Val Met Glu Cys
         50                  55                  60 cgc aat gtc acc cat ctc ctg caa caa gag ctg acc gag gcc cag aag     240
Arg Asn Val Thr His Leu Leu Gln Gln Glu Leu Thr Glu Ala Gln Lys
 65                  70                  75 ggc ttt cag gat gtg gag gcc cag gcc gcc acc tgc aac cac act gtg     288
Gly Phe Gln Asp Val Glu Ala Gln Ala Ala Thr Cys Asn His Thr Val
 80                  85                  90                  95 atg gcc cta atg gct tcc ctg gat gca gag aag gcc caa gga caa aag     336
Met Ala Leu Met Ala Ser Leu Asp Ala Glu Lys Ala Gln Gly Gln Lys
                100                 105                 110 aaa gtg gag gag ctt gag gga gag atc act aca tta aac cat aag ctt     384
Lys Val Glu Glu Leu Glu Gly Glu Ile Thr Thr Leu Asn His Lys Leu
            115                 120                 125 cag gac gcg tct gca gag gtg gag cga ctg agg tca gag ata gcc ttc     432
Gln Asp Ala Ser Ala Glu Val Glu Arg Leu Arg Ser Glu Ile Ala Phe
        130                 135                 140 ccc cgc tac cct cca cct gcc aca ttc ctc tca ccc cca cat ccc tag     480
Pro Arg Tyr Pro Pro Pro Ala Thr Phe Leu Ser Pro Pro His Pro
145                 150                 155
```

```
<210> SEQ ID NO 4
<211> LENGTH: 158
<212> TYPE: PRT
<213> ORGANISM: Homo sapiens

<400> SEQUENCE: 4

Met Ala Ser Thr Ser Tyr Asp Tyr Cys Arg Val Pro Met Glu Asp Gly
1               5                   10                  15

Asp Lys Arg Cys Lys Leu Leu Leu Gly Ile Gly Ile Leu Val Leu Leu
            20                  25                  30

Ile Ile Val Ile Leu Gly Val Pro Leu Ile Ile Phe Thr Ile Lys Ala
        35                  40                  45

Asn Ser Glu Ala Cys Arg Asp Gly Leu Arg Ala Val Met Glu Cys Arg
50                  55                  60

Asn Val Thr His Leu Leu Gln Gln Glu Leu Thr Glu Ala Gln Lys Gly
65                  70                  75                  80

Phe Gln Asp Val Glu Ala Gln Ala Ala Thr Cys Asn His Thr Val Met
                85                  90                  95

Ala Leu Met Ala Ser Leu Asp Ala Glu Lys Ala Gln Gly Gln Lys Lys
            100                 105                 110

Val Glu Glu Leu Glu Gly Glu Ile Thr Thr Leu Asn His Lys Leu Gln
        115                 120                 125

Asp Ala Ser Ala Glu Val Glu Arg Leu Arg Ser Glu Ile Ala Phe Pro
130                 135                 140

Arg Tyr Pro Pro Pro Ala Thr Phe Leu Ser Pro Pro His Pro
145                 150                 155

<210> SEQ ID NO 5
<211> LENGTH: 314
<212> TYPE: DNA
<213> ORGANISM: Homo sapiens
<220> FEATURE:
<221> NAME/KEY: CDS
<222> LOCATION: (4)..(306)
<223> OTHER INFORMATION:

<400> SEQUENCE: 5 tgg atg gca tct act tcg tat gac tat tgc aga gtg ccc atg gaa gac      48
    Met Ala Ser Thr Ser Tyr Asp Tyr Cys Arg Val Pro Met Glu Asp
    1               5                   10                  15 ggg gat aag cgc tgt aag ctt ctg ctg ggg ata gga att ctg gtg ctc      96
Gly Asp Lys Arg Cys Lys Leu Leu Leu Gly Ile Gly Ile Leu Val Leu
            20                  25                  30 ctg atc atc gtg att ctg ggg gtg ccc ttg att atc ttc acc atc aag     144
Leu Ile Ile Val Ile Leu Gly Val Pro Leu Ile Ile Phe Thr Ile Lys
        35                  40                  45 gcc aac agc gag gcc tgc cgg gac ggc ctt cgg gca gtg atg gag tgt     192
Ala Asn Ser Glu Ala Cys Arg Asp Gly Leu Arg Ala Val Met Glu Cys
    50                  55                  60 cgc aat gtc acc cat ctc ctg caa caa gag ctg acc gag gcc cag aag     240
Arg Asn Val Thr His Leu Leu Gln Gln Glu Leu Thr Glu Ala Gln Lys
65                  70                  75 ggc ttt cag gat gtg gag gcc cag gcc gcc acc tgc aac cac act gtg     288
Gly Phe Gln Asp Val Glu Ala Gln Ala Ala Thr Cys Asn His Thr Val
80                  85                  90                  95 gag aga tca cta cat taaaccataa g                                    314
Glu Arg Ser Leu His
                100

<210> SEQ ID NO 6
<211> LENGTH: 100
```

-continued

```
<212> TYPE: PRT
<213> ORGANISM: Homo sapiens

<400> SEQUENCE: 6

Met Ala Ser Thr Ser Tyr Asp Tyr Cys Arg Val Pro Met Glu Asp Gly
1               5                   10                  15

Asp Lys Arg Cys Lys Leu Leu Leu Gly Ile Gly Ile Leu Val Leu Leu
            20                  25                  30

Ile Ile Val Ile Leu Gly Val Pro Leu Ile Ile Phe Thr Ile Lys Ala
        35                  40                  45

Asn Ser Glu Ala Cys Arg Asp Gly Leu Arg Ala Val Met Glu Cys Arg
50                  55                  60

Asn Val Thr His Leu Leu Gln Gln Glu Leu Thr Glu Ala Gln Lys Gly
65                  70                  75                  80

Phe Gln Asp Val Glu Ala Gln Ala Ala Thr Cys Asn His Thr Val Glu
                85                  90                  95

Arg Ser Leu His
            100

<210> SEQ ID NO 7
<211> LENGTH: 906
<212> TYPE: DNA
<213> ORGANISM: Mus musculus
<220> FEATURE:
<221> NAME/KEY: CDS
<222> LOCATION: (10)..(546)
<223> OTHER INFORMATION:

<400> SEQUENCE: 7 acggatcac atg gcg ccc tct ttc tat cac tat ctg ccc gtg ccc atg gat      51
          Met Ala Pro Ser Phe Tyr His Tyr Leu Pro Val Pro Met Asp
          1               5                   10 gag atg ggg ggg aag caa gga tgg ggc agc cac cgg cag tgg ctg ggg        99
Glu Met Gly Gly Lys Gln Gly Trp Gly Ser His Arg Gln Trp Leu Gly
15                  20                  25                  30 gcc gcg atc ttg gtg gtc ctg ttc ggg gtt acc tta gtc atc ctg aca        147
Ala Ala Ile Leu Val Val Leu Phe Gly Val Thr Leu Val Ile Leu Thr
                35                  40                  45 atc tac ttc gcc gtc aca gcg aac agc gtg gcc tgt aga gac ggg ttg        195
Ile Tyr Phe Ala Val Thr Ala Asn Ser Val Ala Cys Arg Asp Gly Leu
            50                  55                  60 cga gcg cag gct gag tgc cgg aac acc acg cac ctg ttg cag cgc cag        243
Arg Ala Gln Ala Glu Cys Arg Asn Thr Thr His Leu Leu Gln Arg Gln
        65                  70                  75 ctc acc cgc acc cag gac agt ctg ctg cag gcc gag aca cag gca aac        291
Leu Thr Arg Thr Gln Asp Ser Leu Leu Gln Ala Glu Thr Gln Ala Asn
80                  85                  90 tcc tgc aac ctg acc gtg gtg acc ctt cag gag tcc ctg gag aag aag        339
Ser Cys Asn Leu Thr Val Val Thr Leu Gln Glu Ser Leu Glu Lys Lys
95                  100                 105                 110 gtg tct caa gcc ctg gag cag cag gcc cgc atc aag gag ctt gag aat        387
Val Ser Gln Ala Leu Glu Gln Gln Ala Arg Ile Lys Glu Leu Glu Asn
                115                 120                 125 gaa gtc acg aag ctg aac cag gag ctg gag aat ctg agg tta gag aca        435
Glu Val Thr Lys Leu Asn Gln Glu Leu Glu Asn Leu Arg Leu Glu Thr
            130                 135                 140 gct ctc cct gcc cac cgc cac cca ctc ccc tcc aga ctg cac ttc ctt        483
Ala Leu Pro Ala His Arg His Pro Leu Pro Ser Arg Leu His Phe Leu
        145                 150                 155 caa aac ctg ggc tcc act tgg ctc aca cag tct aca gct cag gat cca        531
Gln Asn Leu Gly Ser Thr Trp Leu Thr Gln Ser Thr Ala Gln Asp Pro
```

```
                 160                 165                 170 aaa gga gac ttc tagcacagtg caggtgaact ctggcagctc catggtggtc        583
Lys Gly Asp Phe
175 tccagcctac tggtgctcaa agtgtcactg tttctgctct tttgaggact cattagttgg  643 caggtcacag ttgtttgaag tcactatggg tcatagtgac tctggagagg tcctggcagc  703 cctgaggatg tggaaaccac tagggggctc cagattgggt cttcctccgc agaactttag  763 gactggggag tggggaggga gttctgcttt attgcttttg cagttattgg ggggggggg   823 gtcacatatt tctggtgtct ttgacctgga aaataaagt aatttaaaaa gaaagagctt   883 gcttctaaaa aaaaaaaaaa aaa                                          906

<210> SEQ ID NO 8
<211> LENGTH: 178
<212> TYPE: PRT
<213> ORGANISM: Mus musculus

<400> SEQUENCE: 8

Met Ala Pro Ser Phe Tyr His Tyr Leu Pro Val Pro Met Asp Glu Met
1               5                   10                  15

Gly Gly Lys Gln Gly Trp Gly Ser His Arg Gln Trp Leu Gly Ala Ala
            20                  25                  30

Ile Leu Val Val Leu Phe Gly Val Thr Leu Val Ile Leu Thr Ile Tyr
        35                  40                  45

Phe Ala Val Thr Ala Asn Ser Val Ala Cys Arg Asp Gly Leu Arg Ala
    50                  55                  60

Gln Ala Glu Cys Arg Asn Thr Thr His Leu Leu Gln Arg Gln Leu Thr
65                  70                  75                  80

Arg Thr Gln Asp Ser Leu Leu Gln Ala Glu Thr Gln Ala Asn Ser Cys
                85                  90                  95

Asn Leu Thr Val Val Thr Leu Gln Glu Ser Leu Glu Lys Lys Val Ser
            100                 105                 110

Gln Ala Leu Glu Gln Gln Ala Arg Ile Lys Glu Leu Glu Asn Glu Val
        115                 120                 125

Thr Lys Leu Asn Gln Glu Leu Glu Asn Leu Arg Leu Glu Thr Ala Leu
    130                 135                 140

Pro Ala His Arg His Pro Leu Pro Ser Arg Leu His Phe Leu Gln Asn
145                 150                 155                 160

Leu Gly Ser Thr Trp Leu Thr Gln Ser Thr Ala Gln Asp Pro Lys Gly
                165                 170                 175

Asp Phe

<210> SEQ ID NO 9
<211> LENGTH: 807
<212> TYPE: DNA
<213> ORGANISM: Mus musculus
<220> FEATURE:
<221> NAME/KEY: CDS
<222> LOCATION: (11)..(529)
<223> OTHER INFORMATION:

<400> SEQUENCE: 9
gacggatcac atg gcg ccc tct ttc tat cac tat ctg ccc gtg ccc atg    49
           Met Ala Pro Ser Phe Tyr His Tyr Leu Pro Val Pro Met
           1               5                   10 gat gag atg ggg ggg aag caa gga tgg ggc agc cac cgg cag tgg ctg   97
Asp Glu Met Gly Gly Lys Gln Gly Trp Gly Ser His Arg Gln Trp Leu
        15                  20                  25
```

```
ggg gcc gcg atc ttg gtg gtc ctg ttc ggg gtt acc tta gtc atc ctg      145
Gly Ala Ala Ile Leu Val Val Leu Phe Gly Val Thr Leu Val Ile Leu
 30              35                  40                  45 aca atc tac ttc gcc gtc aca gcg aac agc gtg gcc tgt aga gac ggg      193
Thr Ile Tyr Phe Ala Val Thr Ala Asn Ser Val Ala Cys Arg Asp Gly
                 50                  55                  60 ttg cga gcg cag gct gag tgc cgg aac acc acg cac ctg ttg cag cgc      241
Leu Arg Ala Gln Ala Glu Cys Arg Asn Thr Thr His Leu Leu Gln Arg
             65                  70                  75 cag ctc acc cgc acc cag gac agt ctg ctg cag gcc gag aca cag gca      289
Gln Leu Thr Arg Thr Gln Asp Ser Leu Leu Gln Ala Glu Thr Gln Ala
         80                  85                  90 aac tcc tgc aac ctg acc gtg gtg acc ctt cag gag tcc ctg gag aag      337
Asn Ser Cys Asn Leu Thr Val Val Thr Leu Gln Glu Ser Leu Glu Lys
     95                  100                 105 aag gtg tct caa gcc ctg gag cag cag gcc cgc atc aag gag ctt gag      385
Lys Val Ser Gln Ala Leu Glu Gln Gln Ala Arg Ile Lys Glu Leu Glu
110                 115                 120                 125 aat gaa gtc acg aag ctg aac cag gag ctg gag aat ctg agg atc caa      433
Asn Glu Val Thr Lys Leu Asn Gln Glu Leu Glu Asn Leu Arg Ile Gln
                 130                 135                 140 aag gag act tct agc aca gtg cag gtg aac tct ggc agc tcc atg gtg      481
Lys Glu Thr Ser Ser Thr Val Gln Val Asn Ser Gly Ser Ser Met Val
             145                 150                 155 gtc tcc agc cta ctg gtg ctc aaa gtg tca ctg ttt ctg ctc ttt tga      529
Val Ser Ser Leu Leu Val Leu Lys Val Ser Leu Phe Leu Leu Phe
         160                 165                 170 ggactcatta gttggcaggt cacagttgtt tgaagtcact atgggtcata gtgactctgg     589
agaggtcctg gcagccctga ggatgtggaa accactaggg ggctccagat tgggtcttcc     649
tccgcagaac tttaggactg gggagtgggg agggagttct gctttattgc ttttgcagtt     709 attgggggggg gggggtcac atatttctgg tgtctttgac ctggaaaaat aaagtaattt     769
aaaaagaaag agcttgcttc taaaaaaaaa aaaaaaaa                             807

<210> SEQ ID NO 10
<211> LENGTH: 172
<212> TYPE: PRT
<213> ORGANISM: Mus musculus

<400> SEQUENCE: 10

Met Ala Pro Ser Phe Tyr His Tyr Leu Pro Val Pro Met Asp Glu Met
 1               5                  10                  15

Gly Gly Lys Gln Gly Trp Gly Ser His Arg Gln Trp Leu Gly Ala Ala
            20                  25                  30

Ile Leu Val Val Leu Phe Gly Val Thr Leu Val Ile Leu Thr Ile Tyr
        35                  40                  45

Phe Ala Val Thr Ala Asn Ser Val Ala Cys Arg Asp Gly Leu Arg Ala
    50                  55                  60

Gln Ala Glu Cys Arg Asn Thr Thr His Leu Leu Gln Arg Gln Leu Thr
65                  70                  75                  80

Arg Thr Gln Asp Ser Leu Leu Gln Ala Glu Thr Gln Ala Asn Ser Cys
                85                  90                  95

Asn Leu Thr Val Val Thr Leu Gln Glu Ser Leu Glu Lys Lys Val Ser
            100                 105                 110

Gln Ala Leu Glu Gln Gln Ala Arg Ile Lys Glu Leu Glu Asn Glu Val
        115                 120                 125

Thr Lys Leu Asn Gln Glu Leu Glu Asn Leu Arg Ile Gln Lys Glu Thr
```

|   |   |   |   |   |   |   |   |   |   |
|---|---|---|---|---|---|---|---|---|---|
| Ser | Ser | Thr | Val | Gln | Val | Asn | Ser | Gly | Ser |
| 145 | | | | 150 | | | | | 155 |
| Ser | Met | Val | Val | Ser | Ser | | | | |
| | | 160 | | | | | | | |
| Leu | Leu | Val | Leu | Lys | Val | Ser | Leu | Phe | Leu |
| | | | 165 | | | | | 170 | |
| Leu | Phe | | | | | | | | |

```
                130                 135                 140
Ser Ser Thr Val Gln Val Asn Ser Gly Ser Ser Met Val Val Ser Ser
145                 150                 155                 160
Leu Leu Val Leu Lys Val Ser Leu Phe Leu Leu Phe
                165                 170
```

<210> SEQ ID NO 11
<211> LENGTH: 84
<212> TYPE: DNA
<213> ORGANISM: Artificial
<220> FEATURE:
<223> OTHER INFORMATION: Artificially synthesized primer sequence

<400> SEQUENCE: 11 ttttgctag cgacggatca catggcgccc tctttctatc actatctgcc cgtgcccatg   60
gatgagatgg gggggaagca agga                                        84

<210> SEQ ID NO 12
<211> LENGTH: 38
<212> TYPE: DNA
<213> ORGANISM: Artificial
<220> FEATURE:
<223> OTHER INFORMATION: Artificially synthesized primer sequence

<400> SEQUENCE: 12 ttttttctc gagtcctcaa aagagcagga acagtgac                          38

<210> SEQ ID NO 13
<211> LENGTH: 26
<212> TYPE: DNA
<213> ORGANISM: Artificial
<220> FEATURE:
<223> OTHER INFORMATION: Artificially synthesized primer sequence

<400> SEQUENCE: 13
ccagctcacc cgcacccagg acagtc                                      26

<210> SEQ ID NO 14
<211> LENGTH: 60
<212> TYPE: DNA
<213> ORGANISM: Artificial
<220> FEATURE:
<223> OTHER INFORMATION: Artificially synthesized primer sequence

<400> SEQUENCE: 14 ttttttctc gagtcaatga tgatgatgat gatgaaagag cagaaacagt gacactttga   60

<210> SEQ ID NO 15
<211> LENGTH: 60
<212> TYPE: DNA
<213> ORGANISM: Artificial
<220> FEATURE:
<223> OTHER INFORMATION: Artificially synthesized primer sequence

<400> SEQUENCE: 15 ttttttctc gagtcaatga tgatgatgat gatggaagtc tccttttgga tcctgagctg   60

<210> SEQ ID NO 16
<211> LENGTH: 23
<212> TYPE: DNA
<213> ORGANISM: Artificial
<220> FEATURE:
<223> OTHER INFORMATION: Artificially synthesized primer sequence for
      RT-PCR

<400> SEQUENCE: 16

```
acatggcgcc ctctttctat cac                                              23
```

<210> SEQ ID NO 17
<211> LENGTH: 23
<212> TYPE: DNA
<213> ORGANISM: Artificial
<220> FEATURE:
<223> OTHER INFORMATION: Artificially synthesized primer sequence for
      RT-PCR

<400> SEQUENCE: 17

```
gagcccaggt tttgaaggaa gtg                                              23
```

<210> SEQ ID NO 18
<211> LENGTH: 23
<212> TYPE: DNA
<213> ORGANISM: Artificial
<220> FEATURE:
<223> OTHER INFORMATION: Artificially synthesized primer sequence for
      RT-PCR

<400> SEQUENCE: 18

```
agctcacccg cacccaggac agt                                              23
```

<210> SEQ ID NO 19
<211> LENGTH: 22
<212> TYPE: DNA
<213> ORGANISM: Artificial
<220> FEATURE:
<223> OTHER INFORMATION: Artificially synthesized primer sequence for
      RT-PCR

<400> SEQUENCE: 19

```
cactccccag tcctaaagtt ct                                               22
```

<210> SEQ ID NO 20
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 20

```
gtgggccgct ctaggcacca a                                                21
```

<210> SEQ ID NO 21
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 21

```
ctctttgatg tcacgcacga tttc                                             24
```

<210> SEQ ID NO 22
<211> LENGTH: 831
<212> TYPE: DNA
<213> ORGANISM: Mus musculus
<220> FEATURE:
<221> NAME/KEY: CDS
<222> LOCATION: (11)..(328)
<223> OTHER INFORMATION:

<400> SEQUENCE: 22

```
gacggatcac  atg gcg ccc tct ttc tat cac tat ctg ccc gtg ccc atg        49
            Met Ala Pro Ser Phe Tyr His Tyr Leu Pro Val Pro Met
```

```
                1               5                       10
gat gag atg ggg ggg aag caa gga tgg ggc agc cac cgg cag tgg ctg      97
Asp Glu Met Gly Gly Lys Gln Gly Trp Gly Ser His Arg Gln Trp Leu
 15                  20                  25 ggg gcc gcg atc ttg gtg gtc ctg ttc ggg gtt acc tta gtc atc ctg     145
Gly Ala Ala Ile Leu Val Val Leu Phe Gly Val Thr Leu Val Ile Leu
 30                  35                  40                  45 aca atc tac ttc gcc gtc aca gcg aac agc gtg gcc tgt aga gac ggg     193
Thr Ile Tyr Phe Ala Val Thr Ala Asn Ser Val Ala Cys Arg Asp Gly
                 50                  55                  60 ttg cga gcg cag gct gag tgc cgg aac acc acg cac ctg ttg cag cgc     241
Leu Arg Ala Gln Ala Glu Cys Arg Asn Thr Thr His Leu Leu Gln Arg
             65                  70                  75 cag ctc acc cgc acc cag gac agt ctg ctg cag gcc gag aca cag gca     289
Gln Leu Thr Arg Thr Gln Asp Ser Leu Leu Gln Ala Glu Thr Gln Ala
         80                  85                  90 aac tcc tgc aac ctg acc gtg atg aag tca cga agc tgaaccagga          335
Asn Ser Cys Asn Leu Thr Val Met Lys Ser Arg Ser
     95                 100                 105 gctggagaat ctgaggttag agacagctct ccctgccacc cgccaccac tcccctccag    395 actgcacttc cttcaaaacc tgggctccac ttggctcaca cagtctacag ctcaggatcc   455
aaaaggagac ttctagcaca gtgcaggtga actctggcag ctccatggtg gtctccagcc   515
tactggtgct caaagtgtca ctgtttctgc tcttttgagg actcattagt tggcaggtca   575
cagttgtttg aagtcactat gggtcatagt gactctggag aggtcctggc agccctgagg   635
atgtggaaac cactaggggg ctccagattg ggtcttcctc cgcagaactt taggactggg   695
gagtggggag ggagttctgc tttattgctt ttgcagttat tggggggggg ggggtcacat   755
atttctggtg tctttgacct ggaaaaataa agtaatttaa aagaaagag cttgcttcta    815 aaaaaaaaaa aaaaa                                                    831
```

<210> SEQ ID NO 23
<211> LENGTH: 105
<212> TYPE: PRT
<213> ORGANISM: Mus musculus

<400> SEQUENCE: 23

Met Ala Pro Ser Phe Tyr His Tyr Leu Pro Val Pro Met Asp Glu Met
 1               5                  10                  15

Gly Gly Lys Gln Gly Trp Gly Ser His Arg Gln Trp Leu Gly Ala Ala
             20                  25                  30

Ile Leu Val Val Leu Phe Gly Val Thr Leu Val Ile Leu Thr Ile Tyr
         35                  40                  45

Phe Ala Val Thr Ala Asn Ser Val Ala Cys Arg Asp Gly Leu Arg Ala
     50                  55                  60

Gln Ala Glu Cys Arg Asn Thr Thr His Leu Leu Gln Arg Gln Leu Thr
 65                  70                  75                  80

Arg Thr Gln Asp Ser Leu Leu Gln Ala Glu Thr Gln Ala Asn Ser Cys
                 85                  90                  95

Asn Leu Thr Val Met Lys Ser Arg Ser
            100                 105

<210> SEQ ID NO 24
<211> LENGTH: 84
<212> TYPE: DNA
<213> ORGANISM: Artificial
<220> FEATURE:
<223> OTHER INFORMATION: Artificially synthesized primer sequence

```
<400> SEQUENCE: 24
tttttgctag cgacggatca catggcgccc tctttctatc actatctgcc cgtgcccatg      60
gatgagatgg gggggaagca agga                                            84

<210> SEQ ID NO 25
<211> LENGTH: 38
<212> TYPE: DNA
<213> ORGANISM: Artificial
<220> FEATURE:
<223> OTHER INFORMATION: Artificially synthesized primer sequence

<400> SEQUENCE: 25 ttttttctc gagtcctcaa aagagcagga acagtgac                              38

<210> SEQ ID NO 26
<211> LENGTH: 35
<212> TYPE: DNA
<213> ORGANISM: Artificial
<220> FEATURE:
<223> OTHER INFORMATION: Artificially synthesized primer sequence

<400> SEQUENCE: 26
aaaaaaagct agctggatgg catctacttc gtatg                                35

<210> SEQ ID NO 27
<211> LENGTH: 36
<212> TYPE: DNA
<213> ORGANISM: Artificial
<220> FEATURE:
<223> OTHER INFORMATION: Artificially synthesized primer sequence

<400> SEQUENCE: 27
aaaaaaactc gagacccata acaacaggca gcacat                               36

<210> SEQ ID NO 28
<211> LENGTH: 100
<212> TYPE: DNA
<213> ORGANISM: Artificial
<220> FEATURE:
<223> OTHER INFORMATION: Artificially synthesized primer sequence

<400> SEQUENCE: 28 tttttttctcg agctagggat gtgggggtga gaggaatgtg gcaggtggag ggtagcgggg    60
gaaggctatc tctgacctca gtcgctccac ctctgcagac                          100

<210> SEQ ID NO 29
<211> LENGTH: 65
<212> TYPE: DNA
<213> ORGANISM: Artificial
<220> FEATURE:
<223> OTHER INFORMATION: Artificially synthesized primer sequence

<400> SEQUENCE: 29
aaaaaaactc gagcttatgg tttaatgtag tgatctctcc acagtgtggt tgcaggtggc     60
ggcct                                                                65

<210> SEQ ID NO 30
<211> LENGTH: 24
<212> TYPE: DNA
<213> ORGANISM: Artificial
<220> FEATURE:
<223> OTHER INFORMATION: Artificially synthesized primer sequence

<400> SEQUENCE: 30
```

```
gccttcgggc agtgatggag tgtc                                          24

<210> SEQ ID NO 31
<211> LENGTH: 23
<212> TYPE: DNA
<213> ORGANISM: Artificial
<220> FEATURE:
<223> OTHER INFORMATION: Artificially synthesized primer sequence

<400> SEQUENCE: 31
tcaagcgaaa agccgagcag gac                                           23

<210> SEQ ID NO 32
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 32
aatgtggcag gtggagggta g                                             21
```